US010081675B2

(12) United States Patent
Dodeller et al.

(10) Patent No.: US 10,081,675 B2
(45) Date of Patent: *Sep. 25, 2018

(54) ANTIBODIES TARGETING M-CSF

(71) Applicant: MORPHOSYS AG, Planegg (DE)

(72) Inventors: Francis Dodeller, Gilching (DE); Robert Rauchenberger, Farchant (DE)

(73) Assignee: MORPHOSYS AG, Planegg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/795,364

(22) Filed: Oct. 27, 2017

(65) Prior Publication Data

US 2018/0057581 A1  Mar. 1, 2018

Related U.S. Application Data

(62) Division of application No. 14/781,601, filed as application No. PCT/EP2014/057630 on Apr. 11, 2014, now Pat. No. 9,856,316.

(30) Foreign Application Priority Data

Apr. 12, 2013 (EP) .................................. 13163542

(51) Int. Cl.
   *A61K 39/00*   (2006.01)
   *A61K 39/395*  (2006.01)
   *C07K 16/24*   (2006.01)

(52) U.S. Cl.
CPC ........ *C07K 16/243* (2013.01); *C07K 2317/24* (2013.01); *C07K 2317/33* (2013.01); *C07K 2317/56* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,642,821 A | 4/1997 | Winter et al. | 435/69.6 |
| 7,108,852 B2 | 9/2006 | Devalaraja | |
| 7,332,581 B2 | 2/2008 | Presta | 530/387.1 |
| 8,142,777 B2 | 3/2012 | Hamilton | |
| 2002/0141994 A1 | 10/2002 | Devalaraja | |
| 2009/0110681 A1 | 4/2009 | Carroll | |
| 2011/0091451 A1 | 4/2011 | Kavanaugh | |
| 2014/0286959 A1 | 9/2014 | Hegen et al. | 424/145.1 |

FOREIGN PATENT DOCUMENTS

| | | |
|---|---|---|
| WO | 1990009400 | 8/1990 |
| WO | 1999017798 | 4/1999 |
| WO | 200105950 | 1/2001 |
| WO | 200130381 | 5/2001 |
| WO | 2003032904 | 4/2003 |
| WO | 200348731 | 6/2003 |
| WO | 2003055442 | 7/2003 |
| WO | 2003073981 | 9/2003 |
| WO | 2004045532 | 6/2004 |
| WO | 2005030124 | 4/2005 |
| WO | 2005046657 | 5/2005 |
| WO | 2005068503 | 7/2005 |
| WO | 2009026303 | 2/2006 |
| WO | 2006096461 | 9/2006 |
| WO | 2007011896 | 1/2007 |
| WO | 2007016240 | 2/2007 |
| WO | 2007016285 | 2/2007 |
| WO | 2007081879 | 7/2007 |
| WO | 2008124129 | 10/2008 |
| WO | 2009075344 | 6/2009 |
| WO | 2010017224 | 2/2010 |
| WO | 2011070024 | 6/2011 |
| WO | 2011107553 | 9/2011 |
| WO | 2011131407 | 10/2011 |
| WO | 2011140249 | 11/2011 |
| WO | 2012110360 | 8/2012 |
| WO | 2013068902 | 5/2013 |

OTHER PUBLICATIONS

Kolchanov, Journal of Molecular Evolution, vol. 27, pp. 154-162 (Year: 1988).*
Pasquo, PLoS ONE, vol. 7, Issue 2, e32555, pp. 1-11 (Year: 2012).*
Ward et al., (1989) Nature 341:544-546.
Bird et al., (1988) Science 242:423-426.
Huston et al., (1988) Proc. Natl. Acad. Sci. 85:5879-5883.
Knappik et al., (2000) J. Mol. Biol. 296:57-86.
Morrison et al., (1994) Proc. Nattl. Acad. Sci. USA, 81:6851-6855.
Morrison and Oi (1988) Adv. Immunol., 44:65-92.
Verhoeyen et al., (1988) Science, 239:1534-1536.
Padlan, Molec (1991) Immun., 28:489-498.
Padlan Molec (1994) Immun. 31:169-217.
Batzer et al., (1991) Nucleic Acid Res. 19:5081.
Ohtsuka et al., (1985) J. Biol. Chem. 260:2605-2608.
Rossolini et al., (1994) Mol. Cell. Probes 8:91-98.
Hume et al., "Therapeutic applications of Macrophage colony-stimulating factor-1 (CSF-1) and antagonists of CSF-1 receptor (CSF-1R) signaling", Blood, vol. 119, No. 8, Feb. 23, 2012.

(Continued)

*Primary Examiner* — Daniel E Kolker
*Assistant Examiner* — Jegatheesan Seharaseyon
(74) *Attorney, Agent, or Firm* — Licata & Tyrrell P.C.

(57) ABSTRACT

This disclosure generally relates to antibodies or antibody fragments which specifically bind to M-CSF. In particular antibodies and antibody fragments are disclosed which bind to M-CSF and which inhibit binding of M-CSF to the M-CSF receptor with an IC50 of 10 pM or less. The invention also relates to nucleic acids, vectors and host cells capable of expressing the antibodies or fragments thereof of the invention, pharmaceutical compositions comprising the antibodies or fragments thereof and uses of said antibodies or fragments thereof and compositions for treatment of specific diseases.

10 Claims, 1 Drawing Sheet

Specification includes a Sequence Listing.

(56) References Cited

OTHER PUBLICATIONS

International Search Report PCT/EP2014/057360 dated Jul. 16, 2014.
European Search Report EP 13163542.7 dated Jul. 26, 2013.
Patel S. et al.: "Colony-stimulation factor-1 receptor inhibitors for the treatment of cancer and inflammatory disease", Current Topics in Medicinal Chemistry, vol. 9, No. 7, 2009.
Wei Suwen, et al.: "Functional overlap but differential expression of CSF-1 and Il-34 in their CSF-1 receptor-mediated regulation of myeloid cells", Journal of Leukocyte Biology, vol. 88, No. 3, 2010.
Lin Haishan, et al.: "Discovery of a cytokine and its receptor by functional screening of the extracellular proteome", Science, vol. 320, No. 5877, 2008, pp. 807-811.
Chen Zhi, et al.: "The critical role of IL-34 in osteoclastogenesis" PLOS One, vol. 6, No. 4, E18689, 2011, pp. 1-10.
EP11174305.0 Extended European Search Report dated Dec. 21, 2011.
PCT/EP2012/063998 International Search Report dated Oct. 12, 2012.
Office Communication dated Mar. 15, 2017 in U.S. Appl. No. 14/781,601, filed Oct. 1, 2015.
Office Communication dated Sep. 22, 2017 in U.S. Appl. No. 14/781,601, filed Oct. 1, 2015.
International Preliminary Report on Patentability in PCT/EP2014/057360 dated Oct. 13, 2015.

\* cited by examiner

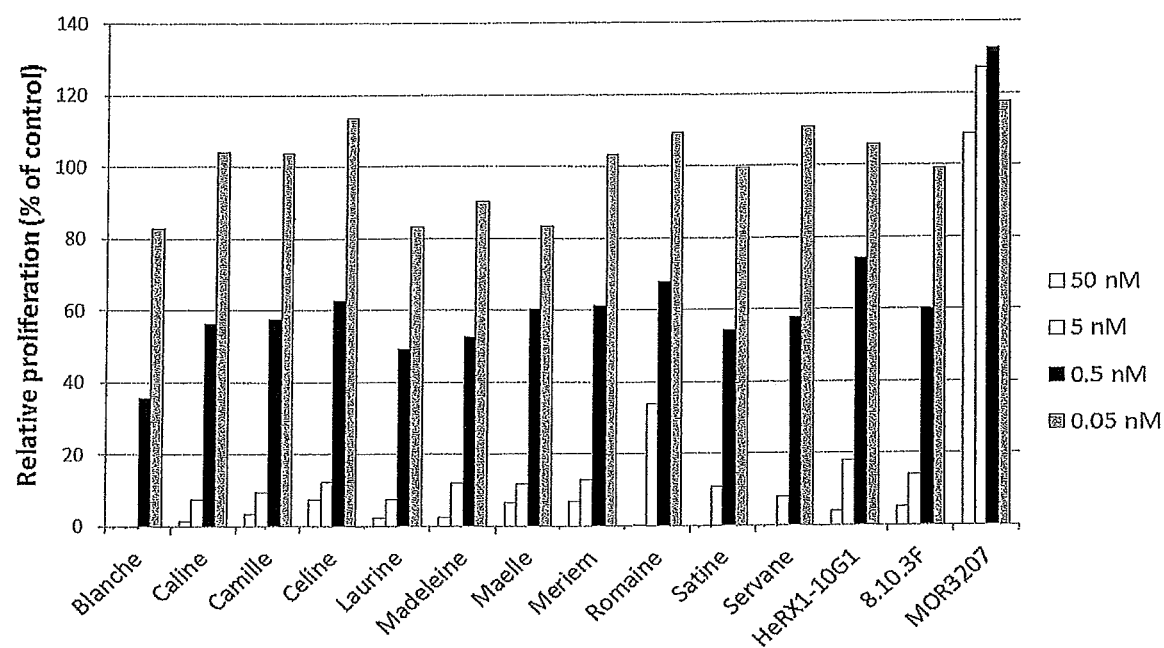

US 10,081,675 B2

ANTIBODIES TARGETING M-CSF

This patent application is a divisional of U.S. application Ser. No. 14/781,601, filed Oct. 1, 2015, which is U.S. National Stage of PCT/EP2014/057360, filed Apr. 11, 2014, which claims the benefit of priority from EP 13163542.7, filed Apr. 12, 2013, the contents of each of which are herein incorporated by reference in their entirety.

FIELD

This disclosure generally relates to antibodies or antibody fragments which specifically bind to M-CSF. In particular antibodies and antibody fragments are disclosed which bind to M-CSF and which inhibit binding of M-CSF to the M-CSF receptor with an IC50 of 10 pM or less. The invention also relates to nucleic acids, vectors and host cells capable of expressing the antibodies or fragments thereof of the invention, pharmaceutical compositions comprising the antibodies or fragments thereof and uses of said antibodies or fragments thereof and compositions for treatment of specific diseases.

BACKGROUND OF THE INVENTION

M-CSF is a secreted cytokine which influences hematopoietic stem cells to differentiate into macrophages or other related cell types. The active form of M-CSF is found extracellularly as a disulfide-linked homodimer. Three different isoforms of M-CSF are found extracellularly: secreted glycosylated M-CSF, secreted proteoglycan M-CSF, and cell-surface M-CSF.

M-CSF is a validated target for therapeutic invention, in particularly for the treatment of inflammatory disorders, such as e.g. rheumatoid arthritis. See e.g. U.S. Pat. No. 8,142,777 which is incorporated by reference. Several molecules are under development which target M-CSF, including antibody approaches. See e.g. WO2005/030124 (Warner-Lambert/Pfizer) WO2005/068503 and (Chiron/Novartis).

The present disclosure provides novel antibodies and antibody fragments which are superior to the anti-M-CSF antibodies known from the prior art. In particular, the antibodies and antibody fragments of the present disclosure specifically bind to M-CSF and inhibit the binding of M-CSF to the M-CSF receptor with an IC50 of 10 pM or less in a receptor binding inhibition assay comprising M-CSF at a final concentration of 12.5 pM. In addition, the antibodies exhibit functional properties which are highly desirable for clinical development and which never have been observed before.

SUMMARY OF THE INVENTION

The present disclosure provides antibodies or antibody fragments which specifically bind to human M-CSF. The present disclosure also provides antibodies or antibody fragments which specifically bind to human M-CSF with a certain affinity, e.g. an affinity of 30 pM or lower. The present disclosure also provides antibodies or antibody fragments which specifically bind to M-CSF and which inhibit binding of M-CSF to the M-CSF receptor with an IC50 of 10 pM or less. The present disclosure also provides antibodies or antibody fragments which specifically binds to M-CSF and wherein said isolated antibody or antibody fragment is able to inhibit the binding of M-CSF to the M-CSF receptor with an IC50 of 10 pM or less in a receptor binding inhibition assay comprising M-CSF at a final concentration of 12.5 pM.

The present disclosure also provides specific antibodies or antibody fragments as defined by way of the amino acid sequences of the six CDR regions. The present disclosure also provides specific antibodies or antibody fragments as defined by way of the amino acid sequences of the variable heavy chain and the variable light chain.

The present disclosure also provides specific antibodies or antibody fragments which compete with the specific antibodies or antibody fragments disclosed herein. The present disclosure also provides specific antibodies or antibody fragments which bind to the same epitope as the specific antibodies or antibody fragments disclosed herein.

The present disclosure also provides the isolated antibody or antibody fragment of the present disclosure use in medicine.

The present disclosure also provides also provides methods for treating patients suffering from a disorder, such as an inflammatory disorder, by administering to said patient an effective amount of the antibodies or antibody fragments of the present disclosure.

The present disclosure also provides pharmaceutical compositions comprising the isolated antibody or antibody fragment of the present disclosure, and a pharmaceutically acceptable carrier.

The present disclosure also provides nucleic acids encoding the antibody or antibody fragment of the present disclosure.

The present disclosure also provides vector comprising nucleic acids encoding the antibodies or antibody fragment antibodies of the present disclosure.

The present disclosure also provides host cell comprising vector or nucleic acids encoding the antibodies or antibody fragments of the present disclosure.

FIGURE LEGENDS

FIG. 1 demonstrates the ability of M-CSF-specific antibodies of the present disclosure to block the bioactivity of membrane-bound M-CSF isoform in an assay in which proliferation of M-NFS-60 cells was induced by CHO cells stably expressing human membrane-bound M-CSF. With increasing antibody concentration all M-CSF-specific immunoglobulins efficiently inhibit proliferation. In contrast, MOR03207 which is specific for lysozyme failed to inhibit proliferation.

DETAILED DESCRIPTION

The term "isolated" refers to a compound that is substantially free of other cellular materials and/or chemicals. If such compound is an antibody or antibody fragment then the term "isolated" refers to an antibody or antibody fragment that is also free of other antibodies or antigen binding moieties having different antigenic specificities.

The term "antibody" as used herein includes whole antibodies. A naturally occurring "antibody" is a protein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised specific CH domains (e.g. CH1, CH2 and CH3). Each light chain is comprised of a light chain variable region (abbreviated herein as VL) and a light chain constant region. The light chain constant region is comprised of one domain, CL. The VH and VL regions can be further subdivided into regions of hypervariability, termed complementary determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The constant regions of the antibodies may mediate the binding of the immunoglobulin to host tissues or factors, including various cells of the immune system (e.g., effector cells) and the first component (C1q) of the classical complement system. The antibodies can be of any isotype (e.g., IgG, IgE, IgM, IgD, IgA and IgY), class (e.g., IgG1, IgG2, IgG3, IgG4, IgA1 and IgA2), subclass or modified version thereof (e.g. IgG1 LALA). The antibodies can be of any species, chimeric, humanized or human.

The terms "heavy chain variable region CDR1" and "H-CDR1" are used interchangeably, as are the terms "heavy chain variable region CDR2" and "H-CDR2", the terms "heavy chain variable region CDR3" and "H-CDR3", the terms "light chain variable region CDR1" and "L-CDR1"; the terms "light chain variable region CDR2" and "L-CDR2" and the terms "light chain variable region CDR3" and "L-CDR3" antibody fragment.

Antigen binding can be performed by "fragments" "antibody fragments" "antigen binding fragments" of an intact antibody. Herein, both terms are used interchangeably. Examples of binding fragments encompassed within the term "antibody fragment" of an antibody include a Fab fragment, a monovalent fragment consisting of the VL, VH, CL and CH1 domains; a F(ab)2 fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a single domain antibody (dAb) fragment (Ward et al., (1989) Nature 341:544-546), which consists of a VH domain; and an isolated complementary determining region (CDR).

A "single chain Fragment (scFv)" is a single protein chain in which the VL and VH regions pair to form monovalent molecules (known as single chain Fv (scFv); see, e.g., Bird et al., (1988) Science 242:423-426; and Huston et al., (1988) Proc. Natl. Acad. Sci. 85:5879-5883). Although the two domains VL and VH are coded for by separate genes, they can be joined, using recombinant methods, by an artificial peptide linker that enables them to be made as a single protein chain. Such single chain antibodies include one or more antigen binding moieties. These antibody fragments are obtained using conventional techniques known to those of skill in the art, and the fragments are screened for utility in the same manner as are intact antibodies. In certain aspects the present disclosure provides antibody fragments, wherein said antibody fragment is selected from the group consisting of a Fab, F(ab2)', F(ab)2' and scFV.

In certain aspects the present disclosure provides antibodies or antibody fragments, wherein said antibody or antibody fragment is bispecific. In certain aspects said antibody or antibody fragment is a bispecific antibody-derived scaffold wherein said bispecific antibody-derived scaffold is selected from the group consisting of a bispecific-scFv, a tetravalent bispecific antibody, a cross-linked Fab or a bispecific IgG.

In certain aspects the present disclosure provides to an antibody or antibody fragment, wherein the antibody or antibody fragment is selected from the group consisting of single domain antibodies, maxibodies, minibodies, intrabodies, diabodies, triabodies, tetrabodies, v-NAR, camelid antibodies, ankyrins, domain antibodies, lipocalins, small modular immuno-pharmaceuticals, maxybodies, Protein A and affilins.

The terms "monoclonal antibody" as used herein refer to a preparation of antibody molecules of single molecular composition. A monoclonal antibody composition displays a unique binding site having a unique binding specificity and affinity for particular epitopes. In certain aspects the present disclosure provides monoclonal antibodies or antibody fragments which specifically bind to M-CSF. In certain aspects the present disclosure provides polyclonal antibodies or antibody fragments which specifically bind to M-CSF.

In certain aspect the disclosure provides an isolated antibody or antibody fragment which is cross-reactive to cynomolgus M-CSF. In certain aspect the disclosure provides an isolated antibody or antibody fragment which is cross-reactive to mouse M-CSF. In certain aspect the disclosure provides an isolated antibody or antibody fragment which is cross-reactive to rat M-CSF. In certain aspect the disclosure provides an isolated antibody or antibody fragment which is cross-reactive to cynomolgus and/or mouse and/or rat M-CSF.

The term "human antibody", as used herein, is intended to include antibodies having variable regions in which both the framework and CDR regions are derived from sequences of human origin. As used herein, a human antibody comprises heavy or light chain variable regions or full length heavy or light chains. In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Thereby said human antibody can be obtained from technology platforms which comprise antibodies derived from human germline genes either generated by PCR-amplification of VH/VL repertoire isolated from B-cells or are generated synthetically. Technology platforms include library based approaches comprising human immunoglobulin genes displayed on phage, ribosome or yeast. Respective display technologies are standard in the scientific community. Furthermore immunization of a transgenic mouse carrying human immunoglobulin repertoire is another approach to generate human antibodies against an antigen of interest. Antibodies or fragments thereof selected from an antibody library based on the MorphoSys HuCAL® concept (Knappik et al., (2000) J Mol Biol 296:57-86) are considered as fully human.

A "humanized" antibody is an antibody that retains the reactivity of a non-human antibody while being less immunogenic in humans. This can be achieved, for instance, by retaining the non-human CDR regions and replacing the remaining parts of the antibody with their human counterparts (i.e., the constant region as well as the framework portions of the variable region). See, e.g., Morrison et al (1994) Proc. Natl. Acad. Sci. USA, 81:6851-6855; Morrison and Oi (1988) Adv. Immunol., 44:65-92; Verhoeyen et al. (1988) Science, 239:1534-1536; Padlan, Molec (1991) Immun., 28:489-498; and Padlan, Molec (1994) Immun., 31:169-217. Other examples of human engineering technology include, but are not limited to Xoma technology disclosed in U.S. Pat. No. 5,766,886.

The term "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. For example, a mouse antibody can be modified by replacing its constant region with the constant region from a human immunoglobulin. Due to the replacement with a human constant region, the chimeric antibody can retain its specificity in recognizing the antigen while having reduced antigenicity in human as compared to the original mouse antibody.

In certain aspects the present disclosure provides human antibodies and antibody fragments which specifically bind to M-CSF. In certain aspects the present disclosure provides humanized antibodies and antibody fragments which specifically bind to M-CSF. In certain aspects the present disclosure provides chimeric antibodies and antibody fragments which specifically bind to M-CSF. In certain aspects the present disclosure provides antibodies comprising a human heavy chain constant region and a human light chain constant region.

The term "isotype" refers to the antibody class (e.g., IgM, IgE, IgG such as IgG1 or IgG4) that is provided by the heavy chain constant region genes. Isotype also includes modified versions of one of these classes, where modifications have been made to alter the Fc function, for example, to enhance or reduce effector functions or binding to Fc receptors. For example IgG1 LALA is a modified version of the IgG isotype having significantly reduced effector functions. Specific substitutions of amino acids reduced the binding affinity for Fc gamma RI receptor as compared with unmodified antibody. IgG1 LALA is described in U.S. Ser. No. 08/479,752 (SCOTGEN BIOPHARMACEUTICALS INC.) which is incorporated by reference in its entirety. In certain embodiments of the present disclosure the antigen-binding moieties of are antibodies and are of the type IgG, IgM, IgA, IGE or IgD. In specific embodiments the antibodies are of the type IgG. In certain embodiments of the present disclosure the antibodies are of the subtype IgG1, IgG2, IgG3 or IgG4. In specific embodiments the antibodies are of the subtype IgG1 or IgG4. In other specific embodiments the antibodies are of the subtype IgG1 or IgG1 LALA.

In certain specific embodiments of the present disclosure, the antibodies are of a silent isotype. The term "silent" isotype refers to any immunoglobulin with a diminished effector function. Therefore, in certain embodiments of the present disclosure the antibody is of a IgG1 subtype which has an effector function which is diminished compared to the wild type IgG1 subtype. Certain mutations are particularly suited to achieve a diminished effector function. For example the IgG1 LALA subtype is a typical silent isotype. Other silent versions of the IgG1 isotype might be used with the antibodies of the present disclosure as well. One specifically preferred example is the IgG1 isotype harboring a D265A mutation. In this IgG1 version the amino acid aspartic acid at position 265 (numbering according to the EU index; see www with the extension imgt.org/IMGTScientificChart/Numbering/Hu_IGHGnber.html of the world wide web) is exchanged for an alanine residue. Therefore, in certain aspects the antibodies of the present disclosure are antibodies of a silent IgG1 subtype. In alternative aspect the antibodies of the present disclosure are antibodies of a mutant IgG1 subtype which has decreased effector as compared to the wildtype IgG1 subtype. In alternative aspects the antibodies of the present disclosure are antibodies of the IgG1 subtype carrying a D265A mutation. In alternative aspect the antibodies of the present disclosure are antibodies of the IgG1 subtype wherein the aspartic acid at position 265 is exchanged for an alanine residue. In alternative aspect the antibodies of the present disclosure are antibodies in which the aspartic acid residue at position 265 (numbering according to the EU index) is exchanged for an alanine residue. The subtypes IgG2 and IgG4 are also known as silent isotypes.

The term "affinity" as used herein refers to the strength of interaction between an antigen binding moiety, like e.g. a monoclonal antibody and an antigen at single antigenic sites. Within each antigenic site, the variable region of the antibody "arm" interacts through weak non-covalent forces with antigen at numerous sites; the more interactions, the stronger the affinity.

The term "specifically binds [to]" an antigen refers to a binding reaction that is determinable in the presence of an antigen in a heterogeneous population of proteins and other biologics. Thereby the phrases "recognizing an antigen" and "specific for an antigen" are used interchangeably herein with the term "binds specifically to an antigen". Specific binding of an antigen binding moiety, like e.g. a monoclonal antibody, to an antigen can be determined by various established methods known in the art and include ELISA, FACS, Western Blot, Immuno Blot, MSD, BIAcore and SET. In the present disclosure an antigen binding moiety is deemed to be specific for an antigen if the antigen binding moiety is demonstrated to be able to bind to a specific antigen at least 2-fold, at least 3-fold, at least 4-fold, at least 5-fold, at least 6-fold, at least 7-fold, at least 8-fold, at least 9-fold, at least 10-fold, at least 20-fold, at least 50-fold, at least 100-fold, at least 500-fold, at least 1000-fold over background. Thereby the background is determined by an antigen binding moiety which is known to be unspecific for the selected antigens or by comparison to binding to an unrelated antigen. The antigen for the inventive antibodies and antibody fragments of the present invention is M-CSF.

The full-length human M-CSF precursor (also known as CSF-1 or macrophage colony-stimulating-factor) has a length of 554 amino acids. The amino acid sequence of human M-CSF precursor is shown in SEQ ID NO:1 (source: Uniprot, human M-CSF P09603).

SEQ ID NO: 1 (full-length human M-CSF precursor):
MTAPGAAGRCPPTTWLGSLLLLVCLLASRSITEEVSEYCSHMIGSGHLQ

SLQRLIDSQMETSCQITFEFVDQEQLKDPVCYLKKAFLLVQDIMEDTM

RFRDNTPNAIAIVQLQELSLRLKSCFTKDYEEHDKACVRTFYETPLQLL

EKVKNVFNETKNLLDKDWNIFSKNCNNSFAECSSQDVVTKPDCNCLYPK

AIPSSDPASVSPHQPLAPSMAPVAGLTWEDSEGTEGSSLLPGEQPLHTV

DPGSAKQRPPRSTCQSFEPPETPVVKDSTIGGSPQPRPSVGAFNPGMED

ILDSAMGTNWVPEEASGEASEIPVPQGTELSPSRPGGGSMQTEPARPSN

FLSASSPLPASAKGQQPADVTGTALPRVGPVRPTGQDWNHTPQKTDHPS

ALLRDPPEPGSPRISSLRPQGLSNPSTLSAQPQLSRSHSSGSVLPLGEL

EGRRSTRDRRSPAEPEGGPASEGAARPLPRFNSVPLTDTGHERQSEGSF

SPQLQESVFHLLVPSVILVLLAVGGLLFYRWRRRSHQEPQRADSPLEQP

EGSPLTQDDRQVELPV

Three different extracellular isoforms of M-CSF are expressed as a consequence of splicing and post-translational modifications: secreted glycosylated M-CSF ("sgM-CSF"), secreted proteoglycan M-CSF ("spM-CSF"), and cell-surface M-CSF ("csM-CSF").

The most predominant isoform in human serum is sgM-CSF which is generated by cleavage of the M-CSF precursor at position 255. The amino acid sequence of human sgM-CSF is shown in SEQ ID NO:2.

```
SEQ ID NO: 2 (human secreted glycosylated M-CSF
(fragment 33-255 of SEQ ID NO: 1)):
EEVSEYCSHMIGSGHLQSLQRLIDSQMETSCQITFEFVDQEQLKDPVCYL

KKAFLLVQDIMEDTMRFRDNTPNAIAIVQLQELSLRLKSCFTKDYEEHDK

ACVRTFYETPLQLLEKVKNVFNETKNLLDKDWNIFSKNCNNSFAECSSQD

VVTKPDCNCLYPKAIPSSDPASVSPHQPLAPSMAPVAGLTWEDSEGTEGS

SLLPGEQPLHTVDPGSAKQRPPR
```

Human secreted proteoglycan M-CSF has a length of 456 amino acids. The amino acid sequence of spM-CSF is shown in SEQ ID NO:3.

```
SEQ ID NO: 3 (human secreted proteoglycan M-CSF)
EEVSEYCSHMIGSGHLQSLQRLIDSQMETSCQITFEFVDQEQLKDPVCY

LKKAFLLVQDIMEDTMRFRDNTPNAIAIVQLQELSLRLKSCFTKDYEEH

DKACVRTFYETPLQLLEKVKNVFNETKNLLDKDWNIFSKNCNNSFAECS

SQDVVTKPDCNCLYPKAIPSSDPASVSPHQPLAPSMAPVAGLIWEDSEG

TEGSSLLPGEQPLHTVDPGSAKQRPPRSTCQSFEPPETPVVKDSTIGGS

PQPRPSVGAFNPGMEDILDSAMGTNWVPEEASGEASEIPVPQGTELSPS

RPGGGSMQTEPARPSNFLSASSPLPASAKGQQPADVTGTALPRVGPVRP

TGQDWNHTPQKTDHPSALLRDPPEPGSPRISSLRPQGLSNPSTLSAQPQ

LSRSHSSGSVLPLGELEGRRSTRDRRSPAEPEGGPASEGAARPLPRFNS

VPLTDTGHERQSEGS
```

The human cell-surface M-CSF is generated by alternative splicing and has a length of 256 amino acids. The amino acid sequence of csM-CSF is shown in SEQ ID NO:4.

```
SEQ ID NO: 4 (human cell surface M-CSF)
EEVSEYCSHMIGSGHLQSLQRLIDSQMETSCQITFEFVDQEQLKDPVCYL

KKAFLLVQDIMEDTMRFRDNTPNAIAIVQLQELSLRLKSCFTKDYEEHDK

ACVRTFYETPLQLLEKVKNVFNETKNLLDKDWNIFSKNCNNSFAECSSQG

HERQSEGSSSPQLQESVFHLLVPSVILVLLAVGGLLFYRWRRRSHQEPQR

ADSPLEQPEGSPLTQDDRQVELPV
```

All 3 isoforms of M-CSF can bind to the M-CSF receptor and are biologically active. The three isoforms have in common the N-terminal receptor-binding domain (rbdM-CSF), the amino acid sequence of which is shown in SEQ ID NO:5.

```
SEQ ID NO: 5 (human receptor binding domain
M-CSF (fragment 33-190))
EEVSEYCSHMIGSGHLQSLQRLIDSQMETSCQITFEFVDQEQLKDPVCYL

KKAFLLVQDIMEDTMRFRDNTPNAIAIVQLQELSLRLKSCFTKDYEEHDK

ACVRTFYETPLQLLEKVKNVFNETKNLLDKDWNIFSKNCNNSFAECSSQD

VVTKPDCN
```

The antibodies and antibody fragments of the present disclosure also bind to M-CSF of cynomolgus monkeys (*Macaca fascicularis*), which are frequently used in the laboratory for pre-clinical studies. The nucleic acid molecule encoding secreted glycoprotein M-CSF of cynomolgus was cloned by standard PCR techniques from cynomolgus cDNA prepared from breast or pancreas tissues. The sequence of cynomolgus sgM-CSF is shown in SEQ ID NO:6.

```
SEQ ID NO: 6 (cynomolgus sgM-CSF):
EEVSEYCSHMIGSGHLQSLQRLIDSQMETSCQITFEFVDQEQLKDPVCYL

KKAFLLVQDIMEDTMRFRDNTPNAIAIVQLQELSLRLKSCFTKDYEEHDK

ACVRTFYETPLQLLEKVKNVFNETKNLLDKDWNIFSKNCNNSFAECSSQD

VVTKPDCNCLYPKAIPSSDPASVSPHQPLAPSMAPMAGLTWDDSEGTEGS

SLLPGEQPLHTVDPGSAKQRPPR
```

Human M-CSF receptor (also known as M-CSFR or CSF1R) has a length of 972 amino acids. The amino acid sequence of human M-CSFR is shown in SEQ ID NO:7 (source: Uniprot, human M-CSFR P07333):

```
SEQ ID NO: 7 (human M-CSFR):
MGPGVLLLLLLVATAWHGQGIPVIEPSVPELVVKPGATVTLRCVGNGSVE

WDGPPSPHWTLYSDGSSSILSTNNATFQNTGTYRCTEPGDPLGGSAAIH

LYVKDPARPWNVLAQEVVVFEDQDALLPCLLTDPVLEAGVSLVRVRGRP

LMRHTNYSFSPWHGFTIHRAKFIQSQDYQCSALMGGRKVMSISIRLKVQ

KVIPGPPALTLVPAELVRIRGEAAQIVCSASSVDVNFDVFLQHNNTKLA

IPQQSDFHNNRYQKVLTLNLDQVDFQHAGNYSCVASNVQGKHSTSMFFR

VVESAYLNLSSEQNLIQEVTVGEGLNLKVMVEAYPGLQGFNWTYLGPFS

DHQPEPKLANATTKDTYRHTFTLSLPRLKPSEAGRYSFLARNPGGWRAL

TFELTLRYPPEVSVIWTFINGSGTLLCAASGYPQPNVTWLQCSGHTDRC

DEAQVLQVVVDDPYPEVLSQEPFHKVTVQSLLTVETLEHNQTYECRAHN

SVGSGSWAFIPISAGAHTHPPDEFLFTPVVVACMSIMALLLLLLLLLLY

KYKQKPKYQVRWKIIESYEGNSYTFIDPTQLPYNEKWEFPRNNLQFGKT

LGAGAFGKVVEATAFGLGKEDAVLKVAVKMLKSTAHADEKEALMSELKI

MSHLGQHENIVNLLGACTHGGPVLVITEYCCYGDLLNFLRRKAEAMLGP

SLSPGQDPEGGVDYKNIHLEKKYVRRDSGFSSQGVDTYVEMRPVSTSSN

DSFSEQDLDKEDGRPLELRDLLHFSSQVAQGMAFLASKNCIHRDVAARN

VLLTNGHVAKIGDFGLARDIMNDSNYIVKGNARLPVKWMAPESIFDCVY

TVQSDVWSYGILLWEIFSLGLNPYPGILVNSKFYKLVKDGYQMAQPAFA

PKNIYSIMQACWALEPTHRPTFQQICSFLQEQAQEDRRERDYTNLPSSS

RSGGSGSSSSELEEESSSEHLTCCEQGDIAQPLLQPNNYQFC
```

The antibodies and antibody fragments of the present disclosure also inhibit the binding cynomolgus M-CSF to the cynomolgus M-CSF receptor.

In certain aspects the present disclosure relates to an isolated antibody or antibody fragment which is directed against or specifically binds to the human M-CSF. In alternative aspects the present disclosure relates to an isolated antibody or antibody fragment which is directed against or specifically binds to the polypeptide encoded by SEQ ID NO:1.

In certain aspects the present disclosure relates to an isolated antibody or antibody fragment which is directed against or specifically binds to the cynomolgus M-CSF. In alternative aspects the present disclosure relates to an isolated antibody or antibody fragment which is directed against or specifically binds to the polypeptide encoded by SEQ ID NO:6.

In certain aspects the present disclosure relates to an isolated antibody or antibody fragment which is directed against or specifically binds to the human M-CSF and which inhibits binding of human M-CSF to the human M-CSF receptor. In alternative aspects the present disclosure relates to an isolated antibody or antibody fragment which is directed against or specifically binds to the polypeptide encoded by SEQ ID NO:1 and which inhibits binding of the polypeptide encoded by SEQ ID NO:1 to the polypeptide encoded by SEQ ID NO:7.

In certain aspects the present disclosure relates to an isolated antibody or antibody fragment which is directed against or specifically binds to the cynomolgus M-CSF and which inhibits binding of cynomolgus M-CSF to the cynomolgus M-CSF receptor. In alternative aspects the present disclosure relates to an isolated antibody or antibody fragment which is directed against or specifically binds to the polypeptide encoded by SEQ ID NO:6 and which inhibits binding of the polypeptide encoded by SEQ ID NO: 6 to the polypeptide encoded by SEQ ID NO:7. In alternative aspects the present disclosure relates to an isolated antibody or antibody fragment which is directed against or specifically binds to the polypeptide encoded by SEQ ID NO:6 and which inhibits binding of the polypeptide encoded by SEQ ID NO:6 to the cynomolgus M-CSF receptor.

In certain aspects the present disclosure relates to an isolated antibody or antibody fragment which binds to secreted glycosylated M-CSF, secreted proteoglycan M-CSF and cell-surface M-CSF. In certain aspects the present disclosure relates to an isolated antibody or antibody fragment which binds to all isoforms of human M-CSF. In certain aspects the present disclosure relates to an isolated antibody or antibody fragment which binds to a polypeptide encoded by SEQ ID NO:2, a polypeptide encoded by SEQ ID NO:3 and a polypeptide encoded by SEQ ID NO:4.

In certain aspects the present disclosure relates to an isolated antibody or antibody fragment which binds to the N-terminal receptor-binding domain of M-CSF. In certain aspects the present disclosure relates to an isolated antibody or antibody fragment which binds to a polypeptide encoded by SEQ ID NO:5.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al. (1991) Nucleic Acid Res. 19:5081; Ohtsuka et al. (1985) J. Biol. Chem. 260: 2605-2608; and Rossolini et al. (1994) Mol. Cell. Probes 8:91-98).

In certain aspects the present disclosure provides a nucleic acid encoding an antibody or antibody fragment according to the present disclosure which specifically binds to M-CSF. In certain aspects the present disclosure provides a nucleic acid encoding an antibody or antibody fragment of Table 1. In certain aspects the present disclosure provides a nucleic acid encoding an antibody or antibody fragment of Table 2.

In certain aspects the present disclosure provides a vector comprising a nucleic acid encoding an antibody or antibody fragment according to the present disclosure which specifically binds to M-CSF. In certain aspects the present disclosure provides a vector comprising a nucleic acid encoding an antibody or antibody fragment of Table 1. In certain aspects the present disclosure provides a vector comprising a nucleic acid encoding an antibody or antibody fragment of Table 2.

In certain aspects the present disclosure provides a host cell comprising a vector comprising a nucleic acid encoding an antibody or antibody fragment of the present disclosure. In certain aspects the present disclosure provides a host cell comprising a nucleic acid encoding an antibody or antibody fragment of the present disclosure.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "vector" refers to a polynucleotide molecule capable of transporting another polynucleotide to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the disclosure is intended to include such other forms of expression vectors, such as viral vectors (e.g., replication defective retroviruses, adenoviruses and adeno-associated viruses), which serve equivalent functions.

In certain aspects the present disclosure provides isolated antibodies or antibody fragment, which specifically binds to M-CSF and which inhibits binding of M-CSF to the M-CSF receptor with an IC50 of 10 pM or less. In other aspect said isolated antibodies or antibody fragment inhibits binding of M-CSF to the M-CSF receptor with an IC50 of 20 pM or less, an IC50 of 5.5 pM or less or an IC50 of 5 pM or less.

In certain aspects the present disclosure provides isolated antibody or antibody fragment, which specifically binds to M-CSF and wherein said isolated antibody or antibody fragment is able to inhibit the binding of M-CSF to the M-CSF receptor with an IC50 of 10 pM or less in a receptor binding inhibition assay comprising M-CSF at a final concentration of 12.5 pM.

In certain aspects the present disclosure provides isolated antibody or antibody fragment, which specifically binds to M-CSF and wherein said isolated antibody or antibody fragment is able to inhibit the binding of M-CSF to the M-CSF receptor with an IC50 of 10 pM or less in a receptor binding inhibition assay comprising M-CSF at a final concentration of 0.66 ng/ml and M-CSF receptor at a final concentration of 2 µg/ml.

In certain aspects the present disclosure provides isolated antibody or antibody fragment, which specifically binds to M-CSF and wherein said isolated antibody or antibody fragment is able to inhibit the binding of M-CSF to the M-CSF receptor with an IC50 of 10 pM or less in a receptor binding inhibition assay as described in Example 5.

In certain aspects the present disclosure provides isolated antibodies or antibody fragment, which specifically binds to M-CSF and which inhibits binding of M-CSF to the M-CSF receptor with an IC50 which is at least twice as low as the IC50 of any one of the prior art antibodies HeRX1-10G1 and 8.10.3F. In alternative said isolated antibodies or antibody fragment inhibits binding of M-CSF to the M-CSF receptor with an IC50 which is at least three times as low as the IC50 of any one of the prior art antibodies HeRX1-10G1 and 8.10.3F.

In certain aspects the present disclosure provides isolated antibodies or antibody fragment, which specifically binds to M-CSF with an EC50 of 10 pM or less as determined in a FACS assay. In alternative aspects said isolated antibodies or antibody fragments specifically bind to M-CSF with an EC50 of 15 pM or less as determined in a FACS assay or with an EC50 of 5 pM or less as determined in a FACS assay.

In certain aspects the present disclosure provides isolated antibodies or antibody fragment, which specifically binds to M-CSF with an EC50 which is at least twice as low as the EC50 of any one of the prior art antibodies HeRX1-10G1 or 8.10.3F as determined in a FACS assay.

In certain aspects the present disclosure provides isolated antibodies or antibody fragment, which specifically binds to M-CSF and which inhibits M-CSF induced proliferation with an IC50 of 10 pM or less. In alternative aspects said isolated antibodies or antibody fragments inhibits M-CSF induced proliferation with an IC50 of 20 pM or less, with an IC50 of 15 pM or less or with an IC50 of 5 pM or less.

In certain aspects the present disclosure provides isolated antibodies or antibody fragment, which specifically binds to M-CSF and which inhibits M-CSF induced proliferation with an IC50 which is at least twice as low as the IC50 of any one of the prior art antibodies HeRX1-10G1 or 8.10.3F.

The term "KD", as used herein, refers to the dissociation constant, which is obtained from the ratio of Kd to Ka (i.e. Kd/Ka) and is expressed as a molar concentration (M). KD values for antigen binding moieties like e.g. monoclonal antibodies can be determined using methods well established in the art. Methods for determining the KD of an antigen binding moiety like e.g. a monoclonal antibody are SET (soluble equilibrium titration) or surface plasmon resonance using a biosensor system such as a Biacore® system. Antibodies of the present disclosure typically have a dissociation rate constant (KD) (koff/kon) of less than $5\times10^{-2}$M, less than $10^{-2}$M, less than $5\times10^{-3}$M, less than $10^{-3}$M, less than $5\times10^{-4}$M, less than $10^{-4}$M, less than $5\times10^{-5}$M, less than $10^{-5}$M, less than $5\times10^{-6}$M, less than $10^{-6}$M, less than $5\times10^{-7}$M, less than $10^{-7}$M, less than $5\times10^{-8}$M, less than $10^{-8}$M, less than $5\times10^{-9}$M, less than $10^{-9}$M, less than $5\times10^{-10}$M, less than 10-10M, less than $5\times10$-11M, less than $10^{-11}$M, less than $5\times10^{-12}$M, less than $10^{-12}$M, less than $5\times10^{-13}$M, less than $10^{-13}$M, less than $5\times10^{-14}$M, less than $10^{-14}$M, less than $5\times10^{-15}$M, or less than $10^{-15}$M or lower.

In certain aspect, the present disclosure provides an isolated antibody or antibody fragment specific for M-CSF, wherein said antibody or antibody fragment binds to a M-CSF, with a dissociation constant (KD) of less than $1\times10^7$ $M^{-1}$, $10^8$ $M^{-1}$, $10^9$ $M^{-1}$, $10^{10}$ $M^{-1}$, $10^{11}$ $M^{-1}$, $10^{12}$ $M^{-1}$ or $10^{13}$ $M^{-1}$.

The term "EC50", as used herein, refers to the concentration of an antibody or an antibody fragment which induces a response in an assay half way between the baseline and maximum. It therefore represents the antibody concentration at which 50% of the maximal effect is observed.

The term "IC50", as used herein, refers to the concentration of an inhibitor (e.g. an antibody or antibody fragment) that inhibits a response in an assay half way between the maximal response and the baseline. It represents the antibody concentration that reduces a given response by 50%.

In certain aspects the present disclosure provides isolated antibodies and antibody fragments, wherein said antibody or antibody fragment comprises the HCDR1 region of SEQ ID NO:8, the HCDR2 region of SEQ ID NO:9, the HCDR3 region of SEQ ID NO:10, the LCDR1 region of SEQ ID NO:11, the LCDR2 region of SEQ ID NO:12 and the LCDR3 region of SEQ ID NO:13.

In certain aspects the present disclosure provides isolated antibodies and antibody fragments, wherein said antibody or antibody fragment comprises the HCDR1 region of SEQ ID NO:18, the HCDR2 region of SEQ ID NO:19, the HCDR3 region of SEQ ID NO:20, the LCDR1 region of SEQ ID NO:21, the LCDR2 region of SEQ ID NO:22 and the LCDR3 region of SEQ ID NO:23.

In certain aspects the present disclosure provides isolated antibodies and antibody fragments, wherein said antibody or antibody fragment comprises the HCDR1 region of SEQ ID NO:28, the HCDR2 region of SEQ ID NO:29, the HCDR3 region of SEQ ID NO:30, the LCDR1 region of SEQ ID NO:31, the LCDR2 region of SEQ ID NO:32 and the LCDR3 region of SEQ ID NO:33.

In certain aspects the present disclosure provides isolated antibodies and antibody fragments, wherein said antibody or antibody fragment comprises the HCDR1 region of SEQ ID NO:38, the HCDR2 region of SEQ ID NO:39, the HCDR3 region of SEQ ID NO:40, the LCDR1 region of SEQ ID NO:41, the LCDR2 region of SEQ ID NO:42 and the LCDR3 region of SEQ ID NO:43.

In certain aspects the present disclosure provides isolated antibodies and antibody fragments, wherein said antibody or antibody fragment comprises the HCDR1 region of SEQ ID NO:48, the HCDR2 region of SEQ ID NO:49, the HCDR3 region of SEQ ID NO:50, the LCDR1 region of SEQ ID NO:51, the LCDR2 region of SEQ ID NO:52 and the LCDR3 region of SEQ ID NO:53.

In certain aspects the present disclosure provides isolated antibodies and antibody fragments, wherein said antibody or antibody fragment comprises the HCDR1 region of SEQ ID NO:58, the HCDR2 region of SEQ ID NO:59, the HCDR3 region of SEQ ID NO:60, the LCDR1 region of SEQ ID NO:61, the LCDR2 region of SEQ ID NO:62 and the LCDR3 region of SEQ ID NO:63.

In certain aspects the present disclosure provides isolated antibodies and antibody fragments, wherein said antibody or antibody fragment comprises the HCDR1 region of SEQ ID NO:68, the HCDR2 region of SEQ ID NO:69, the HCDR3 region of SEQ ID NO:70, the LCDR1 region of SEQ ID NO:71, the LCDR2 region of SEQ ID NO:72 and the LCDR3 region of SEQ ID NO: 73.

In certain aspects the present disclosure provides isolated antibodies and antibody fragments, wherein said antibody or antibody fragment comprises the HCDR1 region of SEQ ID NO: 78, the HCDR2 region of SEQ ID NO:79, the HCDR3 region of SEQ ID NO:80, the LCDR1 region of SEQ ID NO:81, the LCDR2 region of SEQ ID NO:82 and the LCDR3 region of SEQ ID NO:83.

In certain aspects the present disclosure provides isolated antibodies and antibody fragments, wherein said antibody or antibody fragment comprises the HCDR1 region of SEQ ID NO:88, the HCDR2 region of SEQ ID NO:89, the HCDR3 region of SEQ ID NO:90, the LCDR1 region of SEQ ID NO:91, the LCDR2 region of SEQ ID NO:92 and the LCDR3 region of SEQ ID NO:93.

In certain aspects the present disclosure provides isolated antibodies and antibody fragments, wherein said antibody or antibody fragment comprises the HCDR1 region of SEQ ID NO:98, the HCDR2 region of SEQ ID NO:99, the HCDR3 region of SEQ ID NO:100, the LCDR1 region of SEQ ID NO:101, the LCDR2 region of SEQ ID NO:102 and the LCDR3 region of SEQ ID NO: 103.

In certain aspects the present disclosure provides isolated antibodies and antibody fragments, wherein said antibody or antibody fragment comprises the HCDR1 region of SEQ ID NO:108, the HCDR2 region of SEQ ID NO:109, the HCDR3 region of SEQ ID NO:110, the LCDR1 region of SEQ ID NO:111, the LCDR2 region of SEQ ID NO:112 and the LCDR3 region of SEQ ID NO: 113.

In certain aspects the present disclosure provides isolated antibodies and antibody fragments, wherein said antibody or antibody fragment comprises the variable heavy region of SEQ ID NO:14 and the variable light region of SEQ ID NO:15.

In certain aspects the present disclosure provides isolated antibodies and antibody fragments, wherein said antibody or antibody fragment comprises the variable heavy region of SEQ ID NO:24 and the variable light region of SEQ ID NO:25.

In certain aspects the present disclosure provides isolated antibodies and antibody fragments, wherein said antibody or antibody fragment comprises the variable heavy region of SEQ ID NO:34 and the variable light region of SEQ ID NO:35.

In certain aspects the present disclosure provides isolated antibodies and antibody fragments, wherein said antibody or antibody fragment comprises the variable heavy region of SEQ ID NO:44 and the variable light region of SEQ ID NO:45.

In certain aspects the present disclosure provides isolated antibodies and antibody fragments, wherein said antibody or antibody fragment comprises the variable heavy region of SEQ ID NO:54 and the variable light region of SEQ ID NO:55.

In certain aspects the present disclosure provides isolated antibodies and antibody fragments, wherein said antibody or antibody fragment comprises the variable heavy region of SEQ ID NO:64 and the variable light region of SEQ ID NO:65.

In certain aspects the present disclosure provides isolated antibodies and antibody fragments, wherein said antibody or antibody fragment comprises the variable heavy region of SEQ ID NO:74 and the variable light region of SEQ ID NO:75.

In certain aspects the present disclosure provides isolated antibodies and antibody fragments, wherein said antibody or antibody fragment comprises the variable heavy region of SEQ ID NO:84 and the variable light region of SEQ ID NO:85.

In certain aspects the present disclosure provides isolated antibodies and antibody fragments, wherein said antibody or antibody fragment comprises the variable heavy region of SEQ ID NO:94 and the variable light region of SEQ ID NO:95.

In certain aspects the present disclosure provides isolated antibodies and antibody fragments, wherein said antibody or antibody fragment comprises the variable heavy region of SEQ ID NO:104 and the variable light region of SEQ ID NO:105.

In certain aspects the present disclosure provides isolated antibodies and antibody fragments, wherein said antibody or antibody fragment comprises the variable heavy region of SEQ ID NO:114 and the variable light region of SEQ ID NO:115.

In certain aspects the present disclosure provides isolated antibodies and antibody fragments which compete with the antibodies specifically disclosed herein for binding to M-CSF. In other aspects the present disclosure provides isolated antibodies and antibody fragments which compete with the antibodies specifically disclosed herein for binding to human M-CSF. In other aspects the present disclosure provides isolated antibodies and antibody fragments which compete with the antibodies specifically disclosed herein for binding to a polypeptide encoded by SEQ ID NO: 1.

The term "competes" or "cross-competes" refers to an antibody or antibody fragment which shares the ability to bind to a specific region of an antigen. In the present disclosure an antibody or antibody fragment that is "cross-competitive" has the ability to interfere with the binding of another antibody or antibody fragment for M-CSF in a standard competitive binding assay. Such an antibody may, according to non-limiting theory, bind to the same or a related or nearby (e.g., a structurally similar or spatially proximal) epitope on M-CSF. Cross-competition studies to find antibodies that competitively bind with one another, e.g., the antibodies compete for binding to the antigen can be performed. The ability or extent to which an antibody or antibody fragment is able to interfere with the binding of another antibody or antibody fragment to M-CSF and therefore whether it can be said to cross-compete according to the invention, can be determined using standard competition binding assays. Cross-competition is present if antibody A reduces binding of antibody B at least by 50%, at least by 60%, specifically at least by 70% and more specifically at least by 80% and vice versa in comparison to the positive control which lacks one of said antibodies. As the skilled artisan appreciates competition may be assessed in different assay set-ups. One suitable assay involves the use of the Biacore technology (e.g. by using the BIAcore 3000 instrument (Biacore, Uppsala, Sweden)), which can measure the extent of interactions using surface plasmon resonance technology. Another assay for measuring cross-competition uses an ELISA-based approach. Furthermore, a high throughput process for "binning" antibodies based upon their cross-competition is described in International Patent Application No. WO2003/48731. Cross-competition is present if the antibody under investigation reduces the binding of one of the antibodies by 60% or more, specifically by 70% or more and more specifically by 80% or more and if one of the antibodies reduces the binding of said antibody to M-CSF by 60% or more, specifically by 70% or more and more specifically by 80% or more.

In certain aspect the present disclosure pertains to an antibody or antibody fragment specific for M-CSF, that cross-competes with an antibody described in Table 1. In certain aspect the present disclosure pertains to an antibody or antibody fragment specific for M-CSF, that cross-competes with an antibody described in Table 2.

In a certain embodiment, the antibody or antibody fragment that cross-competes with an antibody described in Table 1 reduces the binding of one of the antibodies described in Table 1 to M-CSF, by at least 50%, 60%, 70%, 80% or 90% in an ELISA-based cross-competition assay. In a certain embodiment, the antibody or antibody fragment that cross-competes with an antibody described in Table 2 reduces the binding of one of the antibodies described in Table 2 to M-CSF, by at least 50%, 60%, 70%, 80% or 90% in an ELISA-based cross-competition assay.

In certain aspects the present disclosure provides isolated antibodies and antibody fragments which bind to the same epitope like the antibodies specifically disclosed herein. In certain aspects the present disclosure provides isolated antibodies and antibody fragments which bind to the same epitope like the antibodies described in Table 1. In certain aspects the present disclosure provides isolated antibodies and antibody fragments which bind to the same epitope like the antibodies described in Table 2.

The term "epitope" includes any proteinacious region which is specifically recognized by an immunoglobulin or T-cell receptor or otherwise interacts with a molecule. Generally epitopes are of chemically active surface groupings of molecules such as amino acids or carbohydrate or sugar side chains and generally may have specific three-dimensional structural characteristics, as well as specific charge characteristics. As will be appreciated by one of skill in the art, practically anything to which an antibody can specifically bind could be an epitope.

In certain aspect, the present disclosure pertains to an antibody or antibody fragment specific for M-CSF which interacts with (e.g., by binding, stabilizing, spatial distribution) the same epitope as an antibody described in Table 1. In certain aspect, the disclosure pertains to an antibody or antibody fragment specific for M-CSF which interacts with (e.g., by binding, stabilizing, spatial distribution) the same epitope as an antibody described in Table 2.

In certain aspect, the present disclosure pertains to an antibody or antibody fragment disclosed herein for use in medicine.

In certain aspect the disclosure provides to a pharmaceutical composition comprising an isolated antibody or antibody fragment which is directed against or binds to M-CSF, and a pharmaceutically acceptable carrier. In certain aspects, the present invention provides a pharmaceutical composition comprising an isolated antibody or antibody fragment of the present disclosure, and a pharmaceutically acceptable carrier. In another embodiment the isolated antibody or antibody fragments disclosed herein for use as a drug.

The compositions of the present invention are preferably pharmaceutical compositions comprising an isolated antibody or antibody fragment which is directed against or binds to M-CSF and a pharmaceutically acceptable carrier, diluent or excipient, for the treatment of an inflammatory disorder. Such carriers, diluents and excipients are well known in the art, and the skilled artisan will find a formulation and a route of administration best suited to treat a subject with the anti-MCSF antibodies or antibody fragments of the present invention.

In certain aspects, the present invention provides a method for the treatment or prophylaxis of an inflammatory disorder in a subject, comprising the step of administering to the subject an effective amount of an antibody or antibody fragment, which is directed against or binds to M-CSF. In certain aspects said subject is a human. In alternative aspects said subject is a rodent, such as a rat or a mouse.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding composition, or by another cell. "Treatment," as it applies to a human, veterinary, or research subject, refers to therapeutic treatment, prophylactic or preventative measures, to research and diagnostic applications. "Treatment" as it applies to a human, veterinary, or research subject, or cell, tissue, or organ, encompasses contact of an agent with animal subject, a cell, tissue, physiological compartment, or physiological fluid. "Treatment of a cell" also encompasses situations where the agent contacts PILR, e.g., in the fluid phase or colloidal phase, but also situations where the agonist or antagonist does not contact the cell or the receptor.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

In another aspect the present disclosure provides to an antibody or antibody fragment specific for M-CSF, comprising 6 CDRs of any of the antibodies in Table 1. In another aspect the present disclosure provides to an antibody or antibody fragment specific for M-CSF, comprising 6 CDRs of any of the antibodies in Table 2.

In another aspect the present disclosure provides to an antibody or antibody fragment specific for M-CSF, comprising the variable heavy chain and the variable light chain of any of the antibodies in Table 1. In another aspect the present disclosure provides to an antibody or antibody fragment specific for M-CSF, comprising the variable heavy chain and the variable light chain of any of the antibodies in Table 2.

In another aspect the present disclosure provides an antibody or antibody fragment specific for M-CSF, encoded by any of the nucleic acid in Table 1. In another aspect the present disclosure provides an antibody or antibody fragment specific for M-CSF, encoded by any of the nucleic acid in Table 2. In another embodiment the present disclosure provides a vector comprising a nucleic acid of Table 1. In another embodiment the present disclosure provides a vector comprising a nucleic acid of Table 2. In another embodiment the present disclosure provides an isolated host cell comprising a vector comprising a nucleic acid of Table 1. In another embodiment the present disclosure provides an isolated host cell comprising a vector comprising a nucleic acid of Table 2. In a further embodiment said isolated host cell is a mammalian cell.

EXAMPLES

Example 1: Generation of Fab Fragments and Antibodies that are Specific for M-CSF For the selection of antibodies specifically binding to M-CSF a commercially available phage display library, the MorphoSys HuCAL PLATINUM® library was used. Said antibody library is based on the HuCAL® concept (Knappik et al., (2000) J Mol Biol 296:57-86) and employs the CYSDISPLAY® (chemical, biochemical, biological, and biotechnological preparations for use in the development of immunological reagents for industrial and scientific use by MorphoSys AG Corporation, Germany) technology for displaying the Fab on the phage surface (WO2001/05950 to Lohning). However, any other available antibody library would be suitable to identify M-CSF antibodies.

To identify M-CSF-specific antibodies different panning strategies were used. Each panning strategy comprised at least 3 individual rounds of panning against the receptor-binding domain of human M-CSF (rbdM-CSF), the sequence of which is shown in SEQ ID NO: 5.

The isolated binders identified were maturated, engineered and/or germlined in order to increase affinity and/or functionality of the initial lead molecules. Several hundred binders were screened and rigorously tested for functionality.

A subset of 45 candidate molecules were produced in exploratory scale and characterized in the following in vitro assays:

Binding to human and cynomolgus M-CSF in ELISA.

Binding to stably membrane M-CSF-transfected CHO cells and endogenously membrane M-CSF-expressing MDA-MB 231 cells (source: ATCC, order number: HTB-26).

Developability risk ranking

Functionality in the receptor inhibition assay (RIA) with human M-CSF.

Functionality in the M-NFS-60 cell (source: ATCC, order number: CTL-1838) viability assay with human M-CSF.

In total led eight preferred lead molecules were identified which are further descried herein below. The amino acid and the nucleic acid sequences of the variable regions and the CDRs of those eight binders are shown in Table 1.

TABLE 1

| ID# | | Seq. ID: | Sequence [amino acid]/[nucleic acid] |
|---|---|---|---|
| Caline | HCDR1 | Seq. ID: 8 | SNSAAWN |
| | HCDR2 | Seq. ID: 9 | RTYYRSKWKHEYAMSVKS |
| | HCDR3 | Seq. ID: 10 | DRYYYSAFDY |
| | LCDR1 | Seq. ID: 11 | TGTSSDVGGYNSVS |
| | LCDR2 | Seq. ID: 12 | AVSNRPS |
| | LCDR3 | Seq. ID: 13 | ASYDERFTRV |
| | VH | Seq. ID: 14 | QVQLQQSGPGLVKPSQTLSLICAISGDSVSSNSAAWN WIRQSPSRGLEWLGRTYYRSKWKHEYAMSVKSRITIN PDTSKNQFSLQLNSVTPEDTAVYYCARDRYYYSAFDY WGQGTLVTVSS |
| | VL | Seq. ID: 15 | QSALTQPASVSGSPGQSITISCTGTSSDVGGYNSVSW YQQHPGKAPKLMIYAVSNRPSGVSNRFSGSKSGNTA SLTISGLQAEDEADYYCASYDERFTRVFGGGTKLTVL GQ |
| | VH (DNA) | Seq. ID: 16 | caggtgcaattgcagcagagcggtccgggcctggtgaaaccgagccaga ccctgagcctgacctgcgcgatttccggcgatagtgtgagtagcaatagcgc tgcttggaactggattcgtcagagcccgagccgtggcctcgagtggctgggc cgtacctactaccgtagcaaatggaaacatgaatatgccatgagcgtgaaa agccgcattaccattaacccggatacttcgaaaaaccagtttagcctgcaac tgaacagcgtgacccccgaagatacggccgtgtattattgcgcgcgtgacc gttactactactctgctttcgattactggggccaaggcaccctggtgactgttag ctca |
| | VL (DNA) | Seq. ID: 17 | caaagcgcgctgacccagccggcgagcgtgagcggtagcccgggccag agcattaccattagctgcaccggcaccagcagcgatgtgggcggttacaatt ctgtttcttggtaccagcagcatccgggcaaggcgccgaaattgatgatttac gctgtttctaaccgtccgagcggcgtgagcaaccgttttagcggatccaaaa gcggcaacaccgcgagcctgaccattagcggcctgcaagcggaagacg aagcggattattactgcgcttcttacgacgaacgtttcactcgtgtgtttggcgg cggcacgaagttaaccgtcctaggtcag |

TABLE 1-continued

| ID# | | Seq. ID: | Sequence [amino acid]/[nucleic acid] |
|---|---|---|---|
| Camille | HCDR1 | Seq. ID: 18 | TSSAAWN |
| | HCDR2 | Seq. ID: 19 | RTYYRSKWKHEYAVSVKS |
| | HCDR3 | Seq. ID: 20 | DRYYYSAFDY |
| | LCDR1 | Seq. ID: 21 | TGTSSDVGGYNSVS |
| | LCDR2 | Seq. ID: 22 | AVSNRPS |
| | LCDR3 | Seq. ID: 23 | ASYDERFTRV |
| | VH | Seq. ID: 24 | QVQLQQSGPGLVKPSQTLSLTCAISGESVSTSSAAWN WIRQSPSRGLEWLGRTYYRSKWKHEYAVSVKSRITIN PDTSKNQFSLQLNSVTPEDTAVYYCARDRYYYSAFDY WGQGTLVTVSS |
| | VL | Seq. ID: 25 | QSALTQPASVSGSPGQSITISCTGTSSDVGGYNSVSW YQQHPGKAPKLLIYAVSNRPSGVSNRFSGSKSGNTAS LTISGLQAEDEADYYCASYDERFTRVFGGGTKLTVLG Q |
| | VH (DNA) | Seq. ID: 26 | caggtgcaattgcagcagagcggtccgggcctggtgaaaccgagccaga ccctgagcctgacctgcgcgatttccggagagagtgtgagcactagtagtgc tgcttggaactggattcgtcagagcccgagccgtggcctcgagtggctgggc cgtacctactaccgtagcaaatggaaacatgaatatgccgtgagcgtgaaa agccgcattaccattaaccccggatacttcgaaaaaaccagtttagcctgcaac tgaacagcgtgaccccggaagatacggccgtgtattattgcgcgcgtgacc gttactactactctgctttcgattactggggccaaggcaccctggtgactgttag ctca |
| | VL (DNA) | Seq. ID: 27 | caaagcgcgctgacccagccggcgagcgtgagcggtagcccgggccag agcattaccattagctgcaccggcaccagcagcgatgtgggcggttacaac tctgtttcttggtaccagcagcatccgggcaaggcgccgaaactgctgattta cgctgtttctaaccgtccgagcggcgtgagcaaccgttttagcggatccaaa agcggcaacaccgcgagcctgaccattagcggcctgcaagcggaagac gaacggattattactgcgcttcttacgacgaacgtttcactcgtgtgtttggcg gcggcacgaagttaaccgtcctaggtcag |
| Celine | HCDR1 | Seq. ID: 28 | TSSAAWN |
| | HCDR2 | Seq. ID: 29 | RTYYRSKWKHEYAVSVKS |
| | HCDR3 | Seq. ID: 30 | DRYYYSAFDY |
| | LCDR1 | Seq. ID: 31 | TGTSSDVGGYNSVS |
| | LCDR2 | Seq. ID: 32 | AVSNRPS |
| | LCDR3 | Seq. ID: 33 | ASYDERFTRV |
| | VH | Seq. ID: 34 | QVQLQQSGPGLVKPSQTLSLTCAISGDSVSTSSAAWN WIRQSPSRGLEWLGRTYYRSKWKHEYAVSVKSRITIN PDTSKNQFSLQLNSVTPEDTAVYYCARDRYYYSAFDY WGQGTLVTVSS |
| | VL | Seq. ID: 35 | QSALTQPASVSGSPGQSITISCTGTSSDVGGYNSVSW YQQHPGKAPKLIIYAVSNRPSGVSNRFSGSKSGNTAS LTISGLQAEDEADYYCASYDERFTRVFGGGTKLTVLG Q |
| | VH (DNA) | Seq. ID: 36 | caggtgcaattgcagcagagcggtccgggcctggtgaaaccgagccaga ccctgagcctgacctgcgcgatttccggagacagcgtgagtaccagtagtg ctgcttggaactggattcgtcagagcccgagccgtggcctcgagtggctggg ccgtacctactaccgtagcaaatggaaacatgaatatgccgtgagcgtgaa aagccgcattaccattaaccccggatacttcgaaaaaaccagtttagcctgcaa ctgaacagcgtgaccccggaagatacggccgtgtattattgcgcgcgtgac cgttactactactctgctttcgattactggggccaaggcaccctggtgactgtta gctca |
| | VL (DNA) | Seq. ID: 37 | caaagcgcgctgacccagccggcgagcgtgagcggtagcccgggccag agcattaccattagctgcaccggcaccagcagcgatgtgggcggttacaac tctgtttcttggtaccagcagcatccgggcaaggcgccgaaactgatcatcta cgctgtttctaaccgtccgagcggcgtgagcaaccgttttagcggatccaaa agcggcaacaccgcgagcctgaccattagcggcctgcaagcggaagac gaacggattattactgcgcttcttacgacgaacgtttcactcgtgtgtttggcg gcggcacgaagttaaccgtcctaggtcag |

TABLE 1-continued

| ID# | | Seq. ID: | Sequence [amino acid]/[nucleic acid] |
|---|---|---|---|
| Madeleine | HCDR1 | Seq. ID: 38 | SNSAAWN |
| | HCDR2 | Seq. ID: 39 | RTYYRSKWKKEYAQSVKS |
| | HCDR3 | Seq. ID: 40 | DRYYYSAFDY |
| | LCDR1 | Seq. ID: 41 | TGTSSDVGGYNSVS |
| | LCDR2 | Seq. ID: 42 | AVSNRPS |
| | LCDR3 | Seq. ID: 43 | ASYDERFTRV |
| | VH | Seq. ID: 44 | QVQLQQSGPGLVKPSQTLSLTCAISGDSVSSNSAAWN WIRQSPSRGLEWLGRTYYRSKWKKEYAQSVKSRITIN PDTSKNQFSLQLNSVTPEDTAVYYCARDRYYYSAFDY WGQGTLVTVSS |
| | VL | Seq. ID: 45 | QSALTQPASVSGSPGQSITISCTGTSSDVGGYNSVSW YQQHPGKAPKLMIYAVSNRPSGVSNRFSGSKSGNTA SLTISGLQAEDEADYYCASYDERFTRVFGGGTKLTVL GQ |
| | VH (DNA) | Seq. ID: 46 | caggtgcaattgcagcagagcggtccgggcctggtgaaaccgagccaga ccctgagcctgacctgcgcgatttccggagatagcgtgagcagtaactctgc tgcttggaactggattcgtcagagcccgagccgtggcctcgagtggctggg cgtacctactaccgtagcaaatggaaaaaagaatatgcccagagcgtgaa aagccgcattaccattaacccggatacttcgaaaaaccagtttagcctgcaa ctgaacagcgtgaccccggaagatacggccgtgtattattgcgcgcgtgac cgttactactactctgctttcgattactggggccaaggcaccctggtgactgtta gctca |
| | VL (DNA) | Seq. ID: 47 | caaagcgcgctgacccagccggcgagcgtgagcggtagcccgggccag agcattaccattagctgcaccggcaccagcagcgatgtgggcggttacaatt ctgtttcttggtaccagcagcatccgggcaaggcgccgaaattgatgattttac gctgtttctaaccgtccgagcggcgtgagcaaccgttttagcggatccaaaa gcggcaacaccgcgagcctgaccattagcggcctgcaagcggaagacg aagcggattattactgcgcttcttacgacgaacgtttcactcgtgtgtttggcgg cggcacgaagttaaccgtcctaggtcag |
| Maelle | HCDR1 | Seq. ID: 48 | TSSAAWN |
| | HCDR2 | Seq. ID: 49 | RTYYRSKWKKEYAQSVKS |
| | HCDR3 | Seq. ID: 50 | DRYYYSAFDY |
| | LCDR1 | Seq. ID: 51 | TGTSSDVGGYNSVS |
| | LCDR2 | Seq. ID: 52 | AVSNRPS |
| | LCDR3 | Seq. ID: 53 | ASYDERFTRV |
| | VH | Seq. ID: 54 | QVQLQQSGPGLVKPSQTLSLTCAISGESVSTSSAAWN WIRQSPSRGLEWLGRTYYRSKWKKEYAQSVKSRITIN PDTSKNQFSLQLNSVTPEDTAVYYCARDRYYYSAFDY WGQGTLVTVSS |
| | VL | Seq. ID: 55 | QSALTQPASVSGSPGQSITISCTGTSSDVGGYNSVSW YQQHPGKAPKLIIYAVSNRPSGVSNRFSGSKSGNTAS LTISGLQAEDEADYYCASYDERFTRVFGGGTKLTVLG Q |
| | VH (DNA) | Seq. ID: 56 | caggtgcaattgcagcagagcggtccgggcctggtgaaaccgagccaga ccctgagcctgacctgcgcgatttccggagaaagcgtgagtaccagcagtg ctgcttggaactggattcgtcagagcccgagccgtggcctcgagtggctggg ccgtacctactaccgtagcaaatggaaaaaagaatatgcccagagcgtga aaagccgcattaccattaacccggatacttcgaaaaaccagtttagcctgca actgaacagcgtgaccccggaagatacggccgtgtattattgcgcgcgtga ccgttactactactctgctttcgattactggggccaaggcaccctggtgactgtt agctca |
| | VL (DNA) | Seq. ID: 57 | caaagcgcgctgacccagccggcgagcgtgagcggtagcccgggccag agcattaccattagctgcaccggcaccagcagcgatgtgggcggttacaac tctgtttcttggtaccagcagcatccgggcaaggcgccgaaactgatcatcta cgctgtttctaaccgtccgagcggcgtgagcaaccgttttagcggatccaaa agcggcaacaccgcgagcctgaccattagcggcctgcaagcggaagac gaagcggattattactgcgcttcttacgacgaacgtttcactcgtgtgtttggcg gcggcacgaagttaaccgtcctaggtcag |

TABLE 1-continued

| ID# | | Seq. ID: | Sequence [amino acid]/[nucleic acid] |
|---|---|---|---|
| Meriem | HCDR1 | Seq. ID: 58 | TSSAAWN |
| | HCDR2 | Seq. ID: 59 | RTYYRSKWKKEYAQSVKS |
| | HCDR3 | Seq. ID: 60 | DRYYYSAFDY |
| | LCDR1 | Seq. ID: 61 | TGTSSDVGGYNSVS |
| | LCDR2 | Seq. ID: 62 | AVSNRPS |
| | LCDR3 | Seq. ID: 63 | ASYDERFTRV |
| | VH | Seq. ID: 64 | QVQLQQSGPGLVKPSQTLSLTCAISGDSVSTSSAAWN WIRQSPSRGLEWLGRTYYRSKWKKEYAQSVKSRITIN PDTSKNQFSLQLNSVTPEDTAVYYCARDRYYYSAFDY WGQGTLVTVSS |
| | VL | Seq. ID: 65 | QSALTQPASVSGSPGQSITISCTGTSSDVGGYNSVSW YQQHPGKAPKLIIYAVSNRPSGVSNRFSGSKSGNTAS LTISGLQAEDEADYYCASYDERFTRVFGGGTKLTVLG Q |
| | VH (DNA) | Seq. ID: 66 | caggtgcaattgcagcagagcggtccgggcctggtgaaaccgagccaga<br>ccctgagcctgacctgcgcgatttccggcgacagcgtgagcaccagtagtg<br>ctgcttggaactggattcgtcagagcccgagccgtggcctcgagtggctggg<br>ccgtacctactaccgtagcaaatggaaaaaagaatatgccccagagcgtga<br>aaagccgcattaccattaacccggatacttcgaaaaaccagtttagcctgca<br>actgaacagcgtgaccccggaagatacggccgtgtattattgcgcgcgtga<br>ccgttactactactctgctttcgattactggggccaaggcaccctggtgactgtt<br>agctca |
| | VL (DNA) | Seq. ID: 67 | caaagcgcgctgacccagccggcgagcgtgagcggtagcccgggccag<br>agcattaccattagctgcaccggcaccagcagcgatgtgggcggttacaac<br>tctgtttcttggtaccagcagcatccgggcaaggcgccgaaactgatcatcta<br>cgctgtttctaaccgtccgagcggcgtgagcaaccgtttagcggatccaaa<br>agcggcaacaccgcgagcctgaccattagcggcctgcaagcggaagac<br>gaagcggattattactgcgcttcttacgacgaacgtttcactcgtgtgtttggcg<br>gcggcacgaagttaaccgtcctaggtcag |
| Satine | HCDR1 | Seq. ID: 68 | IYAMS |
| | HCDR2 | Seq. ID: 69 | RIKSNADGGTTEYAAPVKG |
| | HCDR3 | Seq. ID: 70 | MRYYSDLYFDP |
| | LCDR1 | Seq. ID: 71 | SGDKLGQKYVS |
| | LCDR2 | Seq. ID: 72 | QDRKRPS |
| | LCDR3 | Seq. ID: 73 | QTWTHLQWV |
| | VH | Seq. ID: 74 | EVQLVESGGGLVKPGGSLRLSCAASGFTFSIYAMSWV RQAPGKGLEVVVGRIKSNADGGTTEYAAPVKGRFTISR DDSKNTLYLQMNSLKTEDTAVYYCARMRYYSDLYFDP WGQGTLVTVSS |
| | VL | Seq. ID: 75 | SYELTQPPSVSVSPGQTASITCSGDKLGQKYVSWYQ QKPGQSPVLVISQDRKRPSGIPERFSGSNSGNTATLTI SGTQAEDEADYYCQTWTHLQWVFGGGTKLTVLGQ |
| | VH (DNA) | Seq. ID: 76 | gaagtgcagctggtggaaagcggcggtggcctggtgaaaccaggcggca<br>gcctgcgcctgagctgcgccgccagcggctttacctttagcatctacgctatg<br>agctgggtgcgccaggcccgggcaaaggtctggaatgggtgggccgtat<br>caaatctaacgctgacggtggtactactgaatatgccgccccagtgaaagg<br>ccgctttaccattagccgcgatgatagcaaaaacaccctgtatctgcaaatg<br>aacagcctgaaaaccgaagatacggccgtgtattattgcgcgcgtatgcgtt<br>actactctgacctgtacttcgatccgtggggtcaaggcaccctggtgactgtct<br>cgagc |
| | VL (DNA) | Seq. ID: 77 | agctatgaactgacccagccgccgagcgttagcgttagcccaggccagac<br>cgccagcattacctgtagcggcgacaaactggggcaaaaatacgtgtcctg<br>gtatcagcagaaaccgggccagagcccggtgctggttatcagtcaggatcg<br>taaacgcccgagcggcattccagaacgctttagcggcagcaacagcggc<br>aacaccgccaccctgaccattagcggcacccaggccgaagacgaagcc<br>gattattactgccagacttggacccacctgcaatgggtgtttggcggcggtac<br>caagctgaccgtgctgggccag |

TABLE 1-continued

| ID# | | Seq. ID: | Sequence [amino acid]/[nucleic acid] |
|---|---|---|---|
| Servane | HCDR1 | Seq. ID: 78 | TYAIS |
| | HCDR2 | Seq. ID: 79 | FIKSKHNSGTTEYAAPVKG |
| | HCDR3 | Seq. ID: 80 | MRYYSDLYFDP |
| | LCDR1 | Seq. ID: 81 | SGDKLGQKYVS |
| | LCDR2 | Seq. ID: 82 | QDRKRPS |
| | LCDR3 | Seq. ID: 83 | QTWTHLQWV |
| | VH | Seq. ID: 84 | EVQLVESGGGLVKPGGSLRLSCAASGFTFSTYAISWV RQAPGKGLEWVGFIKSKHNSGTTEYAAPVKGRFTISR DDSKNTLYLQMNSLKTEDTAVYYCARMRYYSDLYFDP WGQGTLVTVSS |
| | VL | Seq. ID: 85 | SYELTQPPSVSVSPGQTASITCSGDKLGQKYVSWYQ QKPGQSPVLVISQDRKRPSGIPERFSGSNSGNTATLTI SGTQAEDEADYYCQTWTHLQWVFGGGTKLTVLGQ |
| | VH (DNA) | Seq. ID: 86 | gaagtgcaattggtggaaagcggcggtggcctggtgaaaccaggcggca gcctgcgcctgagctgcgccgcctccggattcaccttttctacttacgctatctc ttgggtgcgccaggcccgggcaaaggtctcgagtgggtgggcttcatcaa atctaaacataactctggtactactgaatatgccgccccagtgaaaggccgc tttaccattagccgcgatgattcgaaaaacaccctgtatctgcaaatgaacag cctgaaaaccgaagatacggccgtgtattattgcgcgcgtatgcgttactact ctgacctgtacttcgatccgtggggtcaaggcaccctggtgactgtctcgagc |
| | VL (DNA) | Seq. ID: 87 | agctatgaactgacccagccgccgagcgttagcgttagcccaggccagac cgccagcattacctgtagcggcgacaaactggggcaaaaatacgtgtcctg gtatcagcagaaaccgggccagagcccggtgctggttatcagtcaggatcg taaacgcccgagcggcattccagaacgctttagcggcagcaacagcggc aacaccgccaccctgaccattagcggcacccaggccgaagacgaagcc gattattactgccagacttggacccacctgcaatgggtgtttggcggcggtac caagctgaccgtgctgggccag |

Antibodies Caline, Camille and Celine are derivatives of parental antibody Blanche. Antibodies Madeleine, Maelle and Meriem are derivatives of parental antibody Laurine. Antibodies Satine and Servane are derivatives of parental antibody Romaine. The amino acid and the nucleic acid sequences of the variable regions and the CDRs of the parental antibodies are shown in Table 2.

TABLE 2

| ID# | | Seq. ID: | Sequence [amino acid]/[nucleic acid] |
|---|---|---|---|
| Blanche | HCDR1 | Seq. ID: 88 | SNSAAWN |
| | HCDR2 | Seq. ID: 89 | RTYYRSKWKHEYAMSVKS |
| | HCDR3 | Seq. ID: 90 | DRYYSAFDY |
| | LCDR1 | Seq. ID: 91 | TGTSSDVGGYNSVS |
| | LCDR2 | Seq. ID: 92 | AVSNRPS |
| | LCDR3 | Seq. ID: 93 | ASYDERFTRV |
| | VH | Seq. ID: 94 | QVQLQQSGPGLVKPSQTLSLTCAISGDSVSSNSAAWN WIRQSPSRGLEWLGRTYYRSKWKHEYAMSVKSRITIN PDTSKNQFSLQLNSVTPEDTAVYYCARDRYYSAFDY WGQGTLVTVSS |
| | VL | Seq. ID: 95 | DIALTQPASVSGSPGQSITISCTGTSSDVGGYNSVSWY QQHPGKAPKLMIYAVSNRPSGVSNRFSGSKSGNTASL TISGLQAEDEADYYCASYDERFTRVFGGGTKLTVLGQ |
| | VH (DNA) | Seq. ID: 96 | caggtgcaattgcagcagagcggtccgggcctggtgaaaccgagccaga cccctgagcctgacctgcgcgatttccggagatagcgtgagcagtaactctgc tgcttggaactggattcgtcagagcccgagccgtggcctcgagtggctgggc cgtacctactaccgtagcaaatggaaacatgaatatgccatgagcgtgaaa agccgcattaccattaacccggatacttcgaaaaaccagtttagcctgcaac tgaacagcgtgaccccggaagatacggccgtgtattattgcgcgcgtgacc gttactactactctgctttcgattactggggccaaggcaccctggtgactgttag ctca |

TABLE 2-continued

| ID# | | Seq. ID: | Sequence [amino acid]/[nucleic acid] |
|---|---|---|---|
| | VL (DNA) | Seq. ID: 97 | gatatcgcgctgacccagccggcgagcgtgagcggtagcccgggccaga gcattaccattagctgcaccggcaccagcagcgatgtgggcggttacaact ctgtgtcttggtaccagcagcatccgggcaaggcgccgaaactgatgatcta cgctgtttctaaccgtccgagcggcgtgagcaaccgttttagcggatccaaa agcggcaacaccgcgagcctgaccattagcggcctgcaagcggaagac gaagcggattattactgcgcttcttacgacgaacgttttcactcgtgtgtttggcg gcggcacgaagttaaccgtcctaggtcag |
| Laurine | HCDR1 | Seq. ID: 98 | SNSAAWN |
| | HCDR2 | Seq. ID: 99 | RTYYRSKWKKEYAQSVKS |
| | HCDR3 | Seq. ID: 100 | DRYYYSAFDY |
| | LCDR1 | Seq. ID: 101 | TGTSSDVGGYNSVS |
| | LCDR2 | Seq. ID: 102 | AVSNRPS |
| | LCDR3 | Seq. ID: 103 | ASYDERFTRV |
| | VH | Seq. ID: 104 | QVQLQQSGPGLVKPSQTLSLTCAISGDSVSSNSAAWN WIRQSPSRGLEWLGRTYYRSKWKKEYAQSVKSRITIN PDTSKNQFSLQLNSVTPEDTAVYYCARDRYYYSAFDY WGQGTLVTVSS |
| | VL | Seq. ID: 105 | DIALTQPASVSGSPGQSITISCTGTSSDVGGYNSVSWY QQHPGKAPKLMIYAVSNRPSGVSNRFSGSKSGNTASL TISGLQAEDEADYYCASYDERFTRVFGGGTKLTVLGQ |
| | VH (DNA) | Seq. ID: 106 | caggtgcaattgcagcagagcggtccgggcctggtgaaaccgagccaga ccctgagcctgacctgcgcgcgatttccggagatagcgtgagcagtaactctgc tgcttggaactggattcgtcagagcccgagccgtggcctcgagtggctgggc cgtacctactaccgtagcaaatggaaaaagaatatgcccagagcgtgaa aagccgcattaccattaacccggatacttcgaaaaaccagtttagcctgcaa ctgaacagcgtgaccccggaagatacggccgtgtattattgcgcgcgtgac cgttactactactctgcttcgattactggggccaaggcaccctggtgactgtta gctca |
| | VL (DNA) | Seq. ID: 107 | Gatatcgcgctgacccagccggcgagcgtgagcggtagcccgggccag agcattaccattagctgcaccggcaccagcagcgatgtgggcggttacaac tctgtgtcttggtaccagcagcatccgggcaaggcgccgaaactgatgatct acgctgtttctaaccgtccgagcggcgtgagcaaccgttttagcggatccaa aagcggcaacaccgcgagcctgaccattagcggcctgcaagcggaaga cgaagcggattattactgcgcttcttacgacgaacgttttcactcgtgtgtttggc ggcggcacgaagttaaccgtcctaggtcag |
| Romaine | HCDR1 | Seq. ID: 108 | IYAMS |
| | HCDR2 | Seq. ID: 109 | RIKSNADGGTTEYAAPVKG |
| | HCDR3 | Seq. ID: 110 | MRYYSDLYFDP |
| | LCDR1 | Seq. ID: 111 | SGDAIGSKYVH |
| | LCDR2 | Seq. ID: 112 | KDNKRPS |
| | LCDR3 | Seq. ID: 113 | QTATVSSYWWV |
| | VH | Seq. ID: 114 | EVQLVESGGGLVKPGGSLRLSCAASGFTFSIYAMSWV RQAPGKGLEWVGRIKSNADGGTTEYAAPVKGRFTISR DDSKNTLYLQMNSLKTEDTAVYYCARMRYYSDLYFDP WGQGTLVTVSS |
| | VL | Seq. ID: 115 | DIELTQPPSVSVSPGQTASITCSGDAIGSKYVHWYQQ KPGQAPVLVISKDNKRPSGIPERFSGSNSGNTATLTIS GTQAEDEADYYCQTATVSSYWWVFGGGTKLTVLGQ |
| | VH (DNA) | Seq. ID: 116 | caggtgcaattggtggaaagcggcggtggcctggtgaaaccaggcggca gcctgcgcctgagctgcgccgcctccggattcaccttttctatctacgctatgtc ttggtgcgccaggccccgggcaaagtctcgagtgggtgggccgtatcaa atctaacgctgacggtggtactactgaatatgccgcccagtgaaaggccg ctttaccattagccgcgatgattcgaaaaacaccctgtatctgcaaatgaaca gcctgaaaaccgaagatacggccgtgtattattgcgcgcgtatgcgttactac tctgacctgtacttcgatccgtggggccaaggcaccctggtgactgttagctc a |

TABLE 2-continued

| ID# | Seq. ID: | Sequence [amino acid]/[nucleic acid] |
|---|---|---|
| VL (DNA) | Seq. ID: 117 | gatatcgaactgacccagccgccgagcgtgagcgtgagcccgggccaga ccgcgagcattacctgtagcggcgattgctatcggttctaaatacgttcattggt accagcagaaaccgggccaggcgccggtgctggtgatctctaaagacaa caaacgtccgagcggcatcccggaacgttttagcggatccaacagcggca acaccgcgaccctgaccattagcggcacccaggcggaagacgaagcgg attattactgccagactgctactgtttcttcttactggtgggtgtttggcggcggc acgaagttaaccgtcctaggtcag |

Example 2: Characterisation and Benchmarking of the M-CSF Specific Antibodies The eight preferred M-CSF specific antibodies were characterized in depth as described herein below. The antibodies were compared to the respective parental antibodies and to two prior art antibodies which were generated for clinical development. The amino acid sequence of HeRX1-10G1 (Novartis) is for example disclosed in WO 2005/068503 and also shown in Table 3. The amino acid sequence of 8.10.3F (Pfizer) is for example disclosed in WO 2005/030124 and also shown in Table 3. HeRX1-10G1 and 8.10.3F were synthesized using conventional molecular biology techniques.

TABLE 3

| ID# | | Seq. ID: | Sequence [amino acid]/[nucleic acid] |
|---|---|---|---|
| HeRX1-10G1 | HCDR1 | Seq. ID: 118 | SDYAWN |
| | HCDR2 | Seq. ID: 119 | YISYSGSTSYNPSLKS |
| | HCDR3 | Seq. ID: 120 | FDYAHAMDY |
| | LCDR1 | Seq. ID: 121 | QASQSIGTSIH |
| | LCDR2 | Seq. ID: 122 | YASESIS |
| | LCDR3 | Seq. ID: 123 | QQINSWPT |
| | VH | Seq. ID: 124 | QVQLQESGPGLVKPSQTLSLTCTVSDYSITSDYAWNW IRQFPGKGLEWMGYISYSGSTSYNPSLKSRITISRDTS KNQFSLQLNSVTAADTAVYYCASFDYAHAMDYWGQG TTVTVSS |
| | VL | Seq. ID: 125 | DIVLTQSPAFLSVTPGEKVTFTCQASQSIGTSIHWYQQ KTDQAPKLLIKYASESISGIPSRFSGSGSGTDFTLTISS VEAEDAADYYCQQINSWPTTFGGGTKLEIKRT |
| | VH (DNA) | Seq. ID: 126 | caggtgcaattgcaggaaagcggccctggcctggtcaagcctagccagac cctgagcctgacctgcaccgtgtccgactacagcatcaccagcgactacgc ctggaactggatccggcagttccccggcaagggcctggaatggatgggcta catcagctacagcggcagcaccagctacaacccagcctgaagtcccgg atcaccatcagccgggacaccagcaagaaccagtttagcctccagctgaa cagcgtgacagccgccgacaccgccgtgtactactgcgccagcttcgacta cgcccacgccatggattactggggccagggcaccaccgtgaccgtcagct ca |
| | VL (DNA) | Seq. ID: 127 | gatatcgtgctgacccagagccccgccctttctgagcgtgacccctggcgaga aagtgacattcacatgccaggccagcagagcatcggcaccagcatccac tggtatcagcagaaaaccgaccaggcccccaaactcctgatcaagtacgc cagcgagtccatcagcggcatcccagcagattcagcggcagcggctccg gcaccgacttcaccctgaccatcagcagcgtggaggccgaggacgccgc cgactactactgccagcagatcaacagctggcccaccacctttggcggagg caccaagctggaaatcaagcgtacg |
| 8.10.3F | HCDR1 | Seq. ID: 128 | SFSMT |
| | HCDR2 | Seq. ID: 129 | YISSRSSTISYADSVKG |
| | HCDR3 | Seq. ID: 130 | DPLLAGATFFDY |
| | LCDR1 | Seq. ID: 131 | RASQSVSSSYLA |
| | LCDR2 | Seq. ID: 132 | GASSRAT |
| | LCDR3 | Seq. ID: 133 | QQYGSSPL |
| | VH | Seq. ID: 134 | EVQLVESGGGLVQPGGSLRLSCAASGFTFSSFSMTW VRQAPGKGLEWVSYISSRSSTISYADSVKGRFTISRDN AKNSLYLQMNSLRDEDTAVYYCARDPLLAGATFFDYW |

TABLE 3-continued

| ID# | | Seq. ID: | Sequence [amino acid]/[nucleic acid] |
|---|---|---|---|
| | | | GQGTLVTVSS |
| | VL | Seq. ID: 135 | DIVLTQSPGTLSLSPGERATLSCRASQSVSSSYLAWY QQKPGQAPRLLIYGASSRATGIPDRFSGSGSGTDFTL TISRLEPEDFAVYYCQQYGSSPLTFGGGTKVEIKRT |
| | VH (DNA) | Seq. ID: 136 | caggtgcaattggtggagagcggcggaggactggtgcagcctggcggaa gcctgagactgtcttgcgccgccagcggcttcaccttcagcagcttcagcatg acatgggtccgccaagcccctggaaagggcctggaatgggtgtcctacatc agcagccggtccagcaccatcagctacgccgacagcgtgaagggccggt tcaccatcagccgggacaacgccaagaacagcctgtacctgcagatgaa cagcctgcgggacgaggacaccgccgtgtactactgcgccagagatcctct gctggctggcgccaccttcttcgactactggggccagggcacctggtcaca gtcagctca |
| | VL (DNA) | Seq. ID: 137 | gatatcgtgctgacccagtctcctggcaccctgtctctgagccctggcgagag agccaccctgagctgcagagccagccagagcgtgtccagcagctacctgg cctggtatcagcagaagcccggccaggcccccagactgctgatctacggc gccagcagcagagccaccggcatccccgacagattcagcggcagcggct ccggcaccgacttcacctgaccatctctcggctggaacccgaggacttcg ccgtgtactactgccagcagtacggcagcagccctctgaccttcggcggag gcaccaaggtggagatcaagcgtacg |

The antibodies of the present disclosure may be used in any format, i.e. as full lengths immunoglobulins or as antibody fragments as described herein. The full length antibodies may be used in any immunoglobulin isotype or class. With a few exceptions, the antibodies of the present invention were tested in IgG1 format and in a silenced IgG1 format harboring a D265A mutation in the Fc region. Antibody 8.10.3F was also tested in IgG2 format.

Example 3: Specificity for M-CSF as Determined in an ELISA Assay

Specificity for human M-CSF and cynomolgus M-CSF was tested in an ELISA assay. BSA was used as a negative control substrate.

MAXISORP™ (high protein-binding capacity ELISA plates by Thermo Fisher Scientific, Waltham, Mass.) 384 well plates were coated with human rbdM-CSF, human sgM-CSF, cyno sgM-CSF or mouse sgM-CSF at a concentration of 2 μg/ml in PBS. After blocking of plates with 5% skim milk powder in PBS, Fab-containing E. coli lysates, IgG-containing cell culture supernatants or purified IgG or Fab proteins were added. Binding of Fabs or IgGs was detected by F(ab)$_2$ specific goat anti-human IgG conjugated to alkaline phosphatase (Dianova Cat#109-055-097; diluted 1:5000) using Attophos fluorescence substrate (Roche, #11681982001). Fluorescence emission at 535 nm was recorded with excitation at 430 nm.

In an alternative experimental set-up, Maxisorp™ 384 well plates were coated with Fd fragment specific sheep anti-human IgG (The Binding Site, #PC075) diluted 1:1000 in PBS. After blocking with 5% skim milk powder in PBS, Fab-containing E. coli lysates were added. Subsequently the captured HuCAL®-Fab fragments were allowed to bind to 0.5 μg/ml biotinylated M-CSF (human sgM-CSF, human rbdM-CSF, or mouse sgM-CSF) which was detected by incubation with streptavidin conjugated to alkaline phosphatase followed by addition of AttoPhos fluorescence substrate (Roche, #11681982001). Fluorescence emission at 535 nm was recorded with excitation at 430 nm.

All antibodies shown in Tables 1, 2 and 3 strongly bound to human M-CSF and cynomolgus M-CSF (>35,000 units), whereas none of the antibodies bound to BSA (<1,000 units). All antibodies are therefore highly specific for M-CSF.

Example 4: Specificity for M-CSF as Determined in a FACS Experiment; EC50s

A FACS study was performed in order to test if the antibodies of the present disclosure also binds to M-CSF expressed on cells. Two cell lines were used for this purpose: CHO cells which were stably transfected with M-CSF, and the cell line MDA-MB-231 which endogenously expresses M-CSF. Apparent $K_D$ values ($EC_{50}$) were determined with both cell lines. The results are shown in Table 4. All values are in [nM].

TABLE 4

$EC_{50}$ values of antibodies as determined in a FACS assay (nM)

| Antibody# | Format | CHO cells (n = 3) | MDA-MB 231 cells (n = 2) |
|---|---|---|---|
| Blanche | IgG1_D265A | 7.5 | 10 |
| Caline | IgG1_D265A | 9.8 | 14 |
| Camille | IgG1_D265A | 6.1 | 14 |
| Celine | IgG1_D265A | 9.7 | 13 |
| Laurine | IgG1_D265A | 11.2 | 9 |
| Madeleine | IgG1_D265A | 6.4 | 10 |
| Maelle | IgG1_D265A | 10.2 | 8 |
| Meriem | IgG1_D265A | 12.3 | 10 |
| Romaine | IgG1_D265A | 16.4 | 19 |
| Satine | IgG1_D265A | 11.3 | 26 |
| Servane | IgG1_D265A | 21.3 | n.d. |
| HeRX1-10G1 | IgG1 | 12.6 | 27 |
| HeRX1-10G1 | IgG1_D265A | 8.9 | 23 |
| 8.10.3F | IgG2 | 23.2 | 310 |
| 8.10.3F | IgG1_D265A | 8.9 | 16 |

All antibodies of the present invention show $EC_{50}$ values which are at least as good as those of the prior art antibodies HeRX1-10G1 and 8.10.3F, and many antibodies show $EC_{50}$ values which are better (lower) that those of the prior art antibodies.

Example 5: Inhibition of Receptor Binding

In this experiment the ability of the antibodies to block binding of human or cynomolgus M-CSF to recombinant human M-CSF receptor (provided as Fc fusion protein) was assessed.

The following recombinant ligand/receptor-combinations were used:

TABLE 5

Ligand/receptor combinations used in Receptor inhibition assays

Human M-CSF

| Ligand | Recombinant human sgM-CSF |
|---|---|
| Receptor | Recombinant human CSF1-R-Fc (R&D Systems Cat. Nr. #329-MR) |

Mouse M-CSF

| Ligand | Recombinant murine sgM-CSF |
|---|---|
| Receptor | Recombinant murine M-CSF receptor CSF-1R-Fc (R&D Systems, Cat. Nr.#3818-MR) |

Cyno M-CSF

| Ligand | Recombinant cynomolgus monkey sgM-CSF |
|---|---|
| Receptor | Recombinant human CSF1-R-Fc (R&D Systems Cat. Nr. #329-MR) |

M-CSF at a final concentration of 12.5 pM (0.66 ng/ml) was preincubated with different concentrations of anti-M-CSF antibody (0.1 pM-100 nM; all dilutions in ECL-buffer) for 1 h at room temperature. Complexes were then transferred to 384 well MSD plates coated with 2 µg/ml of the corresponding receptor. Plates were then washed and incubated with the streptavidin/ECL conjugate for 2 h with shaking at room temperature. 35 µl MSD read buffer T with surfactant was then added per well and subsequently measured using MSD Sector Imager 6000.

IC50 values were calculated for both, human M-CSF and cynomolgus M-CSF. The results are shown in Table 6. All values are in [pM]. n=4, except for HeRX1-10G1 in IgG1 format and 8.10.3F in IgG2 format.

TABLE 6

$IC_{50}$ values of antibodies as determined in a receptor binding inhibition assay (pM)

| Antibody# | Format | Human M-CSF | Cynomolgus M-CSF |
|---|---|---|---|
| Blanche | IgG1_D265A | 6.2 | 6.6 |
| Caline | IgG1_D265A | 6.1 | 6.3 |
| Camille | IgG1_D265A | 4.4 | 5.9 |
| Celine | IgG1_D265A | 4.7 | 6.9 |
| Laurine | IgG1_D265A | 4.9 | 4.3 |
| Madeleine | IgG1_D265A | 5.6 | 5.6 |
| Maelle | IgG1_D265A | 5.3 | 6.4 |
| Meriem | IgG1_D265A | 7.0 | 7.3 |
| Romaine | IgG1_D265A | 9.1 | 9.1 |
| Satine | IgG1_D265A | 15.1 | 13.5 |
| Servane | IgG1_D265A | 31.3 | 11.8 |
| HeRX1-10G1 | IgG1 | 26.5 | 27.6 |
| HeRX1-10G1 | IgG1_D265A | 28.0 | 18.0 |
| 8.10.3F | IgG2 | 31.4 | 20.7 |
| 8.10.3F | IgG1_D265A | 19.2 | 14.6 |

All candidates blocked the binding of M-CSF to its receptor better than the prior art antibodies HeRX1-10G1 and 8.10.3F. This is particularly true for the antibodies which are derived from the parental antibodies Blanche and Laurine, all of which shown 1050 values of below 10 pM.

Example 6: Inhibition of Proliferation Induced by Recombinant M-CSF

The ability of the antibodies of the present disclosure to block the bioactivity of recombinant M-CSF was assessed in a cell viability assay using the M-CSF-dependent murine myeloid cell line M-NFS-60. Proliferation of this cell line can be induced by human, cynomolgus, rat, and mouse M-CSF. To characterize the anti-M-CSF antibodies, proliferation was induced either by recombinant soluble M-CSF, native soluble M-CSF, or by transfectants expressing cell-surface M-CSF. The following components were tested (Examples 5-7).

TABLE 7

Origin of the M-CSF tested in the Proliferation Inhibition Assays (Examples 5-7)

Recombinant M-CSF

Recombinant human sgM-CSF [final conc. in assay: 9.5 pM]
Recombinant murine sgM-CSF [final conc. in assay: 9.5 pM]
Recombinant cynomolgus monkey sgM-CSF [final conc. in assay: 9.5 pM]
Recombinant rat M-CSF (PromoKine, Cat #E60442)
[final conc. in assay: 9.5 pM]
Secreted M-CSF Conditioned cell culture medium from MDA-MB-231 cells collected after 3 days of incubation [final conc. in assay: 50%]
Cell-bound M-CSF CHO cells stably transfected with human M-CSF, fixed with 2.5% glutaraldehyde for 30 min at room temperature
Serum Human serum (Sigma H45522; heat inactivated 30 min at 56° C.) [final conc. in assay: 50%]

M-NFS-60 cells were cultured (96 well plates) in RPMI 1640 containing stabilized glutamine (Pan Biotech, PAN-P04-18500) and supplemented with 10% FCS, 1 mM Na-Pyruvate, 10 mM HEPES and in the presence of 9.5 pM (0.5 ng/ml) recombinant human or cynomolgus M-CSF and increasing concentration of antibodies. Viability of the cells was determined after 3 days of culture with CELLTITER-GLO® (luminescent cell viability assay for research and scientific use by Promega Corporation, Madison, Wis.) reagent (Promega, Cat# G-7571). Luminescence was measured with a standard luminometer to determine cell viability (relative ATP content). $IC_{50}$ values were determined using GraphPad Prism software. The results are shown in Table 8. All values are in [pM].

TABLE 8

$IC_{50}$ values of antibodies as determined in an assay measuring the inhibition of proliferation induced by recombinant M-CSF [pM]

| Antibody# | Format | Human M-CSF (n = 2) | Cynomolgus M-CSF (n = 2) |
|---|---|---|---|
| Blanche | IgG1_D265A | 2.9 | 3.3 |
| Caline | IgG1_D265A | 3.1 | 4.3 |
| Camille | IgG1_D265A | 2.3 | 2.6 |
| Celine | IgG1_D265A | 2.7 | 3.0 |
| Laurine | IgG1_D265A | 2.6 | 2.8 |
| Madeleine | IgG1_D265A | 3.0 | 2.8 |
| Maelle | IgG1_D265A | 2.7 | 2.3 |
| Meriem | IgG1_D265A | 3.1 | 2.8 |
| Romaine | IgG1_D265A | 8.4 | 8.1 |
| Satine | IgG1_D265A | 5.3 | 5.4 |
| Servane | IgG1_D265A | 11.8 | 13.4 |
| HeRX1- | IgG1 | 3.6 | 4.1 |

TABLE 8-continued

IC$_{50}$ values of antibodies as determined in an assay measuring the inhibition of proliferation induced by recombinant M-CSF [pM]

| Antibody# | Format | Human M-CSF (n = 2) | Cynomolgus M-CSF (n = 2) |
|---|---|---|---|
| 10G1 HeRX1-10G1 | IgG1_D265A | 3.0 | 3.5 |
| 8.10.3F | IgG2 | 71.1 | 84.6 |
| 8.10.3F | IgG1_D265A | 14.9 | 16.5 |

All antibodies tested blocked the binding of M-CSF to its receptor. In particular, the antibodies which are derived from the parental antibodies Blanche and Laurine are more potent than the prior art antibodies, in particular more potent than 8.10.3F.

Example 7: Inhibition of Proliferation Induced by Native M-CSF

The ability of the antibodies of the present disclosure to block the bioactivity of native human M-CSF was assessed in an M-NFS-60 cell proliferation assay. Here, proliferation was induced either by human serum or MDA-MB-231 conditioned medium. Antibodies were pre-incubated for 30 min in serum in a 96 well-plate before 1000 M-NFS-60 cells were added. The final serum concentration was 50% and the cell culture medium was not supplemented with FCS. Cell viability was determined as described above after 3 days. Immunoglobulins were titrated and IC50s were calculated. The results are shown in Table 9. All values are in [pM].

TABLE 9

IC$_{50}$ values of antibodies as determined in an assay mesruing the inhibition of proliferation by recombinant M-CSF (pM)

| Antibody# | Format | Human serum | MDA-MB-231 conditioned medium |
|---|---|---|---|
| Blanche | IgG1_D265A | 18.3 | 120.5 |
| Caline | IgG1_D265A | 17.7 | 106.9 |
| Camille | IgG1_D265A | 17.7 | 98.5 |
| Celine | IgG1_D265A | 23.8 | 72.4 |
| Laurine | IgG1_D265A | 15.6 | 95.0 |
| Madeleine | IgG1_D265A | 20.0 | 75.4 |
| Maelle | IgG1_D265A | 16.0 | 98.9 |
| Meriem | IgG1_D265A | 15.1 | 76.9 |
| Romaine | IgG1_D265A | 25.2 | 83.3 |
| Satine | IgG1_D265A | 31.8 | 70.8 |
| Servane | IgG1_D265A | 93.2 | 107.0 |
| HeRX1-10G1 | IgG1 | 15.4 | 90.3 |
| HeRX1-10G1 | IgG1_D265A | 12.4 | 59.1 |
| 8.10.3F | IgG2 | 349.7 | 739.0 |
| 8.10.3F | IgG1_D265A | 201.4 | 79.5 |

All antibodies tested efficiently blocked the bioactivity of M-CSF present in MDA-MB-231-conditioned medium. Prior art antibody 8.10.3F was less potent than the other antibodies tested. Similarly, all antibodies inhibited the bioactivity of M-CSF present in human serum. Again, prior art antibody 8.10.3F was less potent than the other immunoglobulins tested.

Example 8: Inhibition of Proliferation Induced by Cell Surface M-CSF

The ability of the antibodies of the present disclosure to block the bioactivity of membrane-bound M-CSF isoforms was assessed in an assay in which proliferation of M-NFS-60 cells was induced by CHO cells stably expressing human cell-surface M-CSF (CHO_hM-CSF cells). 2000 CHO_hM-CSF cells per well were cultured overnight at 37° C. in cell-culture 96 well plates, washed twice with PBS and fixed with 100 μl 2% glutaraldehyde/PBS per well for 30 min at 37° C. After washing with PBS, fixed cells were incubated with anti-M-CSF antibodies (final IgG concentrations 0.05 nM, 0.5 nM, 5 nM, 50 nM) for 30 min at 37° C. Subsequently, 5000 M-NFS-60 cells per well were added and cultivated for 72 h at 37° C. before cell viability was determined as described above. Results are shown in FIG. 1.

All M-CSF-specific immunoglobulins efficiently inhibited proliferation induced by CHO cells expressing M-CSF. The degree of inhibition increase with an increasing concentration of IgG. Inhibition was almost 100% at the highest IgG concentration tested (50 nM). MOR3207, an antibody with specificity to lysozyme, did not inhibit proliferation.

Example 9: Affinity Determination

The monovalent affinity of the antibodies of the present disclosure was determined by soluble equilibrium titration (Haenel et al. (2005) Anal Biochem 339, 182-4). The antibodies were purified in Fab format and K$_D$ to human and cynomolgus M-CSF was determined. The results are shown in Table 10. All values are in [pM].

TABLE 10

Monovalent affinities (K$_D$ values) of antibodies as determined by SET

| Antibody# | Human M-CSF | Cynomolgus M-CSF |
|---|---|---|
| Blanche | 96 | 130 |
| Caline | 14 | 16 |
| Camille | 18 | 25 |
| Celine | n.d. | n.d. |
| Laurine | 96 | 150 |
| Madeleine | 28 | 30 |
| Maelle | 13 | 27 |
| Meriem | 11 | 13 |
| Romaine | 13 | 7 |
| Satine | <2 | n.d. |
| Servane | n.d. | n.d. |
| HeRX1-10G1 | >1,000 | n.d. |
| 8.10.3F | 38 | n.d. |

As shown in Table 10 all Fabs tested bound to human and cynomolgus M-CSF. Intriguingly, most antibodies demonstrated K$_D$ values of 30 pM or lower, i.e. affinities which are higher than those of prior art antibodies HeRX1-10G1 and 8.10.3F. There was no significant difference observed in affinity between human and cynomolgus M-CSF.

Example 10: Specificity of the Antibodies

The specificity of binding of the antibodies of the present invention was exemplary tested with antibody Camille as described in Frese et al. (2013) MAbs, February 14; 5(2) [Epub ahead of print]. For this specificity profiling test the different proteins and controls were coated on two 384-well MSD plates with a concentration of 1 μg/ml at 4° C. over night. Plates were blocked with BSA and washed three times with PBS with 0.05% (v/v) Tween 20. Antibody samples were diluted to 100 nM and 10 nM in assay buffer (PBS with 0.5% (w/v) BSA, 0.05% (v/v) Tween 20). As controls, an unspecific antibody (MOR03207; anti-lysozym) and assay buffer were used. Samples and controls were incubated for three hours at room temperature. The plates were washed three times and 30 μl detection antibody (ECL-labeled anti-human Fab) were added per well and incubated for 1 h. After washing, MSD Read Buffer T with surfactant was added and electrochemiluminescence signals were detected using a Sector Imager 6000 (Meso Scale Discovery, Gaithersburg, Md., USA).

For evaluation, signals of the antibody sample on a certain protein were normalized to the reference antibody MOR03027. Results are shown in Table 11.

TABLE 11

Specificity of antibody Camille

| Target antigen | Antibody Camille 100 nM | 10 nM |
|---|---|---|
| Blank | 1 | 1 |
| Protein A (*Staphylococcus aureus*) | 1 | 1 |
| Serum albumin (human) | 1 | 1 |
| Fibrinogen (bovine) | 1 | 1 |
| Haemoglobin (human) | 1 | 1 |
| Transferrin (bovine) | 1 | 1 |
| Antitrypsin (human) | 1 | 1 |
| Lysozyme (chicken) | 0 | 0 |
| Cell surface receptor 1 (human) | 1 | 1 |
| Cytokine 1 (human) | 1 | 1 |
| Cytokine 2 (human) | 2 | 1 |
| Cell surface receptor 2 (human) | 1 | 1 |
| M-CSF (human) | 24 | 244 |
| Cell surface receptor 3 (human) | 1 | 1 |
| Blank | 2 | 1 |
| Pepsinogen (pork) | 1 | 1 |
| Aminogylcosidase (*Aspergillus niger*) | 1 | 1 |
| Trypsin inhibitor (Soybean) | 1 | 1 |
| Cytochrome c (cow) | 1 | 1 |
| Myoglobin (horse) | 1 | 1 |
| Lectin (*Lens culinaris*) | 1 | 1 |
| Ovalbumin (chicken) | 1 | 1 |
| Trypsinogen (cow) | 1 | 1 |
| Milk powder (cow) | 1 | 1 |
| RNase B (cow) | 1 | 1 |
| RNase A (cow) | 1 | 1 |
| Anti-human Fab (Dianova, # 109-005-097) | 1 | 1 |
| Anti-human Fc (Dianova, #109-005-098) | 1 | 1 |
| blank | 1 | 1 |

Exemplary antibody Camille was highly specific for M-CSF and did not show unspecific binding to any of the unrelated proteins tested in this assay.

Example 11: Comparison of Exemplary Antibody Camille with the Prior Art Antibodies In the following Table the key features of antibody Camille are compared to the prior art antibodies HeRX1.10G1 and 8.10.3F.

TABLE 12

Comparison of antibody Camille to the antibodies in the prior art

| | Criterion | | Camille | HeRX1.10G1 | 8.10.F3 |
|---|---|---|---|---|---|
| Binding | Human M-CSF | | 18 pM | >1,000 pM | 38 pM |
| | Cynomolgus M-CSF | | 25 pM | n.d. | n.d. |
| | IL-34, GM-CSF, SCF | | no | no | no |
| | Membrane-bound M-CSF | | yes | yes | yes |
| Functionality | Receptor binding assay (IC50) | Human M-CSF | 4 pM | 27 pM | 31 pM |
| | | Cynomolgus M-CSF | 6 pM | 28 pM | 21 pM |
| | Cell viability assay (IC50) | Human M-CSF | 2 pM | 4 pM | 71 pM |
| | | Cynomolgus M-CSF | 3 pM | 4 pM | 85 pM |
| | | Membrane-bound M-CSF | yes | yes | yes |
| | | MDA-MB-231 | 99 pM | 90 pM | 739 pM |
| | | Human serum M-CSF | 18 pM | 15 pM | 350 pM |

In summary, antibody Camille, as well as the other antibodies of the present disclosure, shows a binding affinity which is superior to all the prior art antibodies. This is also reflected in the functional assays, in which Camille performs at least as good as, but in most assays better than, the prior art antibodies HeRX1.10G1 and 8.10.F3.

Example 12: Efficacy of the Antibodies in a Clinical Trial

A multi-center, randomized, double-blinded, placebo-controlled study to evaluate the safety, preliminary clinical activity and immunogenicity of multiple doses of the antibodies of the present disclosure administered intravenously to patients with active rheumatoid arthritis will be conducted.

Primary outcome measures are the adverse event rate and the safety profile. Secondary outcome measures included DAS28 scores, ACR scores and EULAR28 response criteria.

The clinical trial comprises three treatment arms. In each treatment arm patients receive either placebo or the antibodies of the present disclosure (0.3 mg/kg body weight for treatment arm 1, 1.0 mg/kg body weight for treatment arm 2 and 1.5 mg/kg body weight for treatment arm 3). Antibodies and placebo are administered intravenously, weekly with 4 doses in total.

Prior to administration the disease activity of all patients is measured according to accepted guidelines by calculating the DAS28 score, a 28-joint Disease Activity Score (see e.g. Ann Rheum Dis (2009) 68, 954-60). DAS28 score is a validated and commonly used tool to quantify the disease status of RA patients. The average DAS28 score is comparable for all treatment arms.

The antibodies of the present disclosure show a favorable safety profile among all doses tested and the treatment is safe.

4 weeks and 8 weeks after the first administration of the antibodies or placebo the DAS28 scores of all patients is determined. A decrease in DAS28 scores correlates to diminished disease severity.

All patients treated with the antibodies of the present disclosure show a decrease in DAS28 scores, indicating less severity of the disease of effectiveness of the treatment. In contrast, patients treated with placebo showed do not show any benefit from treatment.

As another measure of efficacy the ACR20 criteria were used. ACR criteria measure improvement in tender or swollen joint counts and improvement in certain other parameters. The procedure to measure ACR scores is highly standardized. The present clinical trial applied the respective guidelines of the EMEA.

In line with the results of the DAS28 scores, also the ACR scores show a strong clinical improvement of patients' condition upon treatment with the antibodies of the present disclosure. The improvement after 4 weeks is highly significant.

What is claimed is:

1. A method for inhibiting a bioactivity of M-CSF in a patient, said method comprising administering to the patient an antibody or antibody fragment which specifically binds to M-CSF, wherein said antibody or antibody fragment is able to inhibit the binding of M-CSF to the M-CSF receptor with an IC50 of 10 pM or less in a receptor binding inhibition assay comprising M-CSF at a final concentration of 12.5 pM,
   wherein the antibody or antibody fragment comprises:
   (a) the HCDR1 region of SEQ ID NO:8, the HCDR2 region of SEQ ID NO:9, the HCDR3 region of SEQ ID NO:10, the LCDR1 region of SEQ ID NO:11, the LCDR2 region of SEQ ID NO:12 and the LCDR3 region of SEQ ID NO: 13,
   (b) the HCDR1 region of SEQ ID NO:18, the HCDR2 region of SEQ ID NO:19, the HCDR3 region of SEQ ID NO:20, the LCDR1 region of SEQ ID NO:21, the LCDR2 region of SEQ ID NO:22 and the LCDR3 region of SEQ ID NO:23, or
   (c) the HCDR1 region of SEQ ID NO:28, the HCDR2 region of SEQ ID NO:29, the HCDR3 region of SEQ ID NO:30, the LCDR1 region of SEQ ID NO:31, the LCDR2 region of SEQ ID NO:32 and the LCDR3 region of SEQ ID NO:33, and
   wherein the bioactivity of M-CSF is M-CSF induced proliferation.

2. The method of claim 1 wherein the antibody or antibody fragment comprises
   (a) the variable heavy region of SEQ ID NO:14 and the variable light region of SEQ ID NO:15,
   (b) the variable heavy region of SEQ ID NO:24 and the variable light region of SEQ ID NO:25, or
   (c) the variable heavy region of SEQ ID NO:34 and the variable light region of SEQ ID NO:35.

3. The method of claim 1, wherein the antibody or antibody fragment administered is of a lgG I subtype which has an effector function which is diminished compared to the wild type lgG I subtype.

4. The method of claim 3, wherein an aspartic acid residue at position 265 of said antibody (numbering according to the EU index) is exchanged for an alanine residue.

5. The method of claim 1 wherein the antibody or antibody fragment administered is a monoclonal antibody or a polyclonal antibody.

6. The method of claim 1 wherein the antibody or antibody fragment administered is a human, humanized or chimeric antibody.

7. The method of claim 1 wherein the antibody or antibody fragment administered is cross-reactive to cynomolgus M-CSF, mouse M-CSF and/or rat M-CSF.

8. The method of claim 1 wherein the patient is suffering from an inflammatory disorder.

9. The method of claim 1 wherein the patient is suffering from an inflammatory disorder and administration of the antibody or antibody fragment alleviating inflammation in the patient.

10. The method of claim 9 wherein the patient is suffering from rheumatoid arthritis.

* * * * *

SEQUENCE LISTING

```
<160> NUMBER OF SEQ ID NOS: 137

<210> SEQ ID NO 1
<211> LENGTH: 554
<212> TYPE: PRT
<213> ORGANISM: Homo sapiens

<400> SEQUENCE: 1

Met Thr Ala Pro Gly Ala Ala Gly Arg Cys Pro Pro Thr Thr Trp Leu
1               5                   10                  15

Gly Ser Leu Leu Leu Leu Val Cys Leu Leu Ala Ser Arg Ser Ile Thr
            20                  25                  30

Glu Glu Val Ser Glu Tyr Cys Ser His Met Ile Gly Ser Gly His Leu
        35                  40                  45

Gln Ser Leu Gln Arg Leu Ile Asp Ser Gln Met Glu Thr Ser Cys Gln
    50                  55                  60

Ile Thr Phe Glu Phe Val Asp Gln Glu Gln Leu Lys Asp Pro Val Cys
65                  70                  75                  80

Tyr Leu Lys Lys Ala Phe Leu Leu Val Gln Asp Ile Met Glu Asp Thr
                85                  90                  95

Met Arg Phe Arg Asp Asn Thr Pro Asn Ala Ile Ala Ile Val Gln Leu
            100                 105                 110

Gln Glu Leu Ser Leu Arg Leu Lys Ser Cys Phe Thr Lys Asp Tyr Glu
        115                 120                 125

Glu His Asp Lys Ala Cys Val Arg Thr Phe Tyr Glu Thr Pro Leu Gln
    130                 135                 140

Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
                165                 170                 175

Glu Cys Ser Ser Gln Asp Val Val Thr Lys Pro Asp Cys Asn Cys Leu
            180                 185                 190

Tyr Pro Lys Ala Ile Pro Ser Ser Asp Pro Ala Ser Val Ser Pro His
        195                 200                 205

Gln Pro Leu Ala Pro Ser Met Ala Pro Val Ala Gly Leu Thr Trp Glu
    210                 215                 220

Asp Ser Glu Gly Thr Glu Gly Ser Ser Leu Leu Pro Gly Glu Gln Pro
```

```
            225                 230                 235                 240
Leu His Thr Val Asp Pro Gly Ser Ala Lys Gln Arg Pro Pro Arg Ser
                245                 250                 255

Thr Cys Gln Ser Phe Glu Pro Glu Thr Pro Val Val Lys Asp Ser
                260                 265                 270

Thr Ile Gly Gly Ser Pro Gln Pro Arg Pro Ser Val Gly Ala Phe Asn
                275                 280                 285

Pro Gly Met Glu Asp Ile Leu Asp Ser Ala Met Gly Thr Asn Trp Val
            290                 295                 300

Pro Glu Glu Ala Ser Gly Glu Ala Ser Glu Ile Pro Val Pro Gln Gly
305                 310                 315                 320

Thr Glu Leu Ser Pro Ser Arg Pro Gly Gly Gly Ser Met Gln Thr Glu
                325                 330                 335

Pro Ala Arg Pro Ser Asn Phe Leu Ser Ala Ser Ser Pro Leu Pro Ala
                340                 345                 350

Ser Ala Lys Gly Gln Gln Pro Ala Asp Val Thr Gly Thr Ala Leu Pro
                355                 360                 365

Arg Val Gly Pro Val Arg Pro Thr Gly Gln Asp Trp Asn His Thr Pro
            370                 375                 380

Gln Lys Thr Asp His Pro Ser Ala Leu Leu Arg Asp Pro Pro Glu Pro
385                 390                 395                 400

Gly Ser Pro Arg Ile Ser Ser Leu Arg Pro Gln Gly Leu Ser Asn Pro
                405                 410                 415

Ser Thr Leu Ser Ala Gln Pro Gln Leu Ser Arg Ser His Ser Ser Gly
                420                 425                 430

Ser Val Leu Pro Leu Gly Glu Leu Glu Gly Arg Arg Ser Thr Arg Asp
                435                 440                 445

Arg Arg Ser Pro Ala Glu Pro Glu Gly Gly Pro Ala Ser Glu Gly Ala
            450                 455                 460

Ala Arg Pro Leu Pro Arg Phe Asn Ser Val Pro Leu Thr Asp Thr Gly
465                 470                 475                 480

His Glu Arg Gln Ser Glu Gly Ser Phe Ser Pro Gln Leu Gln Glu Ser
                485                 490                 495

Val Phe His Leu Leu Val Pro Ser Val Ile Leu Val Leu Leu Ala Val
                500                 505                 510

Gly Gly Leu Leu Phe Tyr Arg Trp Arg Arg Arg Ser His Gln Glu Pro
                515                 520                 525

Gln Arg Ala Asp Ser Pro Leu Glu Gln Pro Glu Gly Ser Pro Leu Thr
            530                 535                 540

Gln Asp Asp Arg Gln Val Glu Leu Pro Val
545                 550

<210> SEQ ID NO 2
<211> LENGTH: 223
<212> TYPE: PRT
<213> ORGANISM: Homo sapiens

<400> SEQUENCE: 2

Glu Glu Val Ser Glu Tyr Cys Ser His Met Ile Gly Ser Gly His Leu
1               5                   10                  15

Gln Ser Leu Gln Arg Leu Ile Asp Ser Gln Met Glu Thr Ser Cys Gln
                20                  25                  30

Ile Thr Phe Glu Phe Val Asp Gln Glu Gln Leu Lys Asp Pro Val Cys
            35                  40                  45
```

Tyr Leu Lys Lys Ala Phe Leu Leu Val Gln Asp Ile Met Glu Asp Thr
 50                  55                  60

Met Arg Phe Arg Asp Asn Thr Pro Asn Ala Ile Ala Ile Val Gln Leu
 65                  70                  75                  80

Gln Glu Leu Ser Leu Arg Leu Lys Ser Cys Phe Thr Lys Asp Tyr Glu
                 85                  90                  95

Glu His Asp Lys Ala Cys Val Arg Thr Phe Tyr Glu Thr Pro Leu Gln
                100                 105                 110

Leu Leu Glu Lys Val Lys Asn Val Phe Asn Glu Thr Lys Asn Leu Leu
                115                 120                 125

Asp Lys Asp Trp Asn Ile Phe Ser Lys Asn Cys Asn Asn Ser Phe Ala
130                 135                 140

Glu Cys Ser Ser Gln Asp Val Val Thr Lys Pro Asp Cys Asn Cys Leu
145                 150                 155                 160

Tyr Pro Lys Ala Ile Pro Ser Ser Asp Pro Ala Ser Val Ser Pro His
                165                 170                 175

Gln Pro Leu Ala Pro Ser Met Ala Pro Val Ala Gly Leu Thr Trp Glu
                180                 185                 190

Asp Ser Glu Gly Thr Glu Gly Ser Ser Leu Leu Pro Gly Glu Gln Pro
                195                 200                 205

Leu His Thr Val Asp Pro Gly Ser Ala Lys Gln Arg Pro Pro Arg
210                 215                 220

<210> SEQ ID NO 3
<211> LENGTH: 456
<212> TYPE: PRT
<213> ORGANISM: Homo sapiens

<400> SEQUENCE: 3

Glu Glu Val Ser Glu Tyr Cys Ser His Met Ile Gly Ser Gly His Leu
 1               5                  10                  15

Gln Ser Leu Gln Arg Leu Ile Asp Ser Gln Met Glu Thr Ser Cys Gln
                 20                  25                  30

Ile Thr Phe Glu Phe Val Asp Gln Glu Gln Leu Lys Asp Pro Val Cys
                 35                  40                  45

Tyr Leu Lys Lys Ala Phe Leu Leu Val Gln Asp Ile Met Glu Asp Thr
 50                  55                  60

Met Arg Phe Arg Asp Asn Thr Pro Asn Ala Ile Ala Ile Val Gln Leu
 65                  70                  75                  80

Gln Glu Leu Ser Leu Arg Leu Lys Ser Cys Phe Thr Lys Asp Tyr Glu
                 85                  90                  95

Glu His Asp Lys Ala Cys Val Arg Thr Phe Tyr Glu Thr Pro Leu Gln
                100                 105                 110

Leu Leu Glu Lys Val Lys Asn Val Phe Asn Glu Thr Lys Asn Leu Leu
                115                 120                 125

Asp Lys Asp Trp Asn Ile Phe Ser Lys Asn Cys Asn Asn Ser Phe Ala
130                 135                 140

Glu Cys Ser Ser Gln Asp Val Val Thr Lys Pro Asp Cys Asn Cys Leu
145                 150                 155                 160

Tyr Pro Lys Ala Ile Pro Ser Ser Asp Pro Ala Ser Val Ser Pro His
                165                 170                 175

Gln Pro Leu Ala Pro Ser Met Ala Pro Val Ala Gly Leu Thr Trp Glu
                180                 185                 190

Asp Ser Glu Gly Thr Glu Gly Ser Ser Leu Leu Pro Gly Glu Gln Pro
                195                 200                 205

```
Leu His Thr Val Asp Pro Gly Ser Ala Lys Gln Arg Pro Pro Arg Ser
210                 215                 220

Thr Cys Gln Ser Phe Glu Pro Pro Glu Thr Pro Val Val Lys Asp Ser
225                 230                 235                 240

Thr Ile Gly Gly Ser Pro Gln Pro Arg Pro Ser Val Gly Ala Phe Asn
                245                 250                 255

Pro Gly Met Glu Asp Ile Leu Asp Ser Ala Met Gly Thr Asn Trp Val
            260                 265                 270

Pro Glu Glu Ala Ser Gly Glu Ala Ser Glu Ile Pro Val Pro Gln Gly
        275                 280                 285

Thr Glu Leu Ser Pro Ser Arg Pro Gly Gly Ser Met Gln Thr Glu
290                 295                 300

Pro Ala Arg Pro Ser Asn Phe Leu Ser Ala Ser Ser Pro Leu Pro Ala
305                 310                 315                 320

Ser Ala Lys Gly Gln Gln Pro Ala Asp Val Thr Gly Thr Ala Leu Pro
                325                 330                 335

Arg Val Gly Pro Val Arg Pro Thr Gly Gln Asp Trp Asn His Thr Pro
            340                 345                 350

Gln Lys Thr Asp His Pro Ser Ala Leu Leu Arg Asp Pro Pro Glu Pro
        355                 360                 365

Gly Ser Pro Arg Ile Ser Ser Leu Arg Pro Gln Gly Leu Ser Asn Pro
370                 375                 380

Ser Thr Leu Ser Ala Gln Pro Gln Leu Ser Arg Ser His Ser Ser Gly
385                 390                 395                 400

Ser Val Leu Pro Leu Gly Glu Leu Glu Gly Arg Arg Ser Thr Arg Asp
                405                 410                 415

Arg Arg Ser Pro Ala Glu Pro Glu Gly Gly Pro Ala Ser Glu Gly Ala
            420                 425                 430

Ala Arg Pro Leu Pro Arg Phe Asn Ser Val Pro Leu Thr Asp Thr Gly
        435                 440                 445

His Glu Arg Gln Ser Glu Gly Ser
450                 455

<210> SEQ ID NO 4
<211> LENGTH: 224
<212> TYPE: PRT
<213> ORGANISM: Homo sapiens

<400> SEQUENCE: 4

Glu Glu Val Ser Glu Tyr Cys Ser His Met Ile Gly Ser Gly His Leu
1               5                   10                  15

Gln Ser Leu Gln Arg Leu Ile Asp Ser Gln Met Glu Thr Ser Cys Gln
            20                  25                  30

Ile Thr Phe Glu Phe Val Asp Gln Glu Gln Leu Lys Asp Pro Val Cys
        35                  40                  45

Tyr Leu Lys Lys Ala Phe Leu Leu Val Gln Asp Ile Met Glu Asp Thr
    50                  55                  60

Met Arg Phe Arg Asp Asn Thr Pro Asn Ala Ile Ala Ile Val Gln Leu
65                  70                  75                  80

Gln Glu Leu Ser Leu Arg Leu Lys Ser Cys Phe Thr Lys Asp Tyr Glu
                85                  90                  95

Glu His Asp Lys Ala Cys Val Arg Thr Phe Tyr Glu Thr Pro Leu Gln
            100                 105                 110

Leu Leu Glu Lys Val Lys Asn Val Phe Asn Glu Thr Lys Asn Leu Leu
```

```
                    115                 120                 125
Asp Lys Asp Trp Asn Ile Phe Ser Lys Asn Cys Asn Asn Ser Phe Ala
        130                 135                 140

Glu Cys Ser Ser Gln Gly His Glu Arg Gln Ser Gly Ser Ser Ser
145                 150                 155                 160

Pro Gln Leu Gln Glu Ser Val Phe His Leu Leu Val Pro Ser Val Ile
                    165                 170                 175

Leu Val Leu Leu Ala Val Gly Gly Leu Leu Phe Tyr Arg Trp Arg Arg
                180                 185                 190

Arg Ser His Gln Glu Pro Gln Arg Ala Asp Ser Pro Leu Glu Gln Pro
            195                 200                 205

Glu Gly Ser Pro Leu Thr Gln Asp Asp Arg Gln Val Glu Leu Pro Val
        210                 215                 220

<210> SEQ ID NO 5
<211> LENGTH: 158
<212> TYPE: PRT
<213> ORGANISM: Homo sapiens

<400> SEQUENCE: 5

Glu Glu Val Ser Glu Tyr Cys Ser His Met Ile Gly Ser Gly His Leu
1               5                   10                  15

Gln Ser Leu Gln Arg Leu Ile Asp Ser Gln Met Glu Thr Ser Cys Gln
                20                  25                  30

Ile Thr Phe Glu Phe Val Asp Gln Glu Gln Leu Lys Asp Pro Val Cys
            35                  40                  45

Tyr Leu Lys Lys Ala Phe Leu Leu Val Gln Asp Ile Met Glu Asp Thr
        50                  55                  60

Met Arg Phe Arg Asp Asn Thr Pro Asn Ala Ile Ala Ile Val Gln Leu
65                  70                  75                  80

Gln Glu Leu Ser Leu Arg Leu Lys Ser Cys Phe Thr Lys Asp Tyr Glu
                85                  90                  95

Glu His Asp Lys Ala Cys Val Arg Thr Phe Tyr Glu Thr Pro Leu Gln
            100                 105                 110

Leu Leu Glu Lys Val Lys Asn Val Phe Asn Glu Thr Lys Asn Leu Leu
        115                 120                 125

Asp Lys Asp Trp Asn Ile Phe Ser Lys Asn Cys Asn Asn Ser Phe Ala
    130                 135                 140

Glu Cys Ser Ser Gln Asp Val Val Thr Lys Pro Asp Cys Asn
145                 150                 155

<210> SEQ ID NO 6
<211> LENGTH: 223
<212> TYPE: PRT
<213> ORGANISM: Macaca fascicularis

<400> SEQUENCE: 6

Glu Glu Val Ser Glu Tyr Cys Ser His Met Ile Gly Ser Gly His Leu
1               5                   10                  15

Gln Ser Leu Gln Arg Leu Ile Asp Ser Gln Met Glu Thr Ser Cys Gln
                20                  25                  30

Ile Thr Phe Glu Phe Val Asp Gln Glu Gln Leu Lys Asp Pro Val Cys
            35                  40                  45

Tyr Leu Lys Lys Ala Phe Leu Leu Val Gln Asp Ile Met Glu Asp Thr
        50                  55                  60

Met Arg Phe Arg Asp Asn Thr Pro Asn Ala Ile Ala Ile Val Gln Leu
65                  70                  75                  80
```

Gln Glu Leu Ser Leu Arg Leu Lys Ser Cys Phe Thr Lys Asp Tyr Glu
                85                  90                  95

Glu His Asp Lys Ala Cys Val Arg Thr Phe Tyr Glu Thr Pro Leu Gln
            100                 105                 110

Leu Leu Glu Lys Val Lys Asn Val Phe Asn Glu Thr Lys Asn Leu Leu
        115                 120                 125

Asp Lys Asp Trp Asn Ile Phe Ser Lys Asn Cys Asn Asn Ser Phe Ala
    130                 135                 140

Glu Cys Ser Ser Gln Asp Val Val Thr Lys Pro Asp Cys Asn Cys Leu
145                 150                 155                 160

Tyr Pro Lys Ala Ile Pro Ser Ser Asp Pro Ala Ser Val Ser Pro His
                165                 170                 175

Gln Pro Leu Ala Pro Ser Met Ala Pro Met Ala Gly Leu Thr Trp Asp
            180                 185                 190

Asp Ser Glu Gly Thr Glu Gly Ser Ser Leu Leu Pro Gly Glu Gln Pro
        195                 200                 205

Leu His Thr Val Asp Pro Gly Ser Ala Lys Gln Arg Pro Pro Arg
    210                 215                 220

<210> SEQ ID NO 7
<211> LENGTH: 972
<212> TYPE: PRT
<213> ORGANISM: Homo sapiens

<400> SEQUENCE: 7

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
            20                  25                  30

Lys Pro Gly Ala Thr Val Thr Leu Arg Cys Val Gly Asn Gly Ser Val
        35                  40                  45

Glu Trp Asp Gly Pro Pro Ser Pro His Trp Thr Leu Tyr Ser Asp Gly
    50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
        115                 120                 125

Leu Thr Asp Pro Val Leu Glu Ala Gly Val Ser Leu Val Arg Val Arg
    130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Pro Ala Leu Thr Leu Val
        195                 200                 205

Pro Ala Glu Leu Val Arg Ile Arg Gly Glu Ala Ala Gln Ile Val Cys
    210                 215                 220

Ser Ala Ser Ser Val Asp Val Asn Phe Asp Val Phe Leu Gln His Asn

```
                225                 230                 235                 240
Asn Thr Lys Leu Ala Ile Pro Gln Gln Ser Asp Phe His Asn Asn Arg
                    245                 250                 255

Tyr Gln Lys Val Leu Thr Leu Asn Leu Asp Gln Val Asp Phe Gln His
                    260                 265                 270

Ala Gly Asn Tyr Ser Cys Val Ala Ser Asn Val Gln Gly Lys His Ser
                    275                 280                 285

Thr Ser Met Phe Phe Arg Val Val Glu Ser Ala Tyr Leu Asn Leu Ser
        290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                        325                 330                 335

Thr Tyr Leu Gly Pro Phe Ser Asp His Gln Pro Glu Pro Lys Leu Ala
                340                 345                 350

Asn Ala Thr Thr Lys Asp Thr Tyr Arg His Thr Phe Thr Leu Ser Leu
                355                 360                 365

Pro Arg Leu Lys Pro Ser Glu Ala Gly Arg Tyr Ser Phe Leu Ala Arg
        370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                    405                 410                 415

Leu Leu Cys Ala Ala Ser Gly Tyr Pro Gln Pro Asn Val Thr Trp Leu
                420                 425                 430

Gln Cys Ser Gly His Thr Asp Arg Cys Asp Glu Ala Gln Val Leu Gln
            435                 440                 445

Val Trp Asp Asp Pro Tyr Pro Glu Val Leu Ser Gln Glu Pro Phe His
        450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                    485                 490                 495

Ala Phe Ile Pro Ile Ser Ala Gly Ala His Thr His Pro Pro Asp Glu
                500                 505                 510

Phe Leu Phe Thr Pro Val Val Ala Cys Met Ser Ile Met Ala Leu
            515                 520                 525

Leu Leu Leu Leu Leu Leu Leu Leu Tyr Lys Tyr Lys Gln Lys Pro
        530                 535                 540

Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
                    565                 570                 575

Phe Pro Arg Asn Asn Leu Gln Phe Gly Lys Thr Leu Gly Ala Gly Ala
                580                 585                 590

Phe Gly Lys Val Val Glu Ala Thr Ala Phe Gly Leu Gly Lys Glu Asp
            595                 600                 605

Ala Val Leu Lys Val Ala Val Lys Met Leu Lys Ser Thr Ala His Ala
        610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                    645                 650                 655
```

-continued

```
Gly Pro Val Leu Val Ile Thr Glu Tyr Cys Cys Tyr Gly Asp Leu Leu
            660                 665                 670

Asn Phe Leu Arg Arg Lys Ala Glu Ala Met Leu Gly Pro Ser Leu Ser
            675                 680                 685

Pro Gly Gln Asp Pro Glu Gly Gly Val Asp Tyr Lys Asn Ile His Leu
        690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
                    725                 730                 735

Phe Ser Glu Gln Asp Leu Asp Lys Glu Asp Gly Arg Pro Leu Glu Leu
            740                 745                 750

Arg Asp Leu Leu His Phe Ser Ser Gln Val Ala Gln Gly Met Ala Phe
            755                 760                 765

Leu Ala Ser Lys Asn Cys Ile His Arg Asp Val Ala Ala Arg Asn Val
770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
                    805                 810                 815

Leu Pro Val Lys Trp Met Ala Pro Glu Ser Ile Phe Asp Cys Val Tyr
                820                 825                 830

Thr Val Gln Ser Asp Val Trp Ser Tyr Gly Ile Leu Leu Trp Glu Ile
            835                 840                 845

Phe Ser Leu Gly Leu Asn Pro Tyr Pro Gly Ile Leu Val Asn Ser Lys
850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
                    885                 890                 895

Pro Thr His Arg Pro Thr Phe Gln Gln Ile Cys Ser Phe Leu Gln Glu
                900                 905                 910

Gln Ala Gln Glu Asp Arg Arg Glu Arg Asp Tyr Thr Asn Leu Pro Ser
            915                 920                 925

Ser Ser Arg Ser Gly Gly Ser Gly Ser Ser Ser Glu Leu Glu Glu
            930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
                    965                 970
```

<210> SEQ ID NO 8
<211> LENGTH: 7
<212> TYPE: PRT
<213> ORGANISM: Artificial Sequence
<220> FEATURE:
<223> OTHER INFORMATION: Synthetic peptide

<400> SEQUENCE: 8

```
Ser Asn Ser Ala Ala Trp Asn
1               5
```

<210> SEQ ID NO 9
<211> LENGTH: 18
<212> TYPE: PRT
<213> ORGANISM: Artificial Sequence
<220> FEATURE:
<223> OTHER INFORMATION: Synthetic peptide

<400> SEQUENCE: 9

Arg Thr Tyr Tyr Arg Ser Lys Trp Lys His Glu Tyr Ala Met Ser Val
1               5                   10                  15

Lys Ser

<210> SEQ ID NO 10
<211> LENGTH: 10
<212> TYPE: PRT
<213> ORGANISM: Artificial Sequence
<220> FEATURE:
<223> OTHER INFORMATION: Synthetic peptide

<400> SEQUENCE: 10

Asp Arg Tyr Tyr Tyr Ser Ala Phe Asp Tyr
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Synthetic peptide

<400> SEQUENCE: 11

Thr Gly Thr Ser Ser Asp Val Gly Gly Tyr Asn Ser Val Ser
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Synthetic peptide

<400> SEQUENCE: 12

Ala Val Ser Asn Arg Pro Ser
1               5

<210> SEQ ID NO 13
<211> LENGTH: 10
<212> TYPE: PRT
<213> ORGANISM: Artificial Sequence
<220> FEATURE:
<223> OTHER INFORMATION: Synthetic peptide

<400> SEQUENCE: 13

Ala Ser Tyr Asp Glu Arg Phe Thr Arg Val
1               5                   10

<210> SEQ ID NO 14
<211> LENGTH: 122
<212> TYPE: PRT
<213> ORGANISM: Artificial Sequence
<220> FEATURE:
<223> OTHER INFORMATION: Synthetic peptide

<400> SEQUENCE: 14

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu

```
                    35                  40                  45
Trp Leu Gly Arg Thr Tyr Tyr Arg Ser Lys Trp Lys His Glu Tyr Ala
        50                  55                  60

Met Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Arg Tyr Tyr Tyr Ser Ala Phe Asp Tyr Trp
            100                 105                 110

Gly Gln Gly Thr Leu Val Thr Val Ser Ser
        115                 120

<210> SEQ ID NO 15
<211> LENGTH: 112
<212> TYPE: PRT
<213> ORGANISM: Artificial Sequence
<220> FEATURE:
<223> OTHER INFORMATION: Synthetic peptide

<400> SEQUENCE: 15

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Met Ile Tyr Ala Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Asp Glu Arg
                85                  90                  95

Phe Thr Arg Val Phe Gly Gly Gly Thr Lys Leu Thr Val Leu Gly Gln
            100                 105                 110

<210> SEQ ID NO 16
<211> LENGTH: 366
<212> TYPE: DNA
<213> ORGANISM: Artificial Sequence
<220> FEATURE:
<223> OTHER INFORMATION: Synthetic peptide

<400> SEQUENCE: 16
caggtgcaat tgcagcagag cggtccgggc ctggtgaaac cgagccagac cctgagcctg      60
acctgcgcga tttccggcga tagtgtgagt agcaatagcg ctgcttggaa ctggattcgt     120
cagagcccga gccgtggcct cgagtggctg ggccgtacct actaccgtag caaatggaaa     180
catgaatatg ccatgagcgt gaaaagccgc attaccatta acccggatac ttcgaaaaac     240
cagtttagcc tgcaactgaa cagcgtgacc ccggaagata cggccgtgta ttattgcgcg     300
cgtgaccgtt actactactc tgctttcgat tactggggcc aaggcaccct ggtgactgtt     360
agctca                                                                366

<210> SEQ ID NO 17
<211> LENGTH: 336
<212> TYPE: DNA
<213> ORGANISM: Artificial Sequence
<220> FEATURE:
<223> OTHER INFORMATION: Synthetic peptide
```

```
<400> SEQUENCE: 17
caaagcgcgc tgacccagcc ggcgagcgtg agcggtagcc cgggccagag cattaccatt    60
agctgcaccg gcaccagcag cgatgtgggc ggttacaatt ctgtttcttg gtaccagcag   120
catccgggca aggcgccgaa attgatgatt tacgctgttt ctaaccgtcc gagcggcgtg   180
agcaaccgtt ttagcggatc caaaagcggc aacaccgcga gcctgaccat tagcggcctg   240
caagcggaag acgaagcgga ttattactgc gcttcttacg acgaacgttt cactcgtgtg   300
tttggcggcg gcacgaagtt aaccgtccta ggtcag                            336

<210> SEQ ID NO 18
<211> LENGTH: 7
<212> TYPE: PRT
<213> ORGANISM: Artificial Sequence
<220> FEATURE:
<223> OTHER INFORMATION: Synthetic peptide

<400> SEQUENCE: 18

Thr Ser Ser Ala Ala Trp Asn
1               5

<210> SEQ ID NO 19
<211> LENGTH: 18
<212> TYPE: PRT
<213> ORGANISM: Artificial Sequence
<220> FEATURE:
<223> OTHER INFORMATION: Synthetic peptide

<400> SEQUENCE: 19

Arg Thr Tyr Tyr Arg Ser Lys Trp Lys His Glu Tyr Ala Val Ser Val
1               5                   10                  15

Lys Ser

<210> SEQ ID NO 20
<211> LENGTH: 10
<212> TYPE: PRT
<213> ORGANISM: Artificial Sequence
<220> FEATURE:
<223> OTHER INFORMATION: Synthetic peptide

<400> SEQUENCE: 20

Asp Arg Tyr Tyr Tyr Ser Ala Phe Asp Tyr
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Synthetic peptide

<400> SEQUENCE: 21

Thr Gly Thr Ser Ser Asp Val Gly Gly Tyr Asn Ser Val Ser
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Synthetic peptide

<400> SEQUENCE: 22
```

```
Ala Val Ser Asn Arg Pro Ser
1               5
```

```
<210> SEQ ID NO 23
<211> LENGTH: 10
<212> TYPE: PRT
<213> ORGANISM: Artificial Sequence
<220> FEATURE:
<223> OTHER INFORMATION: Synthetic peptide

<400> SEQUENCE: 23

Ala Ser Tyr Asp Glu Arg Phe Thr Arg Val
1               5                   10
```

```
<210> SEQ ID NO 24
<211> LENGTH: 122
<212> TYPE: PRT
<213> ORGANISM: Artificial Sequence
<220> FEATURE:
<223> OTHER INFORMATION: Synthetic peptide

<400> SEQUENCE: 24

Gln Val Gln Leu Gln Gln Ser Gly Pro Gly Leu Val Lys Pro Ser Gln
1               5                   10                  15

Thr Leu Ser Leu Thr Cys Ala Ile Ser Gly Glu Ser Val Ser Thr Ser
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Lys His Glu Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Arg Tyr Tyr Tyr Ser Ala Phe Asp Tyr Trp
            100                 105                 110

Gly Gln Gly Thr Leu Val Thr Val Ser Ser
        115                 120
```

```
<210> SEQ ID NO 25
<211> LENGTH: 112
<212> TYPE: PRT
<213> ORGANISM: Artificial Sequence
<220> FEATURE:
<223> OTHER INFORMATION: Synthetic peptide

<400> SEQUENCE: 25

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Leu Ile Tyr Ala Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Asp Glu Arg
                85                  90                  95

Phe Thr Arg Val Phe Gly Gly Gly Thr Lys Leu Thr Val Leu Gly Gln
```

<210> SEQ ID NO 26
<211> LENGTH: 366
<212> TYPE: DNA
<213> ORGANISM: Artificial Sequence
<220> FEATURE:
<223> OTHER INFORMATION: Synthetic peptide

<400> SEQUENCE: 26

```
caggtgcaat tgcagcagag cggtccgggc ctggtgaaac cgagccagac cctgagcctg      60
acctgcgcga tttccggaga gagtgtgagc actagtagtg ctgcttggaa ctggattcgt     120
cagagcccga gccgtggcct cgagtggctg gccgtacct actaccgtag caaatggaaa     180
catgaatatg ccgtgagcgt gaaaagccgc attaccatta acccggatac ttcgaaaaac     240
cagtttagcc tgcaactgaa cagcgtgacc ccggaagata cggccgtgta ttattgcgcg     300
cgtgaccgtt actactactc tgctttcgat tactggggcc aaggcaccct ggtgactgtt     360
agctca                                                                366
```

<210> SEQ ID NO 27
<211> LENGTH: 336
<212> TYPE: DNA
<213> ORGANISM: Artificial Sequence
<220> FEATURE:
<223> OTHER INFORMATION: Synthetic peptide

<400> SEQUENCE: 27

```
caaagcgcgc tgacccagcc ggcgagcgtg agcggtagcc cgggccagag cattaccatt      60
agctgcaccg gcaccagcag cgatgtgggc ggttacaact ctgtttcttg gtaccagcag     120
catccgggca aggcgccgaa actgctgatt tacgctgttt ctaaccgtcc gagcggcgtg     180
agcaaccgtt ttagcggatc caaaagcggc aacaccgcga gcctgaccat tagcggcctg     240
caagcggaag acgaagcgga ttattactgc gcttcttacg acgaacgttt cactcgtgtg     300
tttggcggcg gcacgaagtt aaccgtccta ggtcag                               336
```

<210> SEQ ID NO 28
<211> LENGTH: 7
<212> TYPE: PRT
<213> ORGANISM: Artificial Sequence
<220> FEATURE:
<223> OTHER INFORMATION: Synthetic peptide

<400> SEQUENCE: 28

Thr Ser Ser Ala Ala Trp Asn
1               5

<210> SEQ ID NO 29
<211> LENGTH: 18
<212> TYPE: PRT
<213> ORGANISM: Artificial Sequence
<220> FEATURE:
<223> OTHER INFORMATION: Synthetic peptide

<400> SEQUENCE: 29

Arg Thr Tyr Tyr Arg Ser Lys Trp Lys His Glu Tyr Ala Val Ser Val
1               5                   10                  15

Lys Ser

<210> SEQ ID NO 30
<211> LENGTH: 10

```
<212> TYPE: PRT
<213> ORGANISM: Artificial Sequence
<220> FEATURE:
<223> OTHER INFORMATION: Synthetic peptide

<400> SEQUENCE: 30

Asp Arg Tyr Tyr Tyr Ser Ala Phe Asp Tyr
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Synthetic peptide

<400> SEQUENCE: 31

Thr Gly Thr Ser Ser Asp Val Gly Gly Tyr Asn Ser Val Ser
1               5                   10

<210> SEQ ID NO 32
<211> LENGTH: 7
<212> TYPE: PRT
<213> ORGANISM: Artificial Sequence
<220> FEATURE:
<223> OTHER INFORMATION: Synthetic peptide

<400> SEQUENCE: 32

Ala Val Ser Asn Arg Pro Ser
1               5

<210> SEQ ID NO 33
<211> LENGTH: 10
<212> TYPE: PRT
<213> ORGANISM: Artificial Sequence
<220> FEATURE:
<223> OTHER INFORMATION: Synthetic peptide

<400> SEQUENCE: 33

Ala Ser Tyr Asp Glu Arg Phe Thr Arg Val
1               5                   10

<210> SEQ ID NO 34
<211> LENGTH: 122
<212> TYPE: PRT
<213> ORGANISM: Artificial Sequence
<220> FEATURE:
<223> OTHER INFORMATION: Synthetic peptide

<400> SEQUENCE: 34

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Thr Ser
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Lys His Glu Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Arg Tyr Tyr Tyr Ser Ala Phe Asp Tyr Trp
            100                 105                 110
```

Gly Gln Gly Thr Leu Val Thr Val Ser Ser
        115                 120

<210> SEQ ID NO 35
<211> LENGTH: 112
<212> TYPE: PRT
<213> ORGANISM: Artificial Sequence
<220> FEATURE:
<223> OTHER INFORMATION: Synthetic peptide

<400> SEQUENCE: 35

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Ile Ile Tyr Ala Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Asp Glu Arg
                85                  90                  95

Phe Thr Arg Val Phe Gly Gly Gly Thr Lys Leu Thr Val Leu Gly Gln
            100                 105                 110

<210> SEQ ID NO 36
<211> LENGTH: 366
<212> TYPE: DNA
<213> ORGANISM: Artificial Sequence
<220> FEATURE:
<223> OTHER INFORMATION: Synthetic peptide

<400> SEQUENCE: 36
caggtgcaat tgcagcagag cggtccgggc ctggtgaaac cgagccagac cctgagcctg       60
acctgcgcga tttccggaga cagcgtgagt accagtagtg ctgcttggaa ctggattcgt      120
cagagcccga gccgtggcct cgagtggctg ggccgtacct actaccgtag caaatggaaa      180
catgaatatg ccgtgagcgt gaaaagccgc attaccatta cccggatac ttcgaaaaac       240 cagtttagcc tgcaactgaa cagcgtgacc ccggaagata cggccgtgta ttattgcgcg      300
cgtgaccgtt actactactc tgctttcgat tactggggcc aaggcaccct ggtgactgtt      360
agctca                                                                366

<210> SEQ ID NO 37
<211> LENGTH: 336
<212> TYPE: DNA
<213> ORGANISM: Artificial Sequence
<220> FEATURE:
<223> OTHER INFORMATION: Synthetic peptide

<400> SEQUENCE: 37
caaagcgcgc tgacccagcc ggcgagcgtg agcggtagcc cgggccagag cattaccatt       60
agctgcaccg gcaccagcag cgatgtgggc ggttacaact ctgtttcttg gtaccagcag      120
catccgggca aggcgccgaa actgatcatc tacgctgttt ctaaccgtcc gagcggcgtg      180
agcaaccgtt ttagcggatc caaaagcggc aacaccgcga gcctgaccat tagcggcctg      240
caagcggaag acgaagcgga ttattactgc gcttcttacg acgaacgttt cactcgtgtg      300
tttggcggcg gcacgaagtt aaccgtccta ggtcag                               336

<210> SEQ ID NO 38
<211> LENGTH: 7
<212> TYPE: PRT
<213> ORGANISM: Artificial Sequence
<220> FEATURE:
<223> OTHER INFORMATION: Synthetic peptide

<400> SEQUENCE: 38

```
Ser Asn Ser Ala Ala Trp Asn
1               5
```

<210> SEQ ID NO 39
<211> LENGTH: 18
<212> TYPE: PRT
<213> ORGANISM: Artificial Sequence
<220> FEATURE:
<223> OTHER INFORMATION: Synthetic peptide

<400> SEQUENCE: 39

```
Arg Thr Tyr Tyr Arg Ser Lys Trp Lys Lys Glu Tyr Ala Gln Ser Val
1               5                   10                  15

Lys Ser
```

<210> SEQ ID NO 40
<211> LENGTH: 10
<212> TYPE: PRT
<213> ORGANISM: Artificial Sequence
<220> FEATURE:
<223> OTHER INFORMATION: Synthetic peptide

<400> SEQUENCE: 40

```
Asp Arg Tyr Tyr Tyr Ser Ala Phe Asp Tyr
1               5                   10
```

<210> SEQ ID NO 41
<211> LENGTH: 14
<212> TYPE: PRT
<213> ORGANISM: Artificial Sequence
<220> FEATURE:
<223> OTHER INFORMATION: Synthetic peptide

<400> SEQUENCE: 41

```
Thr Gly Thr Ser Ser Asp Val Gly Gly Tyr Asn Ser Val Ser
1               5                   10
```

<210> SEQ ID NO 42
<211> LENGTH: 7
<212> TYPE: PRT
<213> ORGANISM: Artificial Sequence
<220> FEATURE:
<223> OTHER INFORMATION: Synthetic peptide

<400> SEQUENCE: 42

```
Ala Val Ser Asn Arg Pro Ser
1               5
```

<210> SEQ ID NO 43
<211> LENGTH: 10
<212> TYPE: PRT
<213> ORGANISM: Artificial Sequence
<220> FEATURE:
<223> OTHER INFORMATION: Synthetic peptide

<400> SEQUENCE: 43

Ala Ser Tyr Asp Glu Arg Phe Thr Arg Val
1               5                   10

<210> SEQ ID NO 44
<211> LENGTH: 122
<212> TYPE: PRT
<213> ORGANISM: Artificial Sequence
<220> FEATURE:
<223> OTHER INFORMATION: Synthetic peptide

<400> SEQUENCE: 44

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Lys Lys Glu Tyr Ala
    50                  55                  60

Gln Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
            85                  90                  95

Tyr Tyr Cys Ala Arg Asp Arg Tyr Tyr Tyr Ser Ala Phe Asp Tyr Trp
        100                 105                 110

Gly Gln Gly Thr Leu Val Thr Val Ser Ser
    115                 120

<210> SEQ ID NO 45
<211> LENGTH: 112
<212> TYPE: PRT
<213> ORGANISM: Artificial Sequence
<220> FEATURE:
<223> OTHER INFORMATION: Synthetic peptide

<400> SEQUENCE: 45

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Met Ile Tyr Ala Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Asp Glu Arg
            85                  90                  95

Phe Thr Arg Val Phe Gly Gly Gly Thr Lys Leu Thr Val Leu Gly Gln
        100                 105                 110

<210> SEQ ID NO 46
<211> LENGTH: 366
<212> TYPE: DNA
<213> ORGANISM: Artificial Sequence
<220> FEATURE:
<223> OTHER INFORMATION: Synthetic peptide

<400> SEQUENCE: 46
caggtgcaat tgcagcagag cggtccgggc ctggtgaaac cgagccagac cctgagcctg    60

```
acctgcgcga tttccggaga tagcgtgagc agtaactctg ctgcttggaa ctggattcgt      120
cagagcccga gccgtggcct cgagtggctg ggccgtacct actaccgtag caaatggaaa      180
aaagaatatg cccagagcgt gaaaagccgc attaccatta acccggatac ttcgaaaaac      240
cagtttagcc tgcaactgaa cagcgtgacc ccggaagata cggccgtgta ttattgcgcg      300
cgtgaccgtt actactactc tgctttcgat tactggggcc aaggcaccct ggtgactgtt      360
agctca                                                                366
```

<210> SEQ ID NO 47
<211> LENGTH: 336
<212> TYPE: DNA
<213> ORGANISM: Artificial Sequence
<220> FEATURE:
<223> OTHER INFORMATION: Synthetic peptide

<400> SEQUENCE: 47

```
caaagcgcgc tgacccagcc ggcgagcgtg agcggtagcc cgggccagag cattaccatt       60
agctgcaccg gcaccagcag cgatgtgggc ggttacaatt ctgtttcttg gtaccagcag      120
catccgggca aggcgccgaa attgatgatt tacgctgttt ctaaccgtcc gagcggcgtg      180
agcaaccgtt ttagcggatc caaaagcggc aacaccgcga gcctgaccat tagcggcctg      240
caagcggaag acgaagcgga ttattactgc gcttcttacg acgaacgttt cactcgtgtg      300
tttggcggcg gcacgaagtt aaccgtccta ggtcag                               336
```

<210> SEQ ID NO 48
<211> LENGTH: 7
<212> TYPE: PRT
<213> ORGANISM: Artificial Sequence
<220> FEATURE:
<223> OTHER INFORMATION: Synthetic peptide

<400> SEQUENCE: 48

Thr Ser Ser Ala Ala Trp Asn
1               5

<210> SEQ ID NO 49
<211> LENGTH: 18
<212> TYPE: PRT
<213> ORGANISM: Artificial Sequence
<220> FEATURE:
<223> OTHER INFORMATION: Synthetic peptide

<400> SEQUENCE: 49

Arg Thr Tyr Tyr Arg Ser Lys Trp Lys Lys Glu Tyr Ala Gln Ser Val
1               5                   10                  15

Lys Ser

<210> SEQ ID NO 50
<211> LENGTH: 10
<212> TYPE: PRT
<213> ORGANISM: Artificial Sequence
<220> FEATURE:
<223> OTHER INFORMATION: Synthetic peptide

<400> SEQUENCE: 50

Asp Arg Tyr Tyr Tyr Ser Ala Phe Asp Tyr
1               5                   10

<210> SEQ ID NO 51
<211> LENGTH: 14

```
<212> TYPE: PRT
<213> ORGANISM: Artificial Sequence
<220> FEATURE:
<223> OTHER INFORMATION: Synthetic peptide

<400> SEQUENCE: 51

Thr Gly Thr Ser Ser Asp Val Gly Gly Tyr Asn Ser Val Ser
1               5                   10

<210> SEQ ID NO 52
<211> LENGTH: 7
<212> TYPE: PRT
<213> ORGANISM: Artificial Sequence
<220> FEATURE:
<223> OTHER INFORMATION: Synthetic peptide

<400> SEQUENCE: 52

Ala Val Ser Asn Arg Pro Ser
1               5

<210> SEQ ID NO 53
<211> LENGTH: 10
<212> TYPE: PRT
<213> ORGANISM: Artificial Sequence
<220> FEATURE:
<223> OTHER INFORMATION: Synthetic peptide

<400> SEQUENCE: 53

Ala Ser Tyr Asp Glu Arg Phe Thr Arg Val
1               5                   10

<210> SEQ ID NO 54
<211> LENGTH: 122
<212> TYPE: PRT
<213> ORGANISM: Artificial Sequence
<220> FEATURE:
<223> OTHER INFORMATION: Synthetic peptide

<400> SEQUENCE: 54

Gln Val Gln Leu Gln Gln Ser Gly Pro Gly Leu Val Lys Pro Ser Gln
1               5                   10                  15

Thr Leu Ser Leu Thr Cys Ala Ile Ser Gly Glu Ser Val Ser Thr Ser
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Lys Lys Glu Tyr Ala
    50                  55                  60

Gln Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
            85                  90                  95

Tyr Tyr Cys Ala Arg Asp Arg Tyr Tyr Ser Ala Phe Asp Tyr Trp
        100                 105                 110

Gly Gln Gly Thr Leu Val Thr Val Ser Ser
        115                 120

<210> SEQ ID NO 55
<211> LENGTH: 112
<212> TYPE: PRT
<213> ORGANISM: Artificial Sequence
<220> FEATURE:
<223> OTHER INFORMATION: Synthetic peptide

<400> SEQUENCE: 55
```

Gln Ser Ala Leu Thr Gln Pro Ala Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Ile Ile Tyr Ala Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Asp Glu Arg
                85                  90                  95

Phe Thr Arg Val Phe Gly Gly Gly Thr Lys Leu Thr Val Leu Gly Gln
            100                 105                 110

<210> SEQ ID NO 56
<211> LENGTH: 366
<212> TYPE: DNA
<213> ORGANISM: Artificial Sequence
<220> FEATURE:
<223> OTHER INFORMATION: Synthetic peptide

<400> SEQUENCE: 56
caggtgcaat tgcagcagag cggtccgggc ctggtgaaac cgagccagac cctgagcctg      60
acctgcgcga tttccggaga aagcgtgagt accagcagtg ctgcttggaa ctggattcgt     120
cagagcccga gccgtggcct cgagtggctg ggccgtacct actaccgtag caaatggaaa     180
aaagaatatg cccagagcgt gaaaagccgc attaccatta acccggatac ttcgaaaaac     240
cagtttagcc tgcaactgaa cagcgtgacc ccggaagata cggccgtgta ttattgcgcg     300
cgtgaccgtt actactactc tgctttcgat tactggggcc aaggcaccct ggtgactgtt     360
agctca                                                                366

<210> SEQ ID NO 57
<211> LENGTH: 336
<212> TYPE: DNA
<213> ORGANISM: Artificial Sequence
<220> FEATURE:
<223> OTHER INFORMATION: Synthetic peptide

<400> SEQUENCE: 57
caaagcgcgc tgacccagcc ggcgagcgtg agcggtagcc cgggccagag cattaccatt      60
agctgcaccg gcaccagcag cgatgtgggc ggttacaact ctgtttcttg gtaccagcag     120
catccgggca aggcgccgaa actgatcatc tacgctgttt ctaaccgtcc gagcggcgtg     180
agcaaccgtt ttagcggatc caaaagcggc aacaccgcga gcctgaccat tagcggcctg     240
caagcggaag acgaagcgga ttattactgc gcttcttacg acgaacgttt cactcgtgtg     300
tttggcggcg gcacgaagtt aaccgtccta ggtcag                               336

<210> SEQ ID NO 58
<211> LENGTH: 7
<212> TYPE: PRT
<213> ORGANISM: Artificial Sequence
<220> FEATURE:
<223> OTHER INFORMATION: Synthetic peptide

<400> SEQUENCE: 58

Thr Ser Ser Ala Ala Trp Asn

```
1               5

<210> SEQ ID NO 59
<211> LENGTH: 18
<212> TYPE: PRT
<213> ORGANISM: Artificial Sequence
<220> FEATURE:
<223> OTHER INFORMATION: Synthetic peptide

<400> SEQUENCE: 59

Arg Thr Tyr Tyr Arg Ser Lys Trp Lys Lys Glu Tyr Ala Gln Ser Val
1               5                   10                  15

Lys Ser

<210> SEQ ID NO 60
<211> LENGTH: 10
<212> TYPE: PRT
<213> ORGANISM: Artificial Sequence
<220> FEATURE:
<223> OTHER INFORMATION: Synthetic peptide

<400> SEQUENCE: 60

Asp Arg Tyr Tyr Tyr Ser Ala Phe Asp Tyr
1               5                   10

<210> SEQ ID NO 61
<211> LENGTH: 14
<212> TYPE: PRT
<213> ORGANISM: Artificial Sequence
<220> FEATURE:
<223> OTHER INFORMATION: Synthetic peptide

<400> SEQUENCE: 61

Thr Gly Thr Ser Ser Asp Val Gly Gly Tyr Asn Ser Val Ser
1               5                   10

<210> SEQ ID NO 62
<211> LENGTH: 7
<212> TYPE: PRT
<213> ORGANISM: Artificial Sequence
<220> FEATURE:
<223> OTHER INFORMATION: Synthetic peptide

<400> SEQUENCE: 62

Ala Val Ser Asn Arg Pro Ser
1               5

<210> SEQ ID NO 63
<211> LENGTH: 10
<212> TYPE: PRT
<213> ORGANISM: Artificial Sequence
<220> FEATURE:
<223> OTHER INFORMATION: Synthetic peptide

<400> SEQUENCE: 63

Ala Ser Tyr Asp Glu Arg Phe Thr Arg Val
1               5                   10

<210> SEQ ID NO 64
<211> LENGTH: 122
<212> TYPE: PRT
<213> ORGANISM: Artificial Sequence
<220> FEATURE:
<223> OTHER INFORMATION: Synthetic peptide

<400> SEQUENCE: 64
```

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Thr Ser
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Lys Lys Glu Tyr Ala
    50                  55                  60

Gln Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
            85                  90                  95

Tyr Tyr Cys Ala Arg Asp Arg Tyr Tyr Ser Ala Phe Asp Tyr Trp
            100                 105                 110

Gly Gln Gly Thr Leu Val Thr Val Ser Ser
            115                 120

<210> SEQ ID NO 65
<211> LENGTH: 112
<212> TYPE: PRT
<213> ORGANISM: Artificial Sequence
<220> FEATURE:
<223> OTHER INFORMATION: Synthetic peptide

<400> SEQUENCE: 65

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Ile Ile Tyr Ala Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Asp Glu Arg
            85                  90                  95

Phe Thr Arg Val Phe Gly Gly Gly Thr Lys Leu Thr Val Leu Gly Gln
            100                 105                 110

<210> SEQ ID NO 66
<211> LENGTH: 366
<212> TYPE: DNA
<213> ORGANISM: Artificial Sequence
<220> FEATURE:
<223> OTHER INFORMATION: Synthetic peptide

<400> SEQUENCE: 66
caggtgcaat tgcagcagag cggtccgggc ctggtgaaac cgagccagac cctgagcctg      60
acctgcgcga tttccggcga cagcgtgagc accagtagtg ctgcttggaa ctggattcgt     120
cagagcccga gccgtggcct cgagtggctg ggccgtacct actaccgtag caaatggaaa     180
aaagaatatg cccagagcgt gaaaagccgc attaccatta cccgggatac ttcgaaaaac     240
cagtttagcc tgcaactgaa cagcgtgacc ccggaagata cggccgtgta ttattgcgcg     300
cgtgaccgtt actactactc tgctttcgat tactggggcc aaggcaccct ggtgactgtt     360
agctca                                                                366

<210> SEQ ID NO 67
<211> LENGTH: 336
<212> TYPE: DNA
<213> ORGANISM: Artificial Sequence
<220> FEATURE:
<223> OTHER INFORMATION: Synthetic peptide

<400> SEQUENCE: 67

```
caaagcgcgc tgacccagcc ggcgagcgtg agcggtagcc cgggccagag cattaccatt      60
agctgcaccg gcaccagcag cgatgtgggc ggttacaact ctgtttcttg gtaccagcag     120
catccgggca aggcgccgaa actgatcatc tacgctgttt ctaaccgtcc gagcggcgtg     180
agcaaccgtt ttagcggatc caaaagcggc aacaccgcga gcctgaccat tagcggcctg     240
caagcggaag acgaagcgga ttattactgc gcttcttacg acgaacgttt cactcgtgtg     300
tttggcggcg gcacgaagtt aaccgtccta ggtcag                               336
```

<210> SEQ ID NO 68
<211> LENGTH: 5
<212> TYPE: PRT
<213> ORGANISM: Artificial Sequence
<220> FEATURE:
<223> OTHER INFORMATION: Synthetic peptide

<400> SEQUENCE: 68

Ile Tyr Ala Met Ser
1               5

<210> SEQ ID NO 69
<211> LENGTH: 19
<212> TYPE: PRT
<213> ORGANISM: Artificial Sequence
<220> FEATURE:
<223> OTHER INFORMATION: Synthetic peptide

<400> SEQUENCE: 69

Arg Ile Lys Ser Asn Ala Asp Gly Gly Thr Thr Glu Tyr Ala Ala Pro
1               5                   10                  15

Val Lys Gly

<210> SEQ ID NO 70
<211> LENGTH: 11
<212> TYPE: PRT
<213> ORGANISM: Artificial Sequence
<220> FEATURE:
<223> OTHER INFORMATION: Synthetic peptide

<400> SEQUENCE: 70

Met Arg Tyr Tyr Ser Asp Leu Tyr Phe Asp Pro
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Synthetic peptide

<400> SEQUENCE: 71

Ser Gly Asp Lys Leu Gly Gln Lys Tyr Val Ser
1               5                   10

<210> SEQ ID NO 72
<211> LENGTH: 7

```
<212> TYPE: PRT
<213> ORGANISM: Artificial Sequence
<220> FEATURE:
<223> OTHER INFORMATION: Synthetic peptide

<400> SEQUENCE: 72

Gln Asp Arg Lys Arg Pro Ser
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic peptide

<400> SEQUENCE: 73

Gln Thr Trp Thr His Leu Gln Trp Val
1               5

<210> SEQ ID NO 74
<211> LENGTH: 122
<212> TYPE: PRT
<213> ORGANISM: Artificial Sequence
<220> FEATURE:
<223> OTHER INFORMATION: Synthetic peptide

<400> SEQUENCE: 74

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ile Tyr
            20                  25                  30

Ala Met Ser Trp Val Arg Gln Ala Pro Gly Lys Gly Leu Glu Trp Val
        35                  40                  45

Gly Arg Ile Lys Ser Asn Ala Asp Gly Gly Thr Thr Glu Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Met Arg Tyr Tyr Ser Asp Leu Tyr Phe Asp Pro Trp
            100                 105                 110

Gly Gln Gly Thr Leu Val Thr Val Ser Ser
        115                 120

<210> SEQ ID NO 75
<211> LENGTH: 108
<212> TYPE: PRT
<213> ORGANISM: Artificial Sequence
<220> FEATURE:
<223> OTHER INFORMATION: Synthetic peptide

<400> SEQUENCE: 75

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Gln Lys Tyr Val
            20                  25                  30

Ser Trp Tyr Gln Gln Lys Pro Gly Gln Ser Pro Val Leu Val Ile Ser
        35                  40                  45

Gln Asp Arg Lys Arg Pro Ser Gly Ile Pro Glu Arg Phe Ser Gly Ser
    50                  55                  60
```

Asn Ser Gly Asn Thr Ala Thr Leu Thr Ile Ser Gly Thr Gln Ala Glu
            65                  70                  75                  80

Asp Glu Ala Asp Tyr Tyr Cys Gln Thr Trp Thr His Leu Gln Trp Val
                85                  90                  95

Phe Gly Gly Gly Thr Lys Leu Thr Val Leu Gly Gln
            100                 105

<210> SEQ ID NO 76
<211> LENGTH: 366
<212> TYPE: DNA
<213> ORGANISM: Artificial Sequence
<220> FEATURE:
<223> OTHER INFORMATION: Synthetic peptide

<400> SEQUENCE: 76
gaagtgcagc tggtggaaag cggcggtggc ctggtgaaac caggcggcag cctgcgcctg      60
agctgcgccg ccagcggctt cacctttagc atctacgcta tgagctgggt gcgccaggcc     120
ccgggcaaag gtctggaatg gtgggccgt atcaaatcta acgctgacgg tggtactact      180
gaatatgccg ccccagtgaa aggccgcttt accattagcc gcgatgatag caaaaacacc     240
ctgtatctgc aaatgaacag cctgaaaacc gaagatacgg ccgtgtatta ttgcgcgcgt     300
atgcgttact actctgacct gtacttcgat ccgtggggtc aaggcaccct ggtgactgtc     360
tcgagc                                                                366

<210> SEQ ID NO 77
<211> LENGTH: 324
<212> TYPE: DNA
<213> ORGANISM: Artificial Sequence
<220> FEATURE:
<223> OTHER INFORMATION: Synthetic peptide

<400> SEQUENCE: 77
agctatgaac tgacccagcc gccgagcgtt agcgttagcc caggccagac cgccagcatt      60
acctgtagcg gcgacaaact ggggcaaaaa tacgtgtcct ggtatcagca gaaaccgggc     120
cagagcccgg tgctggttat cagtcaggat cgtaaacgcc cgagcggcat tccagaacgc     180
tttagcggca gcaacagcgg caacaccgcc accctgacca ttagcggcac ccaggccgaa     240
gacgaagccg attattactg ccagacttgg acccacctgc aatgggtgtt tggcggcggt     300
accaagctga ccgtgctggg ccag                                            324

<210> SEQ ID NO 78
<211> LENGTH: 5
<212> TYPE: PRT
<213> ORGANISM: Artificial Sequence
<220> FEATURE:
<223> OTHER INFORMATION: Synthetic peptide

<400> SEQUENCE: 78

Thr Tyr Ala Ile Ser
1               5

<210> SEQ ID NO 79
<211> LENGTH: 19
<212> TYPE: PRT
<213> ORGANISM: Artificial Sequence
<220> FEATURE:
<223> OTHER INFORMATION: Synthetic peptide

<400> SEQUENCE: 79

Phe Ile Lys Ser Lys His Asn Ser Gly Thr Thr Glu Tyr Ala Ala Pro

```
                1               5                       10                      15

Val Lys Gly

<210> SEQ ID NO 80
<211> LENGTH: 11
<212> TYPE: PRT
<213> ORGANISM: Artificial Sequence
<220> FEATURE:
<223> OTHER INFORMATION: Synthetic peptide

<400> SEQUENCE: 80

Met Arg Tyr Tyr Ser Asp Leu Tyr Phe Asp Pro
1               5                       10

<210> SEQ ID NO 81
<211> LENGTH: 11
<212> TYPE: PRT
<213> ORGANISM: Artificial Sequence
<220> FEATURE:
<223> OTHER INFORMATION: Synthetic peptide

<400> SEQUENCE: 81

Ser Gly Asp Lys Leu Gly Gln Lys Tyr Val Ser
1               5                       10

<210> SEQ ID NO 82
<211> LENGTH: 7
<212> TYPE: PRT
<213> ORGANISM: Artificial Sequence
<220> FEATURE:
<223> OTHER INFORMATION: Synthetic peptide

<400> SEQUENCE: 82

Gln Asp Arg Lys Arg Pro Ser
1               5

<210> SEQ ID NO 83
<211> LENGTH: 9
<212> TYPE: PRT
<213> ORGANISM: Artificial Sequence
<220> FEATURE:
<223> OTHER INFORMATION: Synthetic peptide

<400> SEQUENCE: 83

Gln Thr Trp Thr His Leu Gln Trp Val
1               5

<210> SEQ ID NO 84
<211> LENGTH: 122
<212> TYPE: PRT
<213> ORGANISM: Artificial Sequence
<220> FEATURE:
<223> OTHER INFORMATION: Synthetic peptide

<400> SEQUENCE: 84

Glu Val Gln Leu Val Glu Ser Gly Gly Gly Leu Val Lys Pro Gly Gly
1               5                       10                      15

Ser Leu Arg Leu Ser Cys Ala Ala Ser Gly Phe Thr Phe Ser Thr Tyr
                20                      25                      30

Ala Ile Ser Trp Val Arg Gln Ala Pro Gly Lys Gly Leu Glu Trp Val
            35                      40                      45

Gly Phe Ile Lys Ser Lys His Asn Ser Gly Thr Thr Glu Tyr Ala Ala
        50                      55                      60

Pro Val Lys Gly Arg Phe Thr Ile Ser Arg Asp Asp Ser Lys Asn Thr
```

```
                65                  70                  75                  80
Leu Tyr Leu Gln Met Asn Ser Leu Lys Thr Glu Asp Thr Ala Val Tyr
                    85                  90                  95

Tyr Cys Ala Arg Met Arg Tyr Tyr Ser Asp Leu Tyr Phe Asp Pro Trp
                100                 105                 110

Gly Gln Gly Thr Leu Val Thr Val Ser Ser
        115                 120
```

<210> SEQ ID NO 85
<211> LENGTH: 108
<212> TYPE: PRT
<213> ORGANISM: Artificial Sequence
<220> FEATURE:
<223> OTHER INFORMATION: Synthetic peptide

<400> SEQUENCE: 85

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Gln Lys Tyr Val
            20                  25                  30

Ser Trp Tyr Gln Gln Lys Pro Gly Gln Ser Pro Val Leu Val Ile Ser
        35                  40                  45

Gln Asp Arg Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Trp Thr His Leu Gln Trp Val
                85                  90                  95

Phe Gly Gly Gly Thr Lys Leu Thr Val Leu Gly Gln
                100                 105
```

<210> SEQ ID NO 86
<211> LENGTH: 366
<212> TYPE: DNA
<213> ORGANISM: Artificial Sequence
<220> FEATURE:
<223> OTHER INFORMATION: Synthetic peptide

<400> SEQUENCE: 86

```
gaagtgcaat tggtggaaag cggcggtggc ctggtgaaac caggcggcag cctgcgcctg      60
agctgcgccg cctccggatt cacctttct acttacgcta tctcttgggt gcgccaggcc     120
ccgggcaaag gtctcgagtg ggtgggcttc atcaaatcta acataactc tggtactact     180 gaatatgccg ccccagtgaa aggccgcttt accattagcc gcgatgattc gaaaaacacc     240
ctgtatctgc aaatgaacag cctgaaaacc gaagatacgg ccgtgtatta ttgcgcgcgt     300
atgcgttact actctgacct gtacttcgat ccgtggggtc aaggcaccct ggtgactgtc     360
tcgagc                                                                 366
```

<210> SEQ ID NO 87
<211> LENGTH: 324
<212> TYPE: DNA
<213> ORGANISM: Artificial Sequence
<220> FEATURE:
<223> OTHER INFORMATION: Synthetic peptide

<400> SEQUENCE: 87

```
agctatgaac tgacccagcc gccgagcgtt agcgttagcc caggccagac cgccagcatt      60
acctgtagcg gcgacaaact ggggcaaaaa tacgtgtcct ggtatcagca gaaaccgggc     120
```

```
cagagcccgg tgctggttat cagtcaggat cgtaaacgcc cgagcggcat tccagaacgc    180
tttagcggca gcaacagcgg caacaccgcc accctgacca ttagcggcac ccaggccgaa    240
gacgaagccg attattactg ccagacttgg acccacctgc aatgggtgtt tggcggcggt    300
accaagctga ccgtgctggg ccag                                           324
```

<210> SEQ ID NO 88
<211> LENGTH: 7
<212> TYPE: PRT
<213> ORGANISM: Artificial Sequence
<220> FEATURE:
<223> OTHER INFORMATION: Synthetic peptide

<400> SEQUENCE: 88

Ser Asn Ser Ala Ala Trp Asn
1               5

<210> SEQ ID NO 89
<211> LENGTH: 18
<212> TYPE: PRT
<213> ORGANISM: Artificial Sequence
<220> FEATURE:
<223> OTHER INFORMATION: Synthetic peptide

<400> SEQUENCE: 89

Arg Thr Tyr Tyr Arg Ser Lys Trp Lys His Glu Tyr Ala Met Ser Val
1               5                   10                  15

Lys Ser

<210> SEQ ID NO 90
<211> LENGTH: 10
<212> TYPE: PRT
<213> ORGANISM: Artificial Sequence
<220> FEATURE:
<223> OTHER INFORMATION: Synthetic peptide

<400> SEQUENCE: 90

Asp Arg Tyr Tyr Tyr Ser Ala Phe Asp Tyr
1               5                   10

<210> SEQ ID NO 91
<211> LENGTH: 14
<212> TYPE: PRT
<213> ORGANISM: Artificial Sequence
<220> FEATURE:
<223> OTHER INFORMATION: Synthetic peptide

<400> SEQUENCE: 91

Thr Gly Thr Ser Ser Asp Val Gly Gly Tyr Asn Ser Val Ser
1               5                   10

<210> SEQ ID NO 92
<211> LENGTH: 7
<212> TYPE: PRT
<213> ORGANISM: Artificial Sequence
<220> FEATURE:
<223> OTHER INFORMATION: Synthetic peptide

<400> SEQUENCE: 92

Ala Val Ser Asn Arg Pro Ser
1               5

<210> SEQ ID NO 93
<211> LENGTH: 10

```
<212> TYPE: PRT
<213> ORGANISM: Artificial Sequence
<220> FEATURE:
<223> OTHER INFORMATION: Synthetic peptide

<400> SEQUENCE: 93

Ala Ser Tyr Asp Glu Arg Phe Thr Arg Val
1               5                   10

<210> SEQ ID NO 94
<211> LENGTH: 122
<212> TYPE: PRT
<213> ORGANISM: Artificial Sequence
<220> FEATURE:
<223> OTHER INFORMATION: Synthetic peptide

<400> SEQUENCE: 94

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Lys His Glu Tyr Ala
    50                  55                  60

Met Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Arg Tyr Tyr Ser Ala Phe Asp Tyr Trp
            100                 105                 110

Gly Gln Gly Thr Leu Val Thr Val Ser Ser
        115                 120

<210> SEQ ID NO 95
<211> LENGTH: 112
<212> TYPE: PRT
<213> ORGANISM: Artificial Sequence
<220> FEATURE:
<223> OTHER INFORMATION: Synthetic peptide

<400> SEQUENCE: 95

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Met Ile Tyr Ala Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Asp Glu Arg
                85                  90                  95

Phe Thr Arg Val Phe Gly Gly Gly Thr Lys Leu Thr Val Leu Gly Gln
            100                 105                 110

<210> SEQ ID NO 96
<211> LENGTH: 366
<212> TYPE: DNA
```

<213> ORGANISM: Artificial Sequence
<220> FEATURE:
<223> OTHER INFORMATION: Synthetic peptide

<400> SEQUENCE: 96

```
caggtgcaat tgcagcagag cggtccgggc ctggtgaaac cgagccagac cctgagcctg      60
acctgcgcga tttccggaga tagcgtgagc agtaactctg ctgcttggaa ctggattcgt     120
cagagcccga gccgtggcct cgagtggctg ggccgtacct actaccgtag caaatggaaa     180
catgaatatg ccatgagcgt gaaaagccgc attaccatta acccggatac ttcgaaaaac     240
cagtttagcc tgcaactgaa cagcgtgacc ccggaagata cggccgtgta ttattgcgcg     300
cgtgaccgtt actactactc tgctttcgat tactggggcc aaggcaccct ggtgactgtt     360
agctca                                                                366
```

<210> SEQ ID NO 97
<211> LENGTH: 336
<212> TYPE: DNA
<213> ORGANISM: Artificial Sequence
<220> FEATURE:
<223> OTHER INFORMATION: Synthetic peptide

<400> SEQUENCE: 97

```
gatatcgcgc tgacccagcc ggcgagcgtg agcggtagcc cgggccagag cattaccatt      60
agctgcaccg gcaccagcag cgatgtgggc ggttacaact ctgtgtcttg gtaccagcag     120
catccgggca aggcgccgaa actgatgatc tacgctgttt ctaaccgtcc gagcggcgtg     180
agcaaccgtt ttagcggatc caaaagcggc aacaccgcga gcctgaccat tagcggcctg     240
caagcggaag acgaagcgga ttattactgc gcttcttacg acgaacgttt cactcgtgtg     300
tttggcggcg gcacgaagtt aaccgtccta ggtcag                               336
```

<210> SEQ ID NO 98
<211> LENGTH: 7
<212> TYPE: PRT
<213> ORGANISM: Artificial Sequence
<220> FEATURE:
<223> OTHER INFORMATION: Synthetic peptide

<400> SEQUENCE: 98

Ser Asn Ser Ala Ala Trp Asn
1               5

<210> SEQ ID NO 99
<211> LENGTH: 18
<212> TYPE: PRT
<213> ORGANISM: Artificial Sequence
<220> FEATURE:
<223> OTHER INFORMATION: Synthetic peptide

<400> SEQUENCE: 99

Arg Thr Tyr Tyr Arg Ser Lys Trp Lys Lys Glu Tyr Ala Gln Ser Val
1               5                   10                  15

Lys Ser

<210> SEQ ID NO 100
<211> LENGTH: 10
<212> TYPE: PRT
<213> ORGANISM: Artificial Sequence
<220> FEATURE:
<223> OTHER INFORMATION: Synthetic peptide

<400> SEQUENCE: 100

```
Asp Arg Tyr Tyr Tyr Ser Ala Phe Asp Tyr
1               5                   10

<210> SEQ ID NO 101
<211> LENGTH: 14
<212> TYPE: PRT
<213> ORGANISM: Artificial Sequence
<220> FEATURE:
<223> OTHER INFORMATION: Synthetic peptide

<400> SEQUENCE: 101

Thr Gly Thr Ser Ser Asp Val Gly Gly Tyr Asn Ser Val Ser
1               5                   10

<210> SEQ ID NO 102
<211> LENGTH: 7
<212> TYPE: PRT
<213> ORGANISM: Artificial Sequence
<220> FEATURE:
<223> OTHER INFORMATION: Synthetic peptide

<400> SEQUENCE: 102

Ala Val Ser Asn Arg Pro Ser
1               5

<210> SEQ ID NO 103
<211> LENGTH: 10
<212> TYPE: PRT
<213> ORGANISM: Artificial Sequence
<220> FEATURE:
<223> OTHER INFORMATION: Synthetic peptide

<400> SEQUENCE: 103

Ala Ser Tyr Asp Glu Arg Phe Thr Arg Val
1               5                   10

<210> SEQ ID NO 104
<211> LENGTH: 122
<212> TYPE: PRT
<213> ORGANISM: Artificial Sequence
<220> FEATURE:
<223> OTHER INFORMATION: Synthetic peptide

<400> SEQUENCE: 104

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Lys Lys Glu Tyr Ala
    50                  55                  60

Gln Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Arg Tyr Tyr Tyr Ser Ala Phe Asp Tyr Trp
            100                 105                 110

Gly Gln Gly Thr Leu Val Thr Val Ser Ser
        115                 120

<210> SEQ ID NO 105
```

<211> LENGTH: 112
<212> TYPE: PRT
<213> ORGANISM: Artificial Sequence
<220> FEATURE:
<223> OTHER INFORMATION: Synthetic peptide

<400> SEQUENCE: 105

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Met Ile Tyr Ala Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Asp Glu Arg
                85                  90                  95

Phe Thr Arg Val Phe Gly Gly Gly Thr Lys Leu Thr Val Leu Gly Gln
            100                 105                 110

<210> SEQ ID NO 106
<211> LENGTH: 366
<212> TYPE: DNA
<213> ORGANISM: Artificial Sequence
<220> FEATURE:
<223> OTHER INFORMATION: Synthetic peptide

<400> SEQUENCE: 106
caggtgcaat tgcagcagag cggtccgggc ctggtgaaac cgagccagac cctgagcctg       60
acctgcgcga tttccggaga tagcgtgagc agtaactctg ctgcttggaa ctggattcgt      120
cagagcccga ccgtggcct cgagtggctg ggccgtacct actaccgtag caaatggaaa       180
aaagaatatg cccagagcgt gaaaagccgc attaccatta cccggatac ttcgaaaaac       240 cagtttagcc tgcaactgaa cagcgtgacc ccggaagata cggccgtgta ttattgcgcg      300
cgtgaccgtt actactactc tgctttcgat tactggggcc aaggcaccct ggtgactgtt      360
agctca                                                                 366

<210> SEQ ID NO 107
<211> LENGTH: 336
<212> TYPE: DNA
<213> ORGANISM: Artificial Sequence
<220> FEATURE:
<223> OTHER INFORMATION: Synthetic peptide

<400> SEQUENCE: 107
gatatcgcgc tgacccagcc ggcgagcgtg agcggtagcc cgggccagag cattaccatt       60
agctgcaccg gcaccagcag cgatgtgggc ggttacaact ctgtgtcttg gtaccagcag      120
catccgggca aggcgccgaa actgatgatc tacgctgttt ctaaccgtcc gagcggcgtg      180
agcaaccgtt ttagcggatc caaaagcggc aacaccgcga gcctgaccat tagcggcctg      240
caagcggaag acgaagcgga ttattactgc gcttcttacg acgaacgttt cactcgtgtg      300
tttggcggcg gcacgaagtt aaccgtccta ggtcag                                336

<210> SEQ ID NO 108
<211> LENGTH: 5
<212> TYPE: PRT

```
<213> ORGANISM: Artificial Sequence
<220> FEATURE:
<223> OTHER INFORMATION: Synthetic peptide

<400> SEQUENCE: 108

Ile Tyr Ala Met Ser
1               5

<210> SEQ ID NO 109
<211> LENGTH: 19
<212> TYPE: PRT
<213> ORGANISM: Artificial Sequence
<220> FEATURE:
<223> OTHER INFORMATION: Synthetic peptide

<400> SEQUENCE: 109

Arg Ile Lys Ser Asn Ala Asp Gly Gly Thr Thr Glu Tyr Ala Ala Pro
1               5                   10                  15

Val Lys Gly

<210> SEQ ID NO 110
<211> LENGTH: 11
<212> TYPE: PRT
<213> ORGANISM: Artificial Sequence
<220> FEATURE:
<223> OTHER INFORMATION: Synthetic peptide

<400> SEQUENCE: 110

Met Arg Tyr Tyr Ser Asp Leu Tyr Phe Asp Pro
1               5                   10

<210> SEQ ID NO 111
<211> LENGTH: 11
<212> TYPE: PRT
<213> ORGANISM: Artificial Sequence
<220> FEATURE:
<223> OTHER INFORMATION: Synthetic peptide

<400> SEQUENCE: 111

Ser Gly Asp Ala Ile Gly Ser Lys Tyr Val His
1               5                   10

<210> SEQ ID NO 112
<211> LENGTH: 7
<212> TYPE: PRT
<213> ORGANISM: Artificial Sequence
<220> FEATURE:
<223> OTHER INFORMATION: Synthetic peptide

<400> SEQUENCE: 112

Lys Asp Asn Lys Arg Pro Ser
1               5

<210> SEQ ID NO 113
<211> LENGTH: 11
<212> TYPE: PRT
<213> ORGANISM: Artificial Sequence
<220> FEATURE:
<223> OTHER INFORMATION: Synthetic peptide

<400> SEQUENCE: 113

Gln Thr Ala Thr Val Ser Ser Tyr Trp Trp Val
1               5                   10

<210> SEQ ID NO 114
<211> LENGTH: 122
```

```
<212> TYPE: PRT
<213> ORGANISM: Artificial Sequence
<220> FEATURE:
<223> OTHER INFORMATION: Synthetic peptide

<400> SEQUENCE: 114

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ile Tyr
            20                  25                  30

Ala Met Ser Trp Val Arg Gln Ala Pro Gly Lys Gly Leu Glu Trp Val
        35                  40                  45

Gly Arg Ile Lys Ser Asn Ala Asp Gly Gly Thr Thr Glu Tyr Ala Ala
50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Met Arg Tyr Tyr Ser Asp Leu Tyr Phe Asp Pro Trp
            100                 105                 110

Gly Gln Gly Thr Leu Val Thr Val Ser Ser
        115                 120

<210> SEQ ID NO 115
<211> LENGTH: 110
<212> TYPE: PRT
<213> ORGANISM: Artificial Sequence
<220> FEATURE:
<223> OTHER INFORMATION: Synthetic peptide

<400> SEQUENCE: 115

Asp Ile Glu Leu Thr Gln Pro Pro Ser Val Ser Val Ser Pro Gly Gln
1               5                   10                  15

Thr Ala Ser Ile Thr Cys Ser Gly Asp Ala Ile Gly Ser Lys Tyr Val
            20                  25                  30

His Trp Tyr Gln Gln Lys Pro Gly Gln Ala Pro Val Leu Val Ile Ser
        35                  40                  45

Lys Asp Asn Lys Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Ala Thr Val Ser Ser Tyr Trp
                85                  90                  95

Trp Val Phe Gly Gly Gly Thr Lys Leu Thr Val Leu Gly Gln
            100                 105                 110

<210> SEQ ID NO 116
<211> LENGTH: 366
<212> TYPE: DNA
<213> ORGANISM: Artificial Sequence
<220> FEATURE:
<223> OTHER INFORMATION: Synthetic peptide

<400> SEQUENCE: 116
caggtgcaat tggtggaaag cggcggtggc ctggtgaaac aggcggcag cctgcgcctg    60 agctgcgccg cctccggatt caccttttct atctacgcta tgtcttgggt gcgccaggcc   120
ccgggcaaag gtctcgagtg gtgggccgt atcaaatcta acgctgacgg tggtactact   180
gaatatgccg ccccagtgaa aggccgcttt accattagcc gcgatgattc gaaaaacacc   240
```
ctgtatctgc aaatgaacag cctgaaaacc gaagatacgg ccgtgtatta ttgcgcgcgt    300
atgcgttact actctgacct gtacttcgat ccgtggggcc aaggcaccct ggtgactgtt    360
agctca                                                               366

<210> SEQ ID NO 117
<211> LENGTH: 330
<212> TYPE: DNA
<213> ORGANISM: Artificial Sequence
<220> FEATURE:
<223> OTHER INFORMATION: Synthetic peptide

<400> SEQUENCE: 117
gatatcgaac tgacccagcc gccgagcgtg agcgtgagcc cgggccagac cgcgagcatt     60
acctgtagcg gcgatgctat cggttctaaa tacgttcatt ggtaccagca gaaaccgggc    120
caggcgccgg tgctggtgat ctctaaagac aacaaacgtc cgagcggcat cccggaacgt    180
tttagcggat ccaacagcgg caacaccgcg accctgacca ttagcggcac ccaggcggaa    240
gacgaagcgg attattactg ccagactgct actgtttctt cttactggtg ggtgtttggc    300
ggcggcacga agttaaccgt cctaggtcag                                     330

<210> SEQ ID NO 118
<211> LENGTH: 6
<212> TYPE: PRT
<213> ORGANISM: Artificial Sequence
<220> FEATURE:
<223> OTHER INFORMATION: Synthetic peptide

<400> SEQUENCE: 118

Ser Asp Tyr Ala Trp Asn
1               5

<210> SEQ ID NO 119
<211> LENGTH: 16
<212> TYPE: PRT
<213> ORGANISM: Artificial Sequence
<220> FEATURE:
<223> OTHER INFORMATION: Synthetic peptide

<400> SEQUENCE: 119

Tyr Ile Ser Tyr Ser Gly Ser Thr Ser Tyr Asn Pro Ser Leu Lys Ser
1               5                   10                  15

<210> SEQ ID NO 120
<211> LENGTH: 9
<212> TYPE: PRT
<213> ORGANISM: Artificial Sequence
<220> FEATURE:
<223> OTHER INFORMATION: Synthetic peptide

<400> SEQUENCE: 120

Phe Asp Tyr Ala His Ala Met Asp Tyr
1               5

<210> SEQ ID NO 121
<211> LENGTH: 11
<212> TYPE: PRT
<213> ORGANISM: Artificial Sequence
<220> FEATURE:
<223> OTHER INFORMATION: Synthetic peptide

<400> SEQUENCE: 121

Gln Ala Ser Gln Ser Ile Gly Thr Ser Ile His
1               5                   10

<210> SEQ ID NO 122
<211> LENGTH: 7
<212> TYPE: PRT
<213> ORGANISM: Artificial Sequence
<220> FEATURE:
<223> OTHER INFORMATION: Synthetic peptide

<400> SEQUENCE: 122

Tyr Ala Ser Glu Ser Ile Ser
1               5

<210> SEQ ID NO 123
<211> LENGTH: 8
<212> TYPE: PRT
<213> ORGANISM: Artificial Sequence
<220> FEATURE:
<223> OTHER INFORMATION: Synthetic peptide

<400> SEQUENCE: 123

Gln Gln Ile Asn Ser Trp Pro Thr
1               5

<210> SEQ ID NO 124
<211> LENGTH: 118
<212> TYPE: PRT
<213> ORGANISM: Artificial Sequence
<220> FEATURE:
<223> OTHER INFORMATION: Synthetic peptide

<400> SEQUENCE: 124

Gln Val Gln Leu Gln Glu Ser Gly Pro Gly Leu Val Lys Pro Ser Gln
1               5                   10                  15

Thr Leu Ser Leu Thr Cys Thr Val Ser Asp Tyr Ser Ile Thr Ser Asp
            20                  25                  30

Tyr Ala Trp Asn Trp Ile Arg Gln Phe Pro Gly Lys Gly Leu Glu Trp
        35                  40                  45

Met Gly Tyr Ile Ser Tyr Ser Gly Ser Thr Ser Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Gln Leu Asn Ser Val Thr Ala Ala Asp Thr Ala Val Tyr Tyr Cys
                85                  90                  95

Ala Ser Phe Asp Tyr Ala His Ala Met Asp Tyr Trp Gly Gln Gly Thr
            100                 105                 110

Thr Val Thr Val Ser Ser
        115

<210> SEQ ID NO 125
<211> LENGTH: 109
<212> TYPE: PRT
<213> ORGANISM: Artificial Sequence
<220> FEATURE:
<223> OTHER INFORMATION: Synthetic peptide

<400> SEQUENCE: 125

Asp Ile Val Leu Thr Gln Ser Pro Ala Phe Leu Ser Val Thr Pro Gly
1               5                   10                  15

Glu Lys Val Thr Phe Thr Cys Gln Ala Ser Gln Ser Ile Gly Thr Ser
            20                  25                  30

Ile His Trp Tyr Gln Gln Lys Thr Asp Gln Ala Pro Lys Leu Leu Ile 35                  40                  45
Lys Tyr Ala Ser Glu Ser Ile Ser Gly Ile Pro Ser Arg Phe Ser Gly
 50                  55                  60

Ser Gly Ser Gly Thr Asp Phe Thr Leu Thr Ile Ser Ser Val Glu Ala
 65                  70                  75                  80

Glu Asp Ala Ala Asp Tyr Tyr Cys Gln Gln Ile Asn Ser Trp Pro Thr
                 85                  90                  95

Thr Phe Gly Gly Gly Thr Lys Leu Glu Ile Lys Arg Thr
            100                 105

<210> SEQ ID NO 126
<211> LENGTH: 354
<212> TYPE: DNA
<213> ORGANISM: Artificial Sequence
<220> FEATURE:
<223> OTHER INFORMATION: Synthetic peptide

<400> SEQUENCE: 126
caggtgcaat tgcaggaaag cggccctggc ctggtcaagc ctagccagac cctgagcctg      60
acctgcaccg tgtccgacta cagcatcacc agcgactacg cctggaactg gatccggcag     120
ttccccggca agggcctgga atggatgggc tacatcagct acagcggcag caccagctac     180
aaccccagcc tgaagtcccg gatcaccatc agccgggaca ccagcaagaa ccagtttagc     240
ctccagctga acagcgtgac agccgccgac accgccgtgt actactgcgc cagcttcgac     300
tacgcccacg ccatggatta ctggggccag ggcaccaccg tgaccgtcag ctca            354

<210> SEQ ID NO 127
<211> LENGTH: 327
<212> TYPE: DNA
<213> ORGANISM: Artificial Sequence
<220> FEATURE:
<223> OTHER INFORMATION: Synthetic peptide

<400> SEQUENCE: 127
gatatcgtgc tgacccagag ccccgccttt ctgagcgtga cccctggcga aaagtgaca       60 ttcacatgcc aggccagcca gagcatcggc accagcatcc actggtatca gcagaaaacc    120
gaccaggccc ccaaactcct gatcaagtac gccagcgagt ccatcagcgg catccccagc    180
agattcagcg gcagcggctc cggcaccgac ttcaccctga ccatcagcag cgtggaggcc    240
gaggacgccg ccgactacta ctgccagcag atcaacagct ggcccaccac ctttggcgga    300
ggcaccaagc tggaaatcaa gcgtacg                                        327

<210> SEQ ID NO 128
<211> LENGTH: 5
<212> TYPE: PRT
<213> ORGANISM: Artificial Sequence
<220> FEATURE:
<223> OTHER INFORMATION: Synthetic peptide

<400> SEQUENCE: 128

Ser Phe Ser Met Thr
1               5

<210> SEQ ID NO 129
<211> LENGTH: 17
<212> TYPE: PRT
<213> ORGANISM: Artificial Sequence
<220> FEATURE:
<223> OTHER INFORMATION: Synthetic peptide

```
<400> SEQUENCE: 129

Tyr Ile Ser Ser Arg Ser Ser Thr Ile Ser Tyr Ala Asp Ser Val Lys
1               5                   10                  15

Gly

<210> SEQ ID NO 130
<211> LENGTH: 12
<212> TYPE: PRT
<213> ORGANISM: Artificial Sequence
<220> FEATURE:
<223> OTHER INFORMATION: Synthetic peptide

<400> SEQUENCE: 130

Asp Pro Leu Leu Ala Gly Ala Thr Phe Phe Asp Tyr
1               5                   10

<210> SEQ ID NO 131
<211> LENGTH: 12
<212> TYPE: PRT
<213> ORGANISM: Artificial Sequence
<220> FEATURE:
<223> OTHER INFORMATION: Synthetic peptide

<400> SEQUENCE: 131

Arg Ala Ser Gln Ser Val Ser Ser Ser Tyr Leu Ala
1               5                   10

<210> SEQ ID NO 132
<211> LENGTH: 7
<212> TYPE: PRT
<213> ORGANISM: Artificial Sequence
<220> FEATURE:
<223> OTHER INFORMATION: Synthetic peptide

<400> SEQUENCE: 132

Gly Ala Ser Ser Arg Ala Thr
1               5

<210> SEQ ID NO 133
<211> LENGTH: 8
<212> TYPE: PRT
<213> ORGANISM: Artificial Sequence
<220> FEATURE:
<223> OTHER INFORMATION: Synthetic peptide

<400> SEQUENCE: 133

Gln Gln Tyr Gly Ser Ser Pro Leu
1               5

<210> SEQ ID NO 134
<211> LENGTH: 121
<212> TYPE: PRT
<213> ORGANISM: Artificial Sequence
<220> FEATURE:
<223> OTHER INFORMATION: Synthetic peptide

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
                20                  25                  30

Ser Met Thr Trp Val Arg Gln Ala Pro Gly Lys Gly Leu Glu Trp Val
            35                  40                  45

Ser Tyr Ile Ser Ser Arg Ser Ser Thr Ile Ser Tyr Ala Asp Ser Val
```

```
                50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                 85                  90                  95

Ala Arg Asp Pro Leu Leu Ala Gly Ala Thr Phe Phe Asp Tyr Trp Gly
                100                 105                 110

Gln Gly Thr Leu Val Thr Val Ser Ser
        115                 120

<210> SEQ ID NO 135
<211> LENGTH: 110
<212> TYPE: PRT
<213> ORGANISM: Artificial Sequence
<220> FEATURE:
<223> OTHER INFORMATION: Synthetic peptide

<400> SEQUENCE: 135

Asp Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Leu Thr Phe Gly Gly Gly Thr Lys Val Glu Ile Lys Arg Thr
                100                 105                 110

<210> SEQ ID NO 136
<211> LENGTH: 363
<212> TYPE: DNA
<213> ORGANISM: Artificial Sequence
<220> FEATURE:
<223> OTHER INFORMATION: Synthetic peptide

<400> SEQUENCE: 136
caggtgcaat tggtggagag cggcggagga ctggtgcagc ctggcggaag cctgagactg      60
tcttgcgccg ccagcggctt caccttcagc agcttcagca tgacatgggt ccgccaagcc     120
cctggaaagg gcctggaatg ggtgtcctac atcagcagcc ggtccagcac catcagctac     180
gccgacagcg tgaagggccg gttcaccatc agccgggaca cgccaagaa cagcctgtac     240 ctgcagatga acagcctgcg ggacgaggac accgccgtgt actactgcgc cagagatcct     300
ctgctggctg gcgccacctt cttcgactac tggggccagg gcaccctggt cacagtcagc     360
tca                                                                   363

<210> SEQ ID NO 137
<211> LENGTH: 330
<212> TYPE: DNA
<213> ORGANISM: Artificial Sequence
<220> FEATURE:
<223> OTHER INFORMATION: Synthetic peptide

<400> SEQUENCE: 137
```

-continued

```
gatatcgtgc tgacccagtc tcctggcacc ctgtctctga gccctggcga gagagccacc        60
ctgagctgca gagccagcca gagcgtgtcc agcagctacc tggcctggta tcagcagaag       120
cccggccagg cccccagact gctgatctac ggcgccagca gcagagccac cggcatcccc       180
gacagattca gcggcagcgg ctccggcacc gacttcaccc tgaccatctc tcggctggaa       240
cccgaggact tcgccgtgta ctactgccag cagtacggca gcagccctct gaccttcggc       300
ggaggcacca aggtggagat caagcgtacg                                        330
```